US011944360B2

(12) United States Patent
Oberli et al.

(10) Patent No.: US 11,944,360 B2
(45) Date of Patent: Apr. 2, 2024

(54) DEFORMABLE THREADED LOCKING STRUCTURES, AND RELATED SYSTEMS AND METHODS

(71) Applicant: DePuy Synthes Products, Inc., Raynham, MA (US)

(72) Inventors: Joel Oberli, Niederdorf (CH); This Aebi, Grenchen (CH); Mirko Rocci, Bettlach (CH); Johanna F. Menze, Zurich (CH); Said Ghammar, Zuchwil (CH)

(73) Assignee: DePuy Synthes Products, Inc., Raynham, MA (US)

( * ) Notice: Subject to any disclaimer, the term of this patent is extended or adjusted under 35 U.S.C. 154(b) by 730 days.

(21) Appl. No.: 17/062,708

(22) Filed: Oct. 5, 2020

(65) Prior Publication Data

US 2021/0015526 A1      Jan. 21, 2021

Related U.S. Application Data

(63) Continuation-in-part of application No. 16/437,105, filed on Jun. 11, 2019, now Pat. No. 11,179,180.

(51) Int. Cl.
*A61B 17/80* (2006.01)
*A61B 17/00* (2006.01)

(52) U.S. Cl.
CPC ...... *A61B 17/8014* (2013.01); *A61B 17/8057* (2013.01); *A61B 2017/00862* (2013.01)

(58) Field of Classification Search
CPC ............ A61B 17/8014; A61B 17/8057; A61B 17/8052
See application file for complete search history.

(56) References Cited

U.S. PATENT DOCUMENTS

| 6,669,701 B2 | 12/2003 | Steiner et al. |
| 6,719,759 B2 | 4/2004 | Wagner et al. |
| 6,730,091 B1 | 5/2004 | Pfefferle et al. |

(Continued)

FOREIGN PATENT DOCUMENTS

| DE | 102015102629 B4 | 10/2022 |
| EP | 2919688 A1 | 9/2015 |

(Continued)

OTHER PUBLICATIONS

U.S. Appl. No. 63/107,699, filed Oct. 30, 2020 entitled Bone Plates Having Multi-Use Screw Holes For Locking And Compression Screws, And Related Systems And Methods.

*Primary Examiner* — Andrew Yang
(74) *Attorney, Agent, or Firm* — BakerHostetler

(57) ABSTRACT

A bone plate includes a plate body defining an outer surface, an opposed bone-facing surface, and a combination hole comprising a locking hole and a compression hole that intersect one another and each extending from the outer surface to the bone-facing surface. The locking hole and the compression hole extend away from each other along a longitudinal axis. The plate body further defines a locking surface that defines the locking hole, and a second surface that defines the compression hole. The locking surface further defines a plurality of columns sequentially located about a central axis of the locking hole, a plurality of recesses located, respectively, between at least some of the columns, and plate threads that traverse each of the columns. Crests of the plate threads extend linearly from a first side of each column to a second side of each column.

20 Claims, 84 Drawing Sheets

(56) References Cited

U.S. PATENT DOCUMENTS

| | | |
|---|---|---|
| 7,354,441 B2 | 4/2008 | Frigg |
| 7,695,502 B2 | 4/2010 | Orbay et al. |
| 7,776,076 B2 | 8/2010 | Grady et al. |
| 7,951,176 B2 | 5/2011 | Grady et al. |
| 7,976,570 B2 | 7/2011 | Wagner et al. |
| 8,343,196 B2 | 1/2013 | Schneider |
| 8,758,346 B2 | 6/2014 | Koay et al. |
| 8,845,698 B2 | 9/2014 | Schneider |
| 8,852,245 B2 | 10/2014 | Schneider |
| 8,876,873 B2 | 11/2014 | Schneider |
| 8,940,029 B2 | 1/2015 | Leung et al. |
| 9,107,711 B2 | 8/2015 | Hainard |
| 9,161,791 B2 | 10/2015 | Frigg |
| 9,295,505 B2 | 3/2016 | Schneider |
| 9,308,034 B2 | 4/2016 | Grady et al. |
| 9,314,284 B2 | 4/2016 | Chan et al. |
| 9,931,148 B2 | 4/2018 | Grady et al. |
| 10,231,768 B2 | 3/2019 | Grady et al. |
| 10,342,586 B2 | 7/2019 | Schneider |
| 10,653,466 B2 | 5/2020 | Grady et al. |
| 10,772,665 B2 | 9/2020 | Bosshard et al. |
| 2008/0161860 A1 | 7/2008 | Ahrens et al. |
| 2009/0312803 A1 | 12/2009 | Austin et al. |
| 2012/0265255 A1 | 10/2012 | Hilse et al. |
| 2014/0018862 A1 | 1/2014 | Koay et al. |
| 2014/0316473 A1 | 10/2014 | Pfeiffer et al. |
| 2016/0367299 A1 | 12/2016 | Paolino et al. |
| 2018/0132913 A1 | 5/2018 | Davison et al. |
| 2018/0161081 A1 | 6/2018 | Anding et al. |
| 2018/0250043 A1 | 9/2018 | Rapalo et al. |
| 2018/0310972 A1 | 11/2018 | Anding et al. |
| 2019/0269444 A1 | 9/2019 | Schneider |
| 2019/0328430 A1 | 10/2019 | Bosshard et al. |
| 2020/0237420 A1 | 7/2020 | Grady et al. |
| 2020/0390483 A1 | 12/2020 | Oberli et al. |
| 2021/0015526 A1 | 1/2021 | Oberli et al. |

FOREIGN PATENT DOCUMENTS

| | | |
|---|---|---|
| WO | 2006/014436 A1 | 2/2006 |
| WO | 2013/036362 A1 | 3/2013 |
| WO | 2014/078289 A1 | 5/2014 |
| WO | 2019/211681 A1 | 11/2019 |
| WO | 2020/234669 A1 | 11/2020 |
| WO | 2020/250052 A1 | 12/2020 |

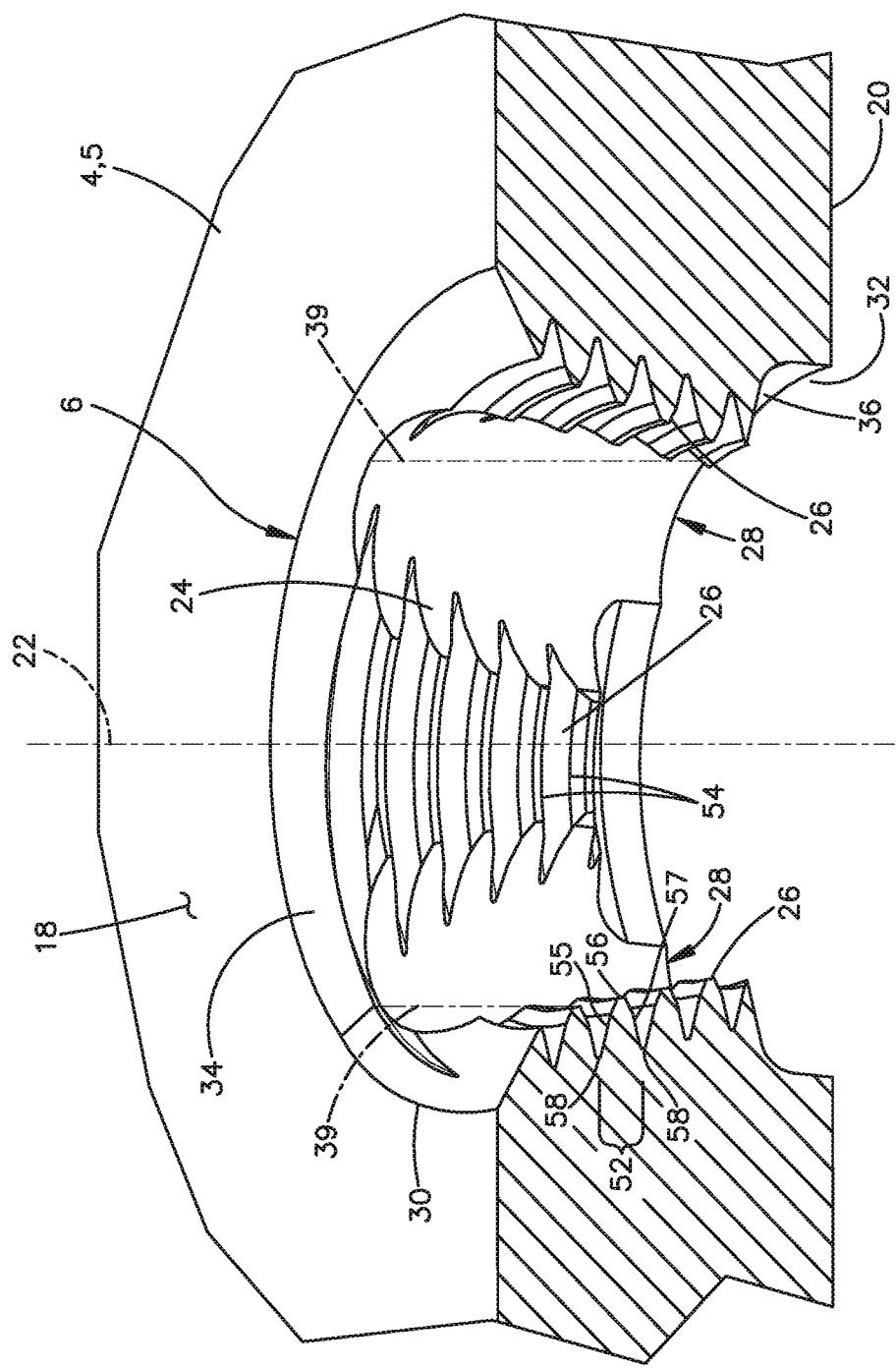

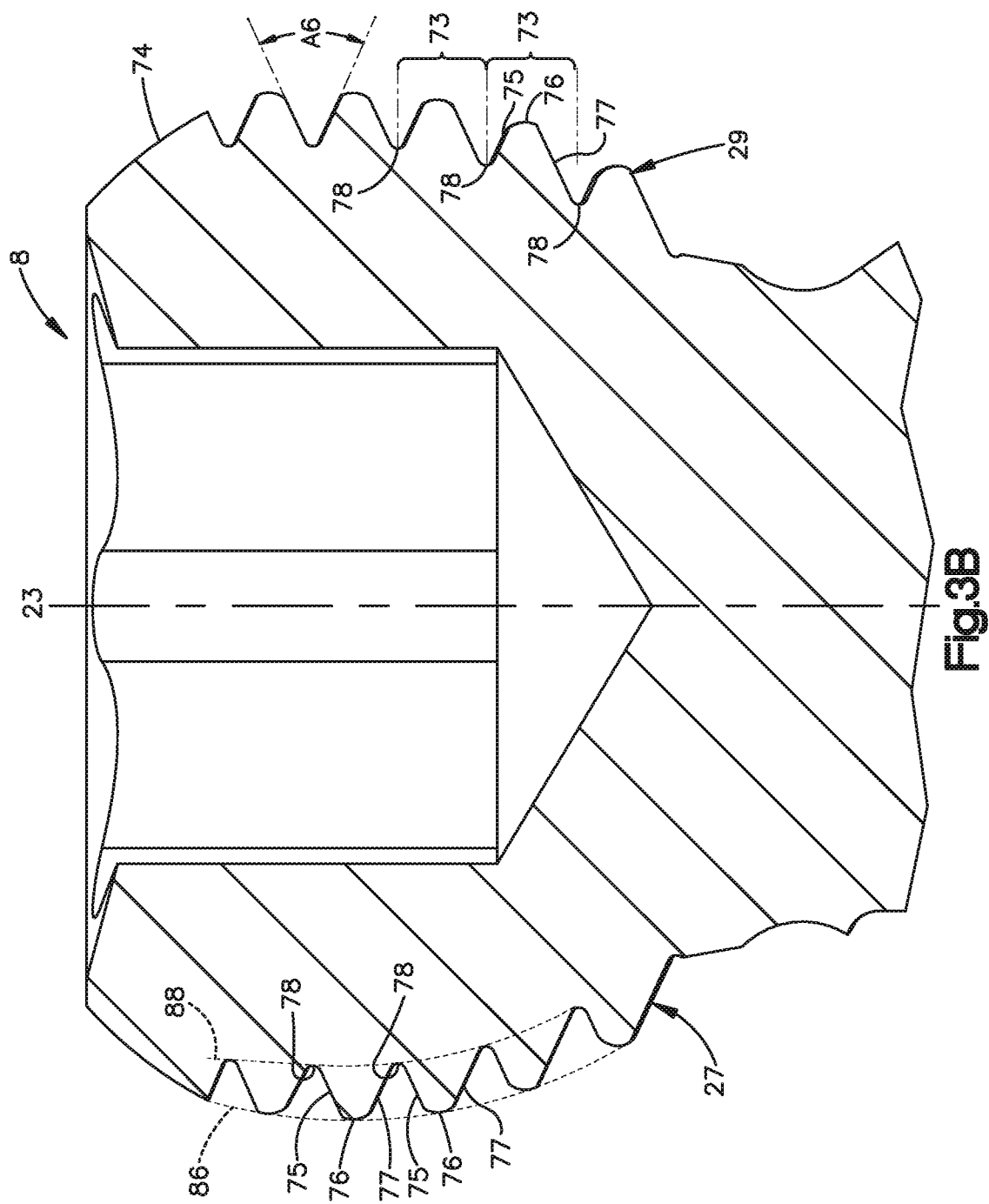

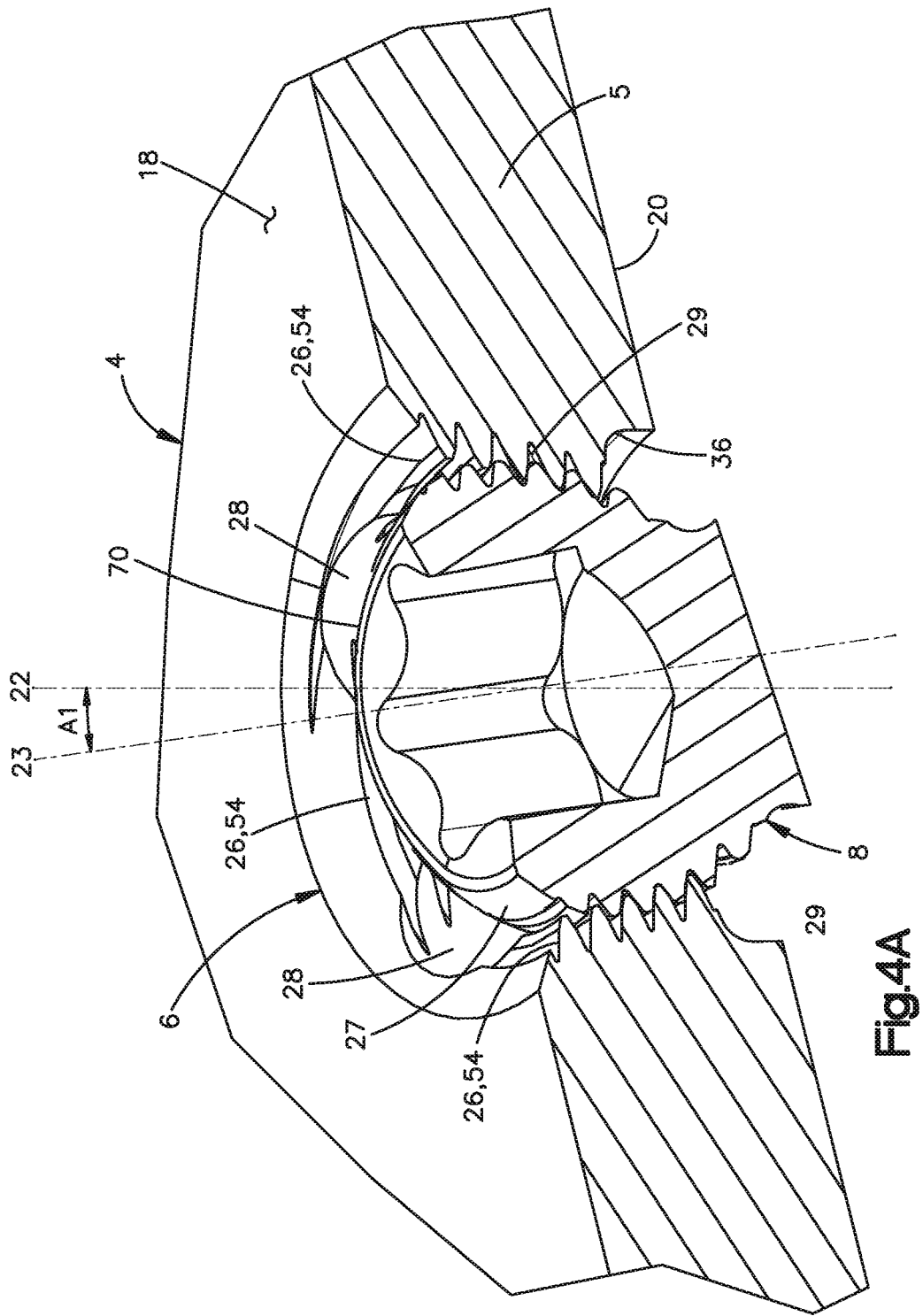

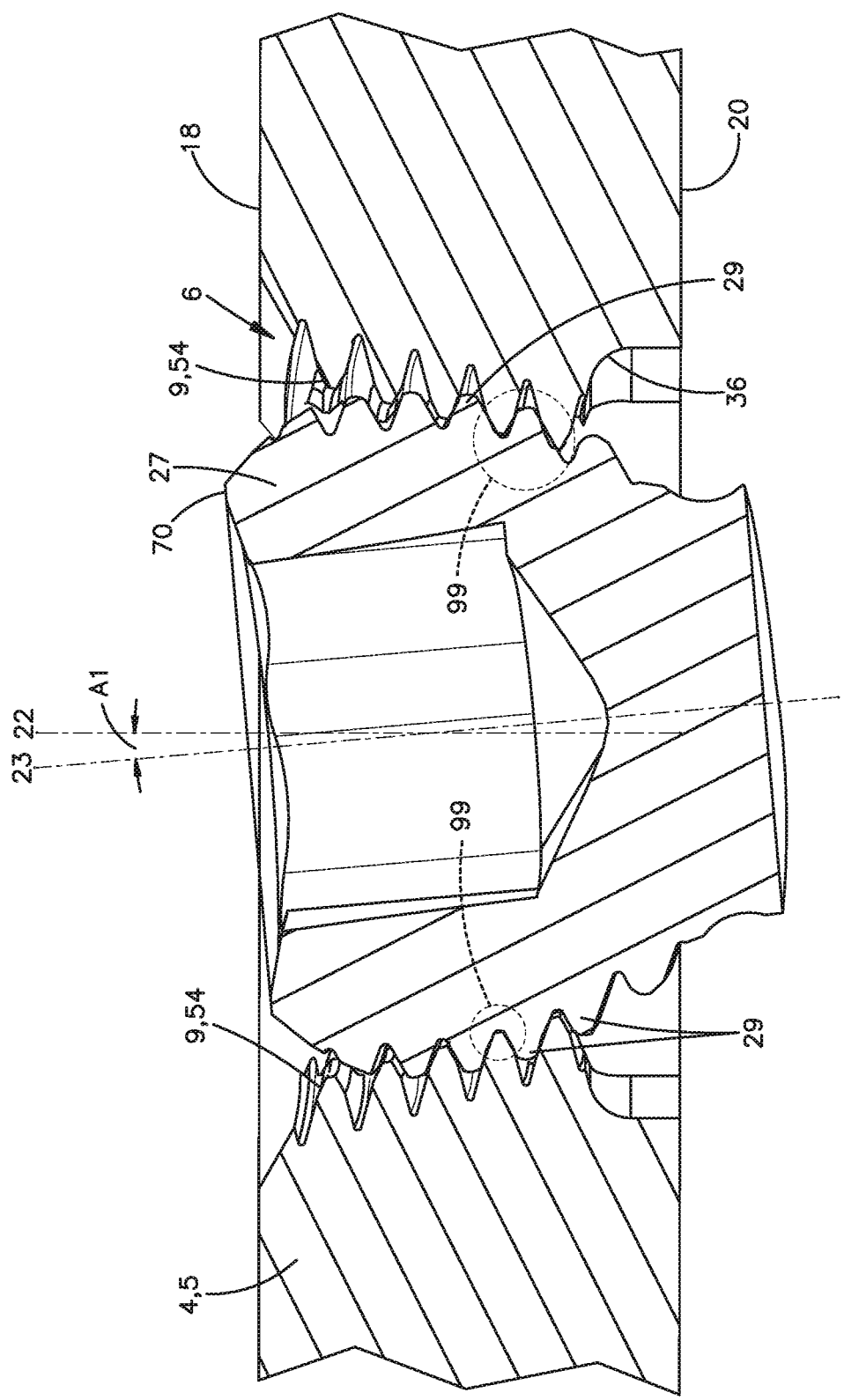

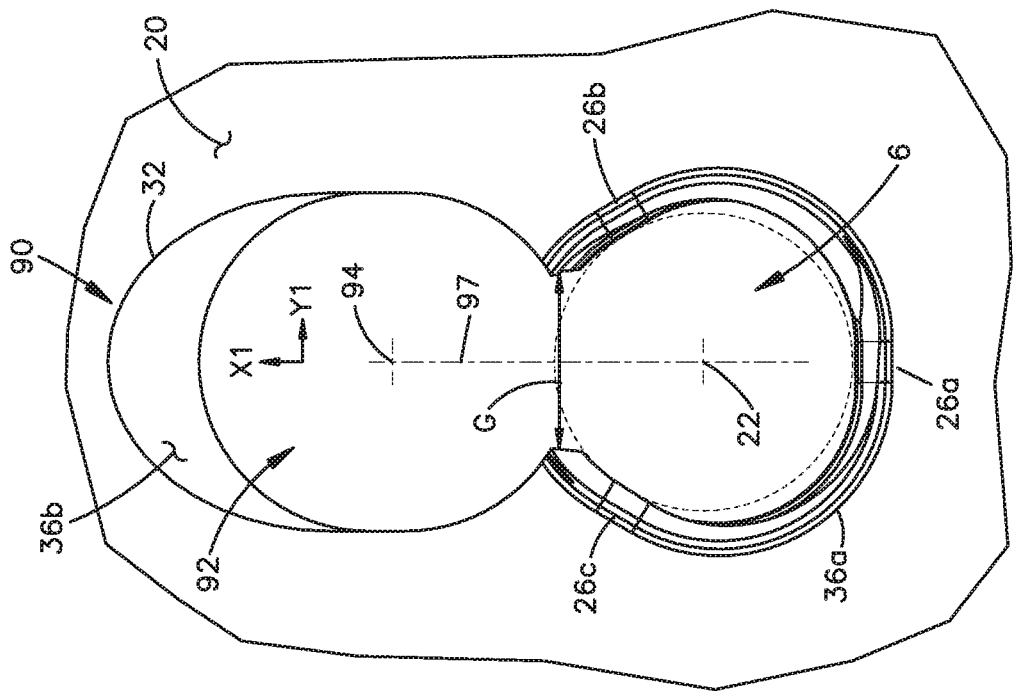
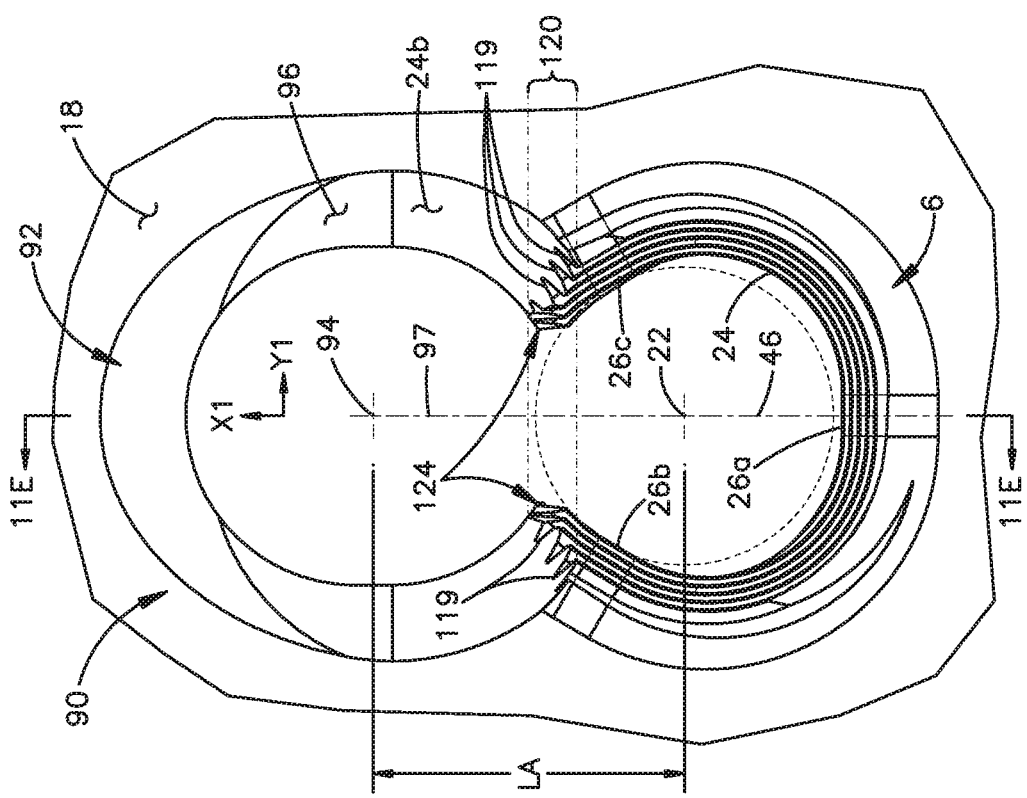

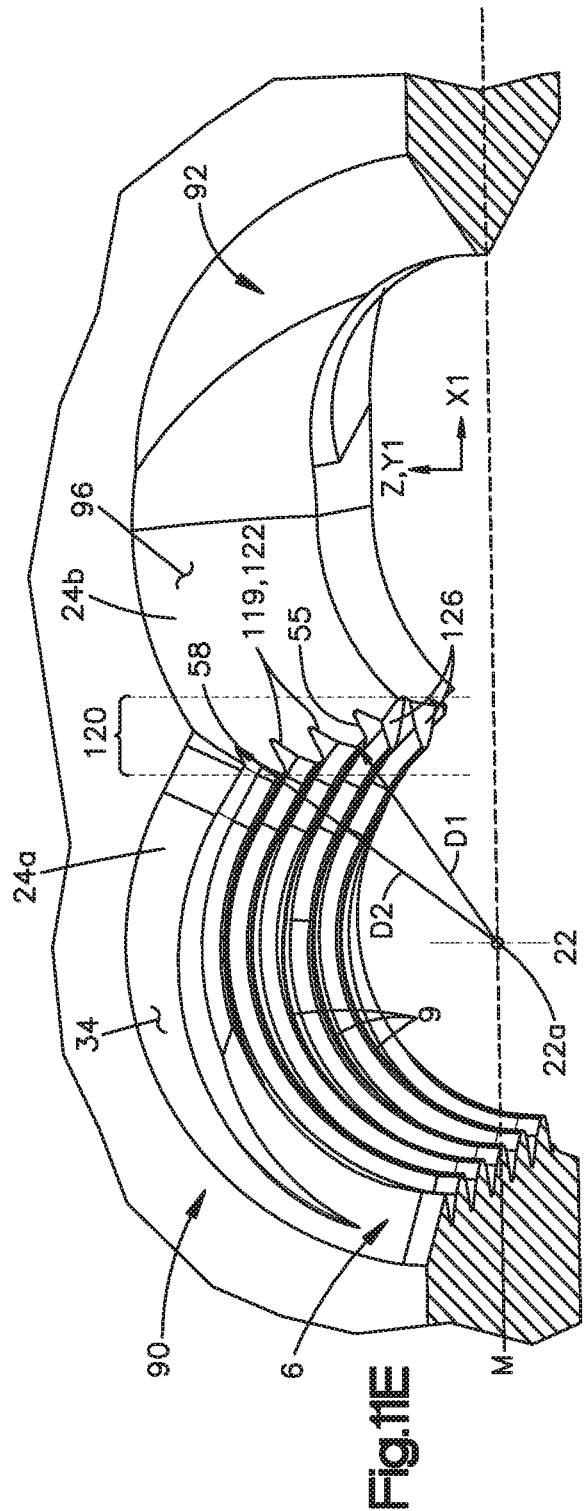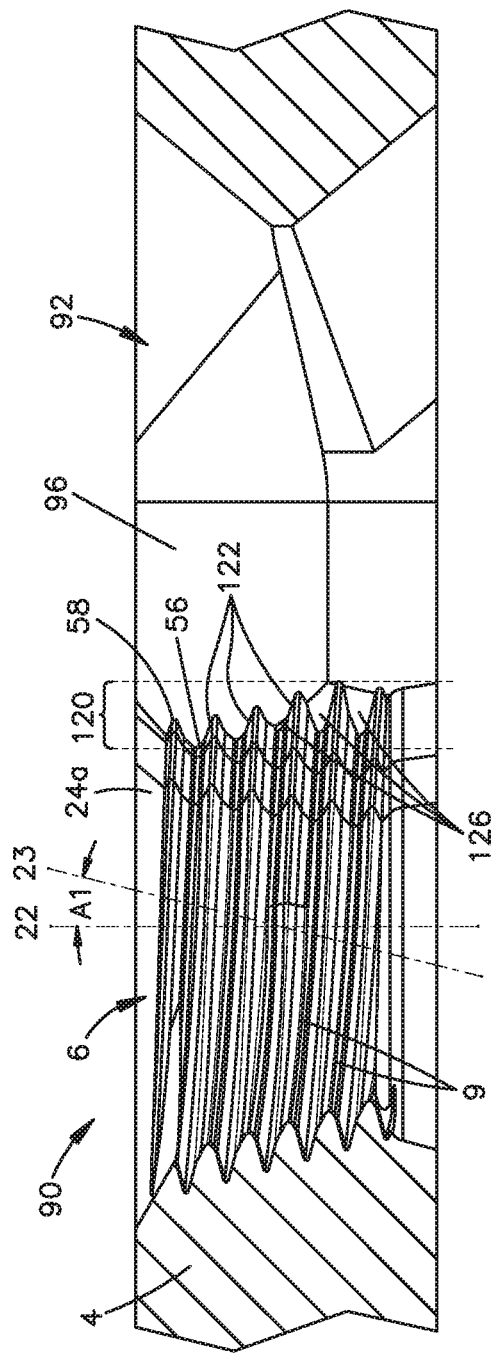

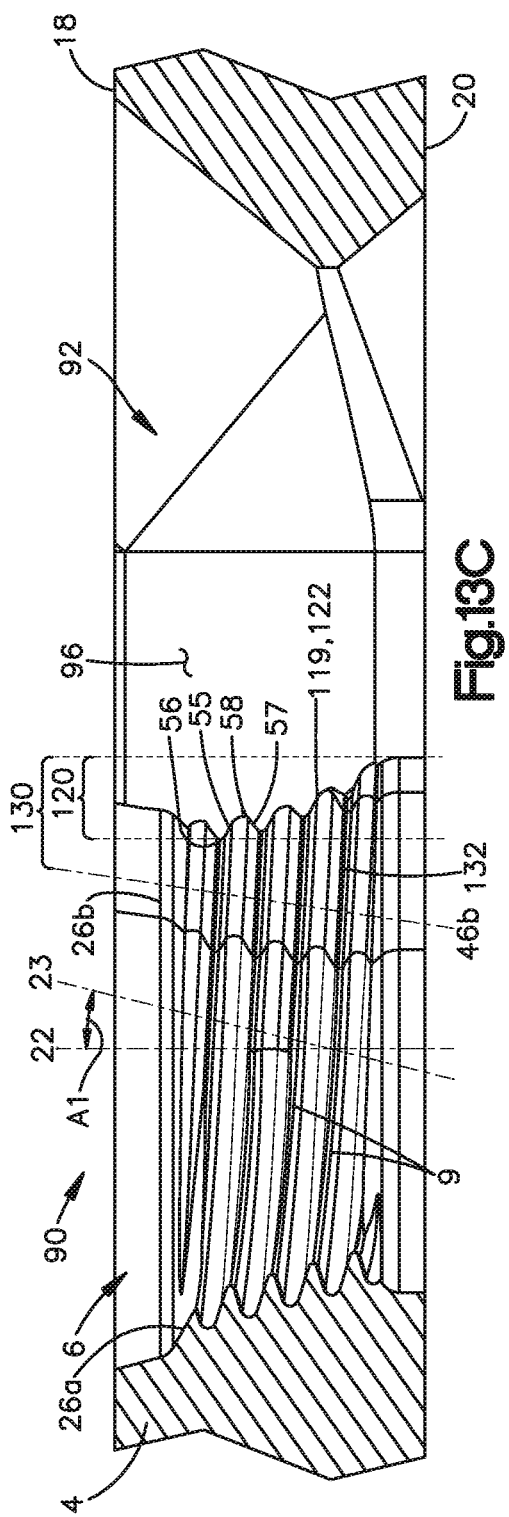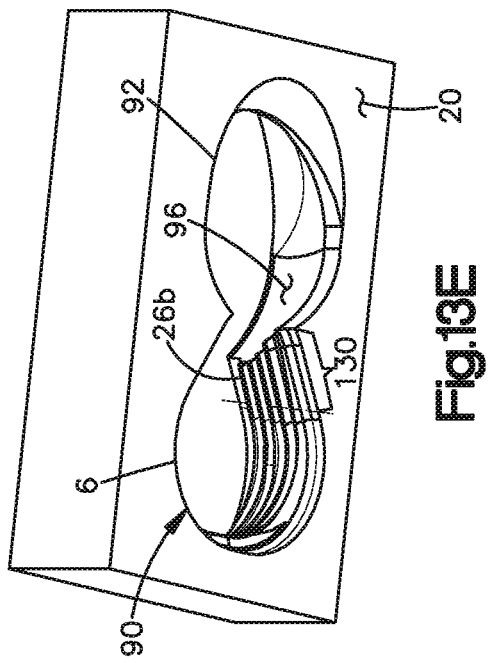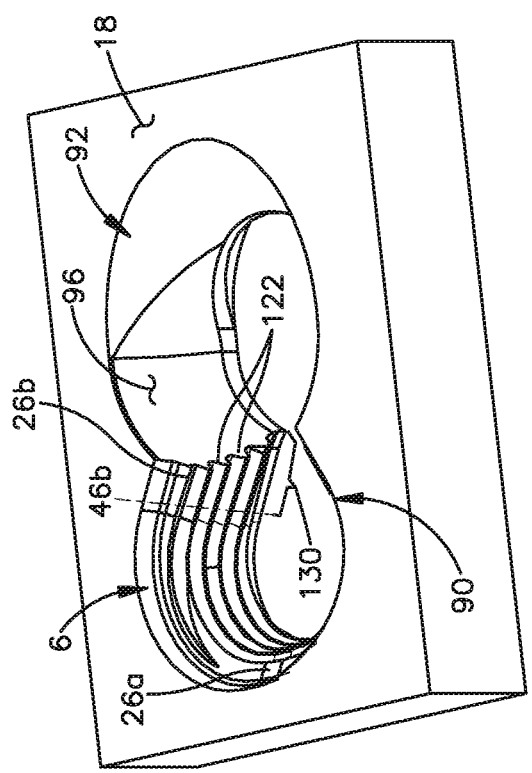

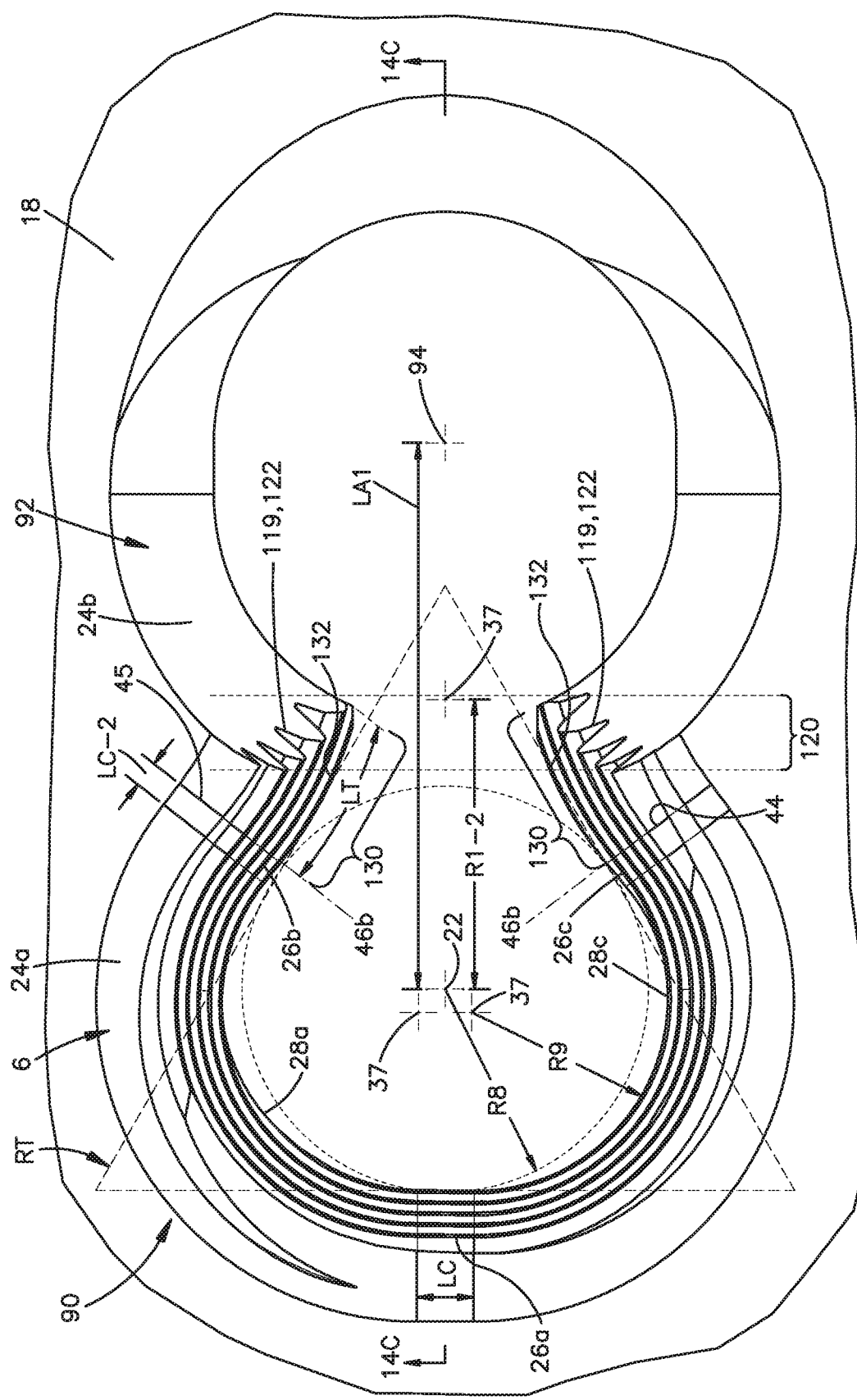

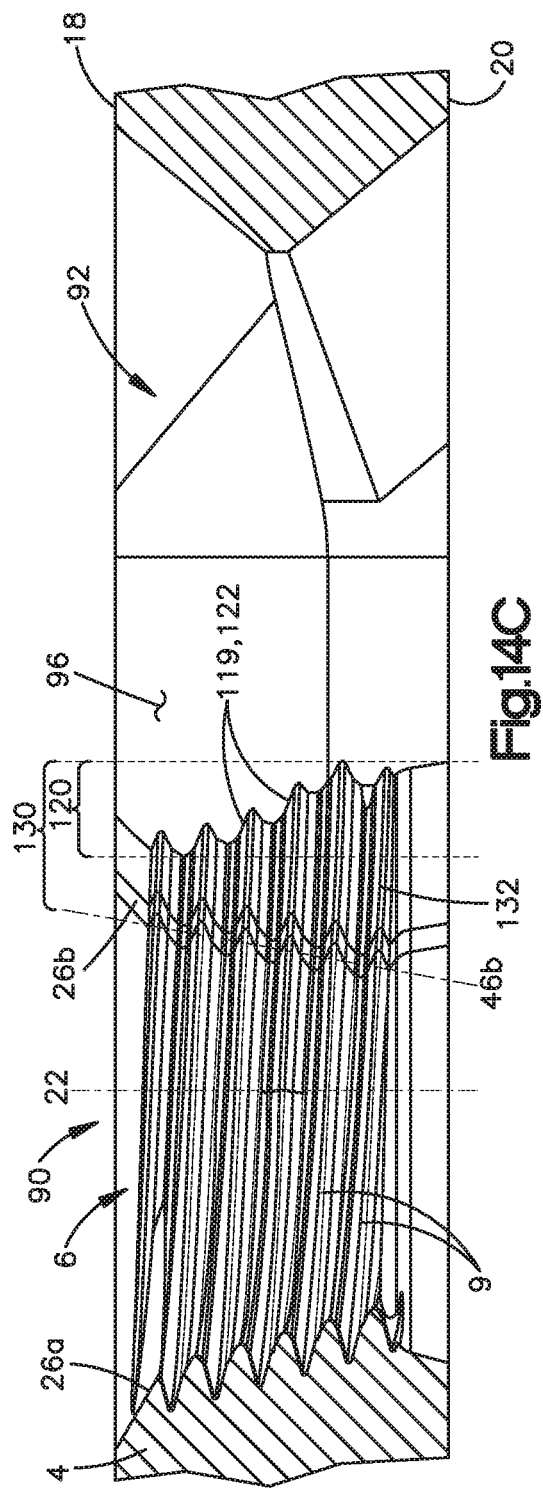
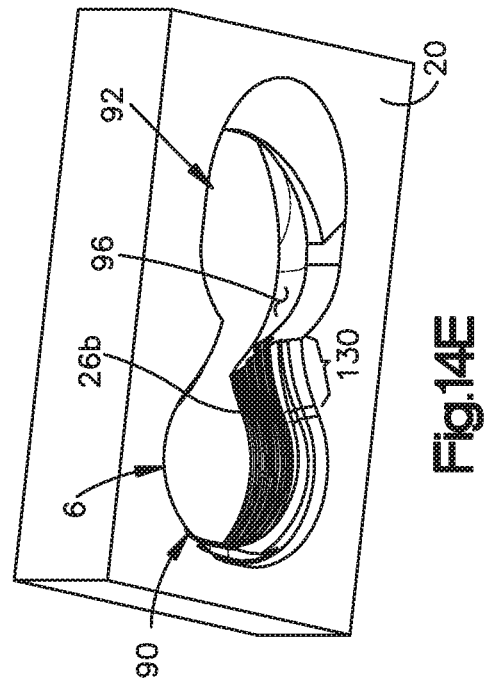
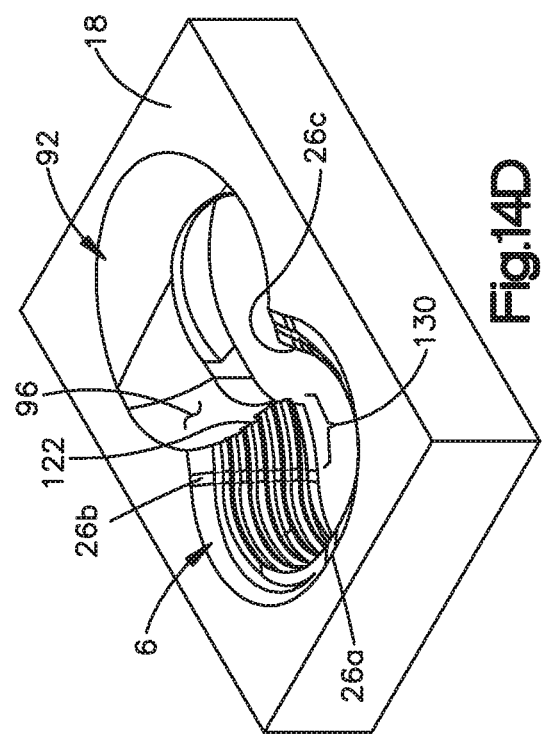
Fig.14C
Fig.14E
Fig.14D

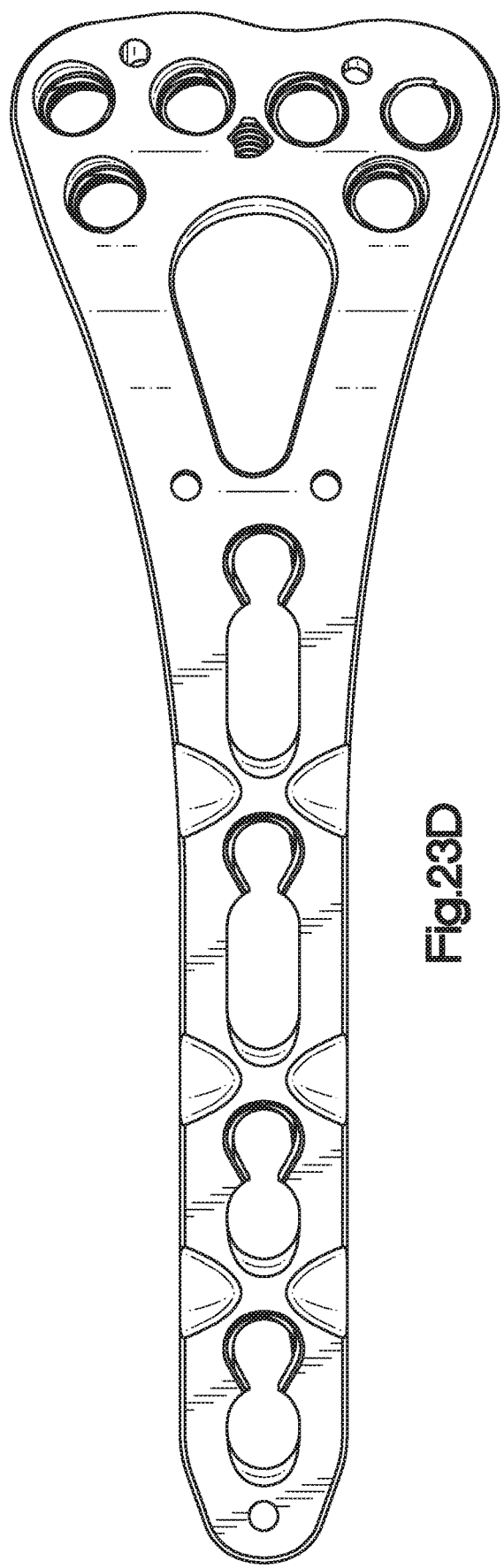
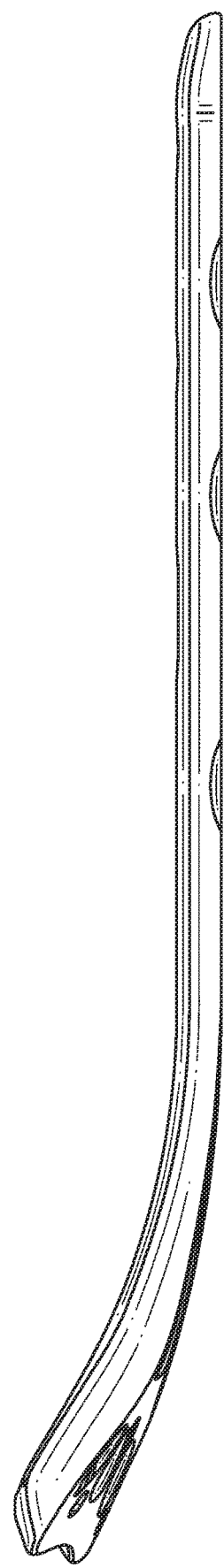

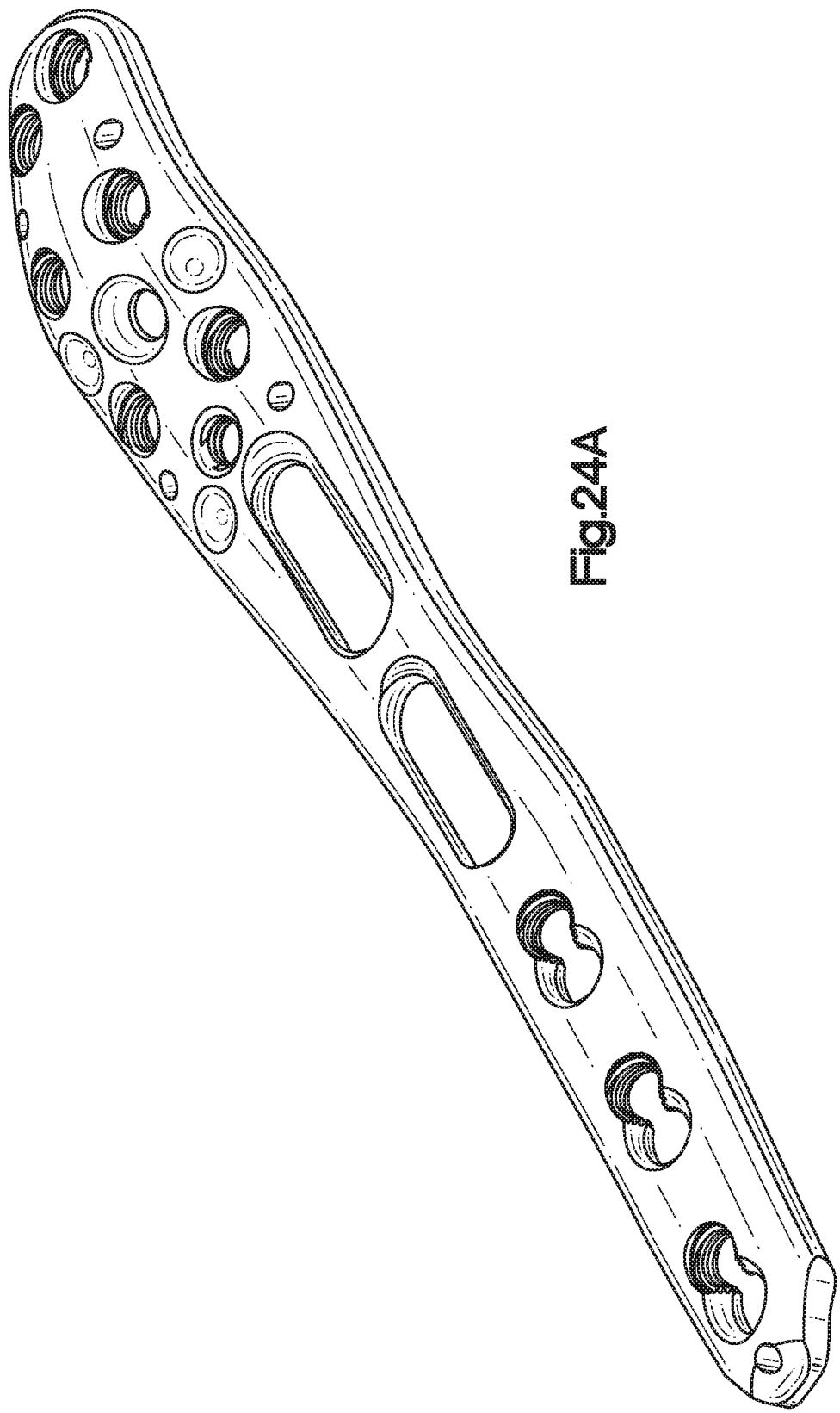

DEFORMABLE THREADED LOCKING STRUCTURES, AND RELATED SYSTEMS AND METHODS

CROSS REFERENCE TO RELATED APPLICATIONS

This application is a Continuation-in-Part of U.S. patent application Ser. No. 16/437,105, filed Jun. 11, 2019, the entire contents of which are hereby incorporated herein by this reference.

TECHNICAL FIELD

The present invention relates to bone plates and bone anchors for coupling to the bone plates, and particularly relates to threaded locking structures defined within a fixation hole of a bone plate and complimentary threaded locking structures defined on a head of a bone anchor.

BACKGROUND

Bone plate systems for the internal fixation of bone fractures are well known. Conventional bone plate systems are particularly well-suited to promote the healing of a fracture. A bone anchor, such as a bone screw, is inserted through a fixation aperture or hole in a bone plate and is threaded into bone to compress, neutralize, buttress, tension, band, and/or bridge the fracture ends together. Bone screws that are capable of locking with the bone plate can be employed to transfer loads from one fractured bone part, over a plate, and onto another fractured bone part without drawing the bone against the plate, and to avoid loosening or backing out the bone screws with respect to the plate (which can lead to poor alignment and poor clinical results). One known embodiment of such a screw employs a screw head with external threads for engaging with a corresponding thread on the inner surface of a fixation hole to lock the screw to the plate. These screws, which are hereinafter referred to as "locking screws" or "compression screws", and which can include standard-type locking screws that are configured to lock within fixation hole substantially only at a "nominal" orientation whereby the central screw axis is substantially aligned with the central hole axis, as well as "variable-angle" (VA) locking screws that are configured to lock within a fixation hole at either a nominal orientation or an "angulated" orientation whereby the central screw axis is oriented at an acute angle with respect to the respective central hole axis.

SUMMARY

According to an embodiment of the present disclosure, a bone fixation system includes a plate body that defines an interior surface that defines at least one hole defining a central axis. The internal surface defines plate threads within the hole. The system includes a bone screw having a shaft extending from head along a central axis, wherein the head has an exterior surface that defines threads that are configured to threadedly engage the plate threads. The plate threads and head threads each have a cross-sectional profile in a respective reference plane extending along the respective central axis. The cross-sectional profiles each comprise roots, crests, and flanks extending therebetween. The roots, crests, and flanks collectively deviate from a reference cross-sectional profile that is V-shaped in the respective reference plane and defines crest reference points at apices at a first side thereof and root reference points at apices at a second side thereof opposite the first side. Such deviation causes a thread height measured from the crests to the roots to be less than a reference height measured from the crest reference points to the root reference points, such that a ratio of the thread height of the head threads to the reference height of the head threads is from 0.50:1 to 0.80:1, and a ratio of the thread height of the plate threads to the reference height of the plate threads is from 0.50:1 to 1.00:1.

According to another embodiment of the present disclosure, a bone plate includes a plate body defining an outer surface, an opposed bone-facing surface, and a combination hole comprising a locking hole and a compression hole that intersect one another and each extending from the outer surface to the bone-facing surface. The locking hole and the compression hole extend away from each other along a longitudinal axis. The plate body further defines a locking surface that defines the locking hole, and a second surface that defines the compression hole. The locking surface further defines a plurality of columns sequentially located about a central axis of the locking hole in a polygonal pattern, a plurality of recesses located, respectively, between at least some of the columns, and plate threads that traverse each of the columns. Crests of the plate threads extend linearly from a first side of each column to a second side of each column.

According to an additional embodiment of the present disclosure, a bone plate includes a plate body that defines a combination hole comprising a locking hole and a compression hole that intersect one another and each extends from an outer surface of the plate body to a bone-facing surface of the plate body. The locking hole and the compression hole extend away from each other along a longitudinal axis. The plate body further defines 1) a locking surface that defines the locking hole, 2) a second surface that defines the compression hole, and 3) interface edges along an intersection boundary between the locking surface and the second surface. The locking surface further defines first, second, and third columns sequentially located about a central axis of the locking hole, each column having a first side and a second side. The locking surface further defines a first recess extending from the second side of the first column to the first side of the second column, an additional recess extending from the second side of the third column to the first side of the first column, and a transition zone between the first side of the second column and the second side of the third column, wherein the locking surface in the transition zone is elongated and extends to the intersection boundary. The locking surface also defines plate threads that traverse each of the columns and at least portions of the first recess, the additional recess, and the transition zone. Crests of the plate threads extend linearly from the first side to the second side of each column.

BRIEF DESCRIPTION OF THE DRAWINGS

The foregoing summary, as well as the following detailed description of illustrative embodiments of the present application, will be better understood when read in conjunction with the appended drawings. For the purposes of illustrating the locking structures of the present application, there is shown in the drawings illustrative embodiments. It should be understood, however, that the application is not limited to the precise arrangements and instrumentalities shown. In the drawings:

FIG. 2B is a sectional perspective view of the locking hole illustrated in FIG. 2A;

FIG. 3B is a sectional side view of the VA locking screw illustrated in FIG. 3A, taken along the central axis of the screw;

FIG. 4A is a sectional perspective view of the head of the VA locking screw illustrated in FIG. 3A in locking engagement with the locking hole illustrated in FIG. 2A;

FIG. 4B is a sectional side view of the head of the VA locking screw in locking engagement with the locking hole illustrated in FIG. 4A;

FIG. 11C is a top plan view of the combination hole illustrated in FIG. 11A;

FIG. 11D is a bottom plan view of the combination hole illustrated in FIG. 11A;

FIG. 11E is a sectional perspective view of the combination hole taken along section line 11E-11E illustrated in FIG. 11C;

FIG. 11F is a sectional side view of the combination hole taken along section line 11E-11E illustrated in FIG. 11C;

FIG. 13C is a sectional side view of the combination hole taken along section line 13C-13C illustrated in FIG. 13A;

FIG. 13D is a perspective view of the combination hole illustrated in FIG. 13A;

FIG. 13E is another perspective view of the combination hole illustrated in FIG. 13A;

FIG. 14A is a top plan view of a combination hole having an arcuate and convex transition zone between the trigon locking hole and the compression hole, according to another embodiment of the present disclosure;

FIG. 14C is a sectional side view of the combination hole taken along section line 14C-14C illustrated in FIG. 14A;

FIG. 14D is a perspective view of the combination hole illustrated in FIG. 14A;

FIG. 14E is another perspective view of the combination hole illustrated in FIG. 14A;

FIGS. 23A through 23G show respective views of a third additional bone plate, according to another embodiment of the present disclosure, the bone plate having various combination holes that include a trigon locking hole intersected by a compression hole, these views being a perspective view (FIG. 23A), top view (FIG. 23B), right side view (FIG. 23C), bottom view (FIG. 23D), left side view (FIG. 23E), front view (FIG. 23F), and rear view (FIG. 23G) of the bone plate;

FIGS. 24A through 24G show respective views of a fourth additional bone plate, according to another embodiment of the present disclosure, the bone plate having various combination holes that include a trigon locking hole intersected by a compression hole, these views being a perspective view (FIG. 24A), top view (FIG. 24B), right side view (FIG. 24C), bottom view (FIG. 24D), left side view (FIG. 24E), front view (FIG. 24F), and rear view (FIG. 24G) of the bone plate;

DETAILED DESCRIPTION OF ILLUSTRATIVE EMBODIMENTS

Figure 1A:
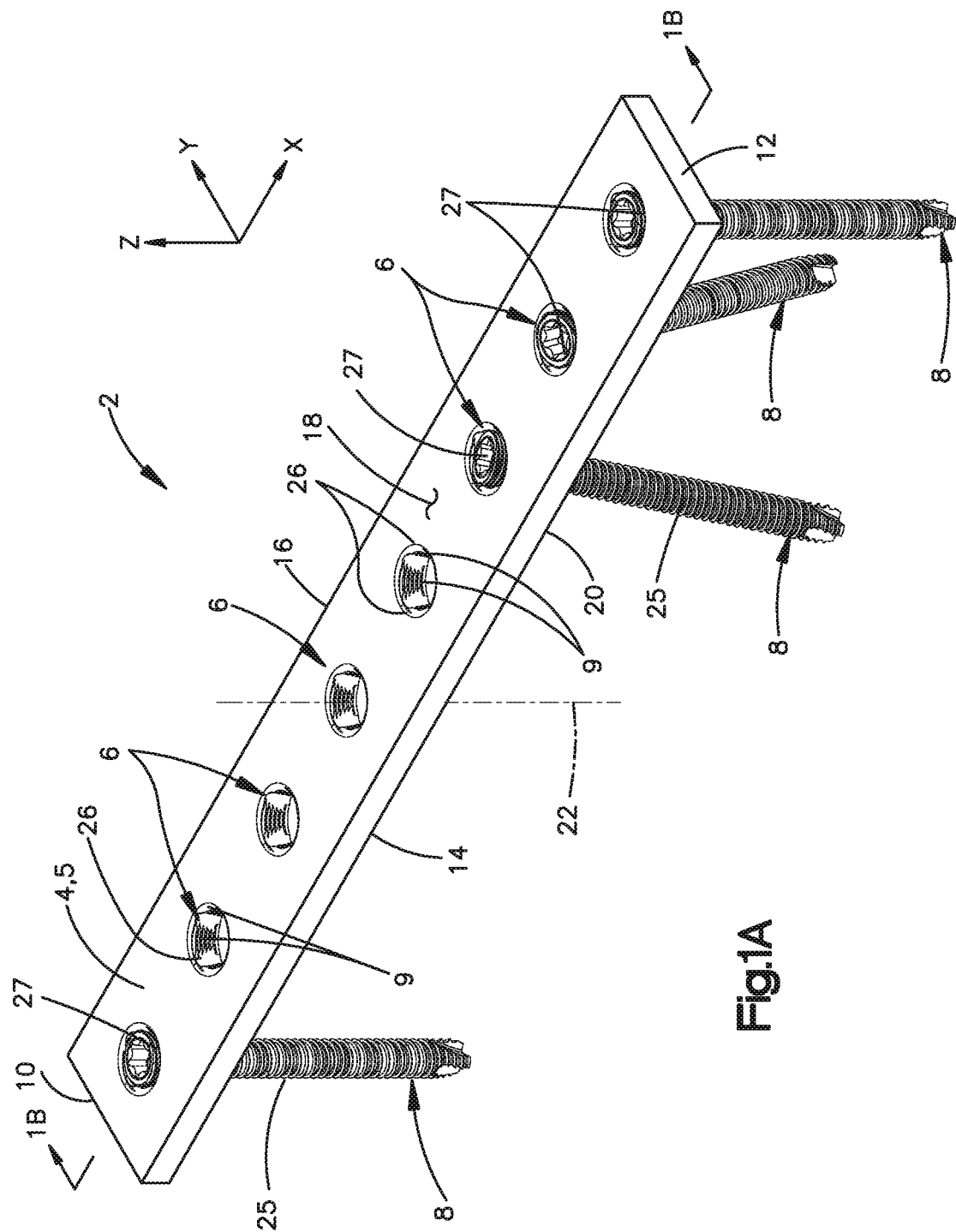
FIG. 1A is a perspective view of a bone fixation system that includes a bone plate and a plurality of locking screws disposed within locking holes of the bone plate, according to an embodiment of the present disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately" and "substantially", as used herein with respect to dimensions, angles, and other geometries, takes into account manufacturing tolerances. Further, the terms "approximately" and "substantially" can include 10% greater than or less than the stated dimension or angle. Further, the terms "approximately" and "substantially" can equally apply to the specific value stated.

Variable angle (VA) locking screws have a tendency to cause, as well as exhibit, cross-threading within a locking hole in which they are inserted, particularly when the VA locking screw is inserted in the locking hole at an angulated trajectory. Cross-threading of the plate threads can be caused by the external threads on the screw head not fitting within (i.e., interfering with) and thus cross-threading the internal threads of the locking hole. Such thread interference can also cause cross-threading of the external threads of the screw head. Regions of contact between the crests of the screw head threads and portions of the internal threads, particularly at or near the crests of the internal threads at angulation, can be particularly susceptible to cross-threading. Cross-threading is problematic because it reduces the intended interference fit (also referred to as the "form-fit") between the screw head threads and the internal threads of the locking hole, which can reduce stability and mechanical strength at the locked interface between the screw head and the locking hole.

The embodiments disclosed herein pertain to locking structures employed within a locking hole and complimentary locking structures on the head of a locking screw. These complimentary locking structures define mating threads having complimentary geometries that provide enhanced control over the deformation of the mating threads, particularly over the deformation of the internal threads of the locking hole, which will effectively become re-aligned to the screw axis at angulated insertions. Such favorable geometries include the respective cross-sectional profiles (referred to in the art as "thread-forms") of the screw head threads and the plate hole threads. These complimentary geometries and profiles can be collectively characterized as "thread proportions" of the plate and screw threads. One way in which the thread profiles disclosed herein control the thread deformation is by providing the screw head threads with a stronger (e.g., larger) profile and interfacing it against an intentionally more malleable (e.g., thinner) profile of the plate hole threads. Another way in which thread deformation is controlled is by adjusting the edge geometry of the thread profiles, such as at the thread crests, to reduce undesirable mechanical interference at the thread interface at angulated screw orientations. The thread proportions disclosed herein have been shown to avoid or reduce cross-threading at angulated screw insertions, and also when the screw insertion involves "timing error", which is an axial mis-alignment of the screw head threads relative to the plate hole threads. Thus, the threaded locking structures described herein can lock with the heads of VA locking screws at angulation, as well as both VA and standard-type locking screws at nominal orientations, in a manner that inhibits (or at least reduces) cross-threading, or at least substantially causes any cross-threading to occur substantially entirely within the plate threads as an act of plastic and elastic thread deformation. The threaded locking structures described herein have also been demonstrated to increase the overall cantilever strength at the locking thread interface.

Referring to FIG. 1A, a bone fixation system 2 includes a bone plate 4 having a plate body 5 that defines therein one or more fixation holes, such as variable-angle (VA) locking holes 6. The VA locking holes 6 are configured to receive anchor members, such as locking screws 8, for example, that are configured to affix the bone plate 4 to one or more portions of bone. The plate body 5 defines internal threads 9 within the VA locking holes 6. Accordingly, the internal threads 9 can also be referred to as "plate hole threads" or simply "plate threads" or "hole threads." The plate threads 9 traverse locking structures, such as columns 26, defined within the VA locking holes 6. Thus the columns 26 can be referred to as "threaded columns". The threaded columns 26 are configured such that, during insertion of a locking screw 8 within the VA locking hole 6, a screw shaft 25 of the locking screw 8 bypasses the columns 26, which in turn engage external threads 29 on the screw head 27 of the locking screw 8 in a manner providing enhanced locking engagement between the locking screw 8 and the bone plate 4, as set forth in more detail below.

The bone plate 4 can be a bridge plate, as shown, although other bone plate types and configurations are within the scope of the present disclosure. The plate body 5 can define a first end 10 and a second end 12 spaced from each other along a longitudinal direction X and a first lateral side 14 and a second lateral side 16 spaced from each other along a lateral direction Y that is substantially perpendicular to the longitudinal direction X. The bone plate 4 can also define an upper plate surface 18 configured to face away from the bone and an opposed lower plate surface 20 configured to face the bone. The upper and lower plate surfaces 18, 20 are spaced from each other along a vertical direction Z substantially perpendicular to each of the longitudinal direction X and the lateral direction Y. It is to be appreciated that, as used herein, the terms "longitudinal", "longitudinally", and derivatives thereof refer to the longitudinal direction X; the terms "lateral", "laterally", and derivatives thereof refer to the lateral direction Y; and the terms "vertical", "vertically", and derivatives thereof refer to the vertical direction Z.

The VA locking holes 6 extend from the upper plate surface 18 to the lower plate surface 20 along a central hole axis 22. The central hole axis 22 is oriented along an axial hole direction. As used herein, the term "axial direction" (e.g., "axial hole direction" and "axial screw direction") is defined as the direction along which the respective axis extends. Furthermore, the directional terms "axial", "axially", and derivatives thereof refer to the respective axial direction. Thus, as used herein, the directional term "axially upward" and derivatives thereof refers to the axial hole direction from the lower plate surface 20 toward the upper plate surface 18. Conversely, the term "axially downward" and derivatives thereof refers to the axial hole direction from the upper plate surface 18 toward the lower plate surface 20. Thus, "axially upward" and "axially downward" are each mono-directional components of the "axial direction", which is bi-directional. In the embodiments depicted in the Figures, the axial hole direction (and thus also the central hole axis 22) is oriented along the vertical direction Z. Accordingly, the axial hole direction is also denoted by "Z" throughout this disclosure. It should be appreciated, however, that the scope of the present disclosure covers embodiments in which the axial hole direction (and thus also the central hole axis 22) is offset from the vertical direction Z at an oblique angle. It should also be appreciated that when the terms "axially upper", "axially lower," and the like are used with reference to the VA locking screw 8, such terms refer to a central axis 23 of the screw 8, particularly as it would be oriented within the VA locking hole 6.

The plate body 5 and the locking screws 8 can each comprise one or more biocompatible materials. By way of non-limiting examples, the plate body 5 can be formed of a material selected from a group comprising: metal, such as titanium, titanium alloys (e.g., titanium-aluminum-niobium (TAN) alloys, such as Ti-6Al-7Nb, and titanium-aluminum-vanadium (TAV) alloys such as Ti-6Al-4V, titanium molybdenum alloys (Ti—Mo) or any other molybdenum metal alloy, and nickel-titanium alloys, such as nitinol), stainless steel, and cobalt base alloys (e.g., cobalt-chrome alloys); composite materials; polymeric materials; ceramic materials; and/or resorbable materials, including resorbable versions of the foregoing material categories (metals, composites, polymers, ceramics). Also by way of non-limiting examples, the locking screws 8 can be formed of a material selected from a group comprising: metal, such as titanium, titanium alloys (e.g., TAN alloys, TAV alloys, such as Ti-6Al-4V, titanium molybdenum alloys (Ti—Mo) or any other molybdenum metal alloy, and nickel-titanium alloys, such as nitinol), stainless steel, cobalt base alloys (e.g., cobalt-chrome alloys); composite materials; polymeric materials; ceramic materials; and/or resorbable materials, including resorbable versions of the foregoing material categories (metals, composites, polymers, ceramics). Preferably, the material of the locking screw 8 has a hardness that is greater than that of the material of the plate body 5. This parameter contributes to the locking characteristics described throughout the present disclosure. Preferably, the plate body 5 primarily or entirely comprises titanium and the locking screws 8 primarily or entirely comprise TAN. It should be appreciated, however, that other material compositions of the bone plates 4 and/or the locking screws 8 are within the scope of the present disclosure.

Moreover, surfaces of the plate body 5 and/or the locking screws 8 can optionally be subjected to one or more processes, such as coating, treating, and/or finishing processes, which can be performed to provide such surfaces, or the underlying subject body material, with certain characteristics, such as to adjust hardness, softness, and/or friction parameters of the body material. Non-limiting examples of coatings include DLC, TiN, AlTiN and other coatings that provide, among other things, lubrication, a coefficient of friction different than that of the underlying material, and/or a surface hardness different than that of the underlying material. Non-limiting examples of surface treatments include processes for hardening outer surfaces of the body material, such as hard anodization and diffusion hardening, the latter of which can include diffusing nitrogen, oxygen, carbon, and/or zirconium into the plate body 5 and/or locking screw 8 surfaces. Additional or alternative surfaces treatments can include annealing or other processes for softening the body material, particularly the plate body 5 material, though such softening processes can also be employed on the screw 8 body material. The foregoing processes can be employed, for example, to provide beneficial thread deformation performance at the thread interface, as described throughout the present disclosure, and/or to allow mating thread surfaces to effectively slide against one another with less friction and thus less unwanted deformation. It should be appreciated that the plate body 5 and the locking screws 8 can be subjected to different processes. Moreover, either or each of the plate body 5 and locking screws 8 need not be subjected to any of the foregoing processes.

Furthermore, the dimensions set forth throughout this disclosure are made in reference to bone fixation systems 2 that includes at least one VA locking hole 6 and at least one VA locking screw 8 configured for nominal or angulated insertion within the at least one VA locking hole 6, in which the screw shaft 25 of the VA locking screw 8 defines a major diameter in a range of about 0.5 mm to about 10.0 mm, more particularly in a range of about 1.0 mm to about 7.0 mm, more particularly in a range of about 2.0 mm to about 4.0 mm, and more particularly a major diameter of about 3.5 mm. The foregoing screw shaft 25 sizes can correspond to the threaded head 27 defining a major diameter in a range of about 0.7 mm to about 15.0 mm, more particularly in a range of about 1.0 mm to about 12.0 mm, more particularly in a range of about 2.0 mm to about 10.0 mm, and more particularly in a range of about 3.0 mm to about 7.0 mm. It is to be appreciated, however, that any of the embodiments described below can be scaled upward or downward in size as needed for employment within larger or smaller bone fixation systems.

Figure 1B:
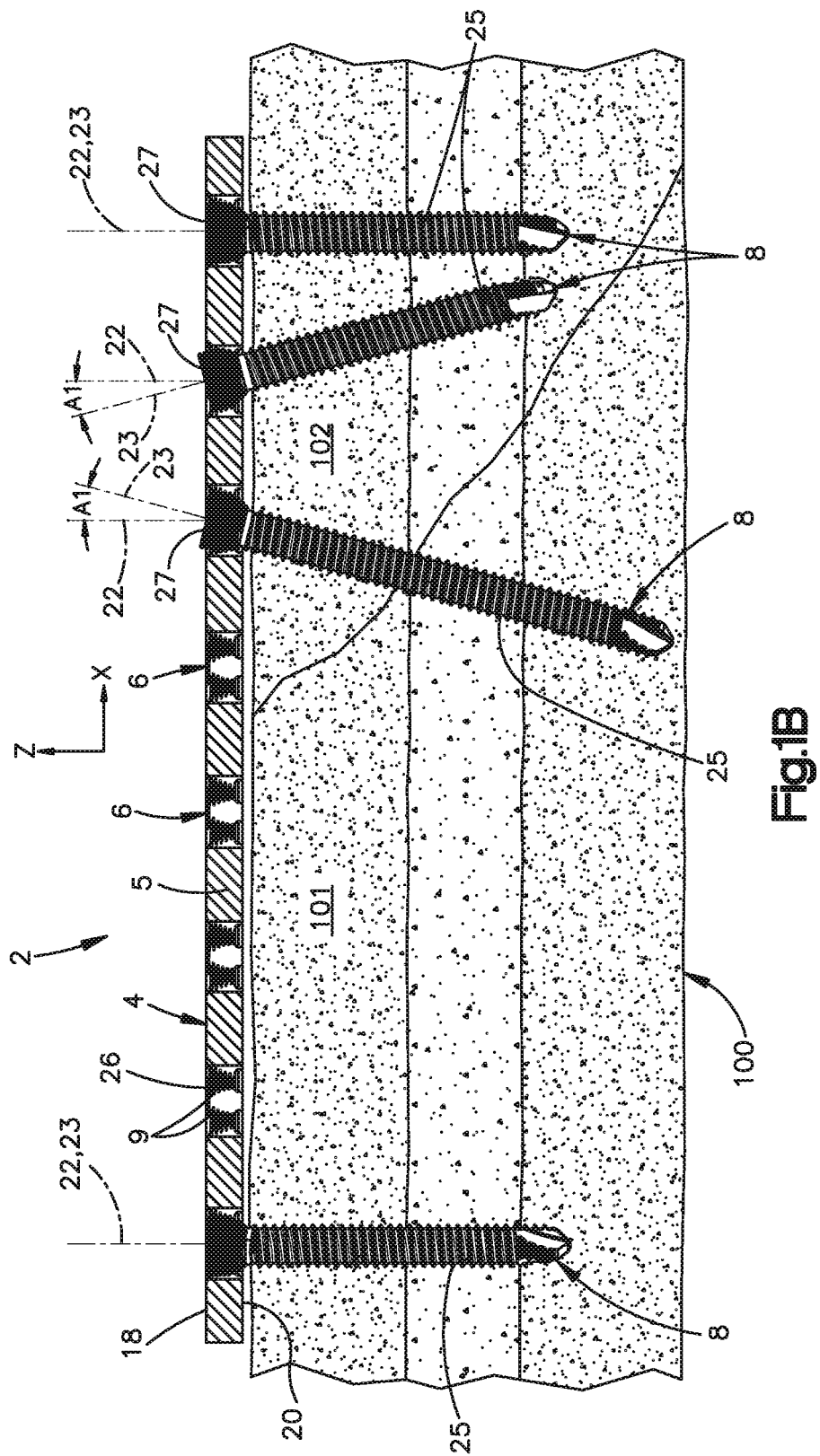
FIG. 1B is a sectional side view of the bone fixation system taken along section line 1B-1B in FIG. 1A affixed to a plurality of bone segments.

Referring now to FIG. 1B, the VA locking holes 6 can be configured to provide enhanced affixation with multiple types of locking screws 8, including VA locking screws 8 as well as standard-type locking screws, including such screws having various lengths, so as to allow a physician to implant the bone plate 4 to one or more bones or bone segments as desired. By way of non-limiting example, as shown, the bone plate 4 can be coupled to a long-bone 100 via locking screws 8 in a manner affixing fractured segments 101, 102 of the bone together. The VA locking holes 6 described herein can lock with VA locking screws 8 or standard-type locking screws at a nominal orientation whereby a central screw axis 23 thereof is substantially aligned with the central hole axis 22. The VA locking holes 6 can also lock with VA locking screws 8 at an angulated orientation whereby the central screw axis 23 is oriented at an acute angle A1 with respect to the respective central hole axis 22. Acute angle A1 can also be referred to as the "angle of angulation" or simply the "angulation." VA locking screws 8 and standard-type locking screws and their locking functionalities are described more fully in U.S. Pat. No. 9,314,284, issued Apr. 19, 2016, in the name of Chan et al. ("the '284 Reference"), and U.S. patent application Ser. No. 15/940,761, filed Mar. 29, 2018, in the name of Bosshard, et al. ("the '761 Reference"), and Ser. No. 15/966,047, filed Apr. 30, 2019, in the name of Bosshard, et al. ("the '047 Reference") the disclosures of each of which are hereby incorporated by reference as if set forth in their entireties herein.

During a bone plating operation, the screw shaft 25 of a locking screw 8 can be inserted through one of the VA locking holes 6 and driven into the underlying bone 100. In particular, rotation of the locking screw 8 causes its threaded screw head 27 to threadedly mate with the VA locking hole 6. As a result, the screw head 27 fastens the bone plate 4 to the underlying bone 100 substantially without applying a compressive force onto the bone plate 4 against the underlying bone 100. The bone plate 4 can be spaced from the underlying bone 100 when locked to the threaded screw head 27. Alternatively, the bone plate 4 can abut the underlying bone 100 when locked to the threaded screw head 27.

It is to be appreciated that, during a plating operation, the first locking screw 8 inserted through one of the VA locking holes 6 and into underlying bone 100 has the benefit of being able to generally mate with the plate threads 9 so that crests of the screw head thread 29 advance helically substantially along the roots of the plate threads 9. However, once the first locking screw 8 is locked to the bone plate 4 thereby fastening the plate 4 to the underlying bone 100, the subsequent locking screws 8 often lack the ability to have their external thread crests advance helically along the plate thread 9 roots. This results because, once the screw shafts 25 of these subsequent locking screws 8 advance through the VA locking holes 6 and threadedly purchase into the underlying bone 100, the relative axial positions of the screw head threads 29 and the plate threads 9 are substantially a function of the screw's threaded purchase with the underlying bone 100. This axial misalignment of the screw head threads 29 relative to the plate threads 9 is referred to herein as "timing error."

Referring now to FIGS. 2A through 2C and 2E, each of the VA locking holes 6 can be defined by an interior surface 24 of the plate body 5. Alternatively, the interior surface 24 can be defined by an insert plate body 5a, which can also be referred to an "insert" or "inlay", that is fitted within an axial aperture or receptacle 95 of the plate body 5, as indicated in dashed lines in FIG. 2E. It should be appreciated that the bone fixation system 2 can include a plurality of interchangeable inserts 5a having different hole 6 shapes and geometries and/or different thread parameters, each being insertable within the receptacle 95, such that the physician can select the particular insert 5a having the desired VA locking hole 6 geometry, as needed. Typically, at least a portion of the interior surface 24 is tapered as it extends axially downward. Thus, the interior surface 24 is configured to prevent the screw head 27 from passing completely through the VA locking hole 6.

The interior surface 24 can define the threaded columns 26. The columns 26 extend axially between the upper and lower plate surfaces 18, 20. Within each (or at least some of) the VA locking holes 6, the columns 26 are sequentially located about a circumference of the interior surface 24. The interior surface 24 also defines a plurality of recesses 28 sequentially located circumferentially between the columns 26. The recesses 28 extend axially between the upper and lower plate surfaces 18, 20. The columns 26 and recesses 28 can be evenly spaced about the circumference of the interior surface 24 within the VA locking hole 6. However, in other embodiments, the columns 26 and/or recesses 28 can be un-evenly spaced about the circumference of the VA locking hole 6.

The plate threads 9 extend through the columns 26 and at least portions of the recesses 28 along one or more thread paths between the upper and lower plate surfaces 18, 20. As shown, the one or more thread paths can include a pair of non-intersecting thread paths (i.e., double-lead); however in other embodiments the one or more thread paths can include a single thread path (i.e., single-lead), or three or more thread paths (e.g., triple-lead, etc.). The thread paths are preferably helical, although other thread path types are within the scope of the present disclosure. As shown, portions of the recesses 28 can circumferentially interrupt the plate threads 9. Stated differently, the plate threads 9 can "bottom-out" along one or more and up all of the recesses 28. In other embodiments, however, the plate threads 9 can circumferentially traverse one or more and up to each of the recesses 28 in an uninterrupted fashion (i.e., the plate threads 9 need not bottom-out in the recesses 28).

The plate threads 9 have a cross-sectional profile in a reference plane that extends along the central hole axis 22. Such as cross-sectional profile is also referred to as a "thread-form," and includes crests 56, roots 58, and upper and lower flanks 55, 57 that extend between the crests 56 and roots 58, as shown in FIG. 2B. As used herein with reference to the plate threads 9, the term "crest" refers to the apex of a fully-developed thread-form. Each threaded column 26 defines one or more thread segments 52 extending along the thread path(s). As used herein, the term "thread segment" refers to any portion of a thread, such as the plate threads 9 and the screw head threads 29, that has a thread-form and a length along its thread path. The thread segments 52 of the plate threads 9 can also be referred to herein as "plate thread segments" 52. Plate thread segments 52 that traverse a column 26 can be referred to herein as "column threads" 54.

The interior surface 24 can define an upper perimeter 30 of the VA locking hole 6 at an interface with the upper plate surface 18 and a lower perimeter 32 of the VA locking hole 6 at an interface with the lower plate surface 20. The upper and lower perimeters 30, 32 can each be circular in shape, although other shapes are within the scope of the present disclosure, as discussed in more detail below. The interior surface 24 can also define one or more lead-in surfaces 34 that taper axially downward from the upper perimeter 30 to one or more of the columns 26. As shown, the one or more lead-in surfaces 34 can include a single lead-in surface 34 can be circumferentially interrupted by one or more of the recesses 28. Alternatively, the lead-in surface 34 can extend circumferentially continuously and uninterrupted along a full revolution about the central hole axis 22. The interior surface 24 can also define an undercut surface 36 that tapers axially upward from the lower perimeter 32. The undercut surface 36 can extend circumferentially continuously and uninterrupted along a full revolution about the central hole axis 22. Alternatively, the undercut surface 36 can be circumferentially interrupted by one or more of the recesses 28.

Figure 2A:
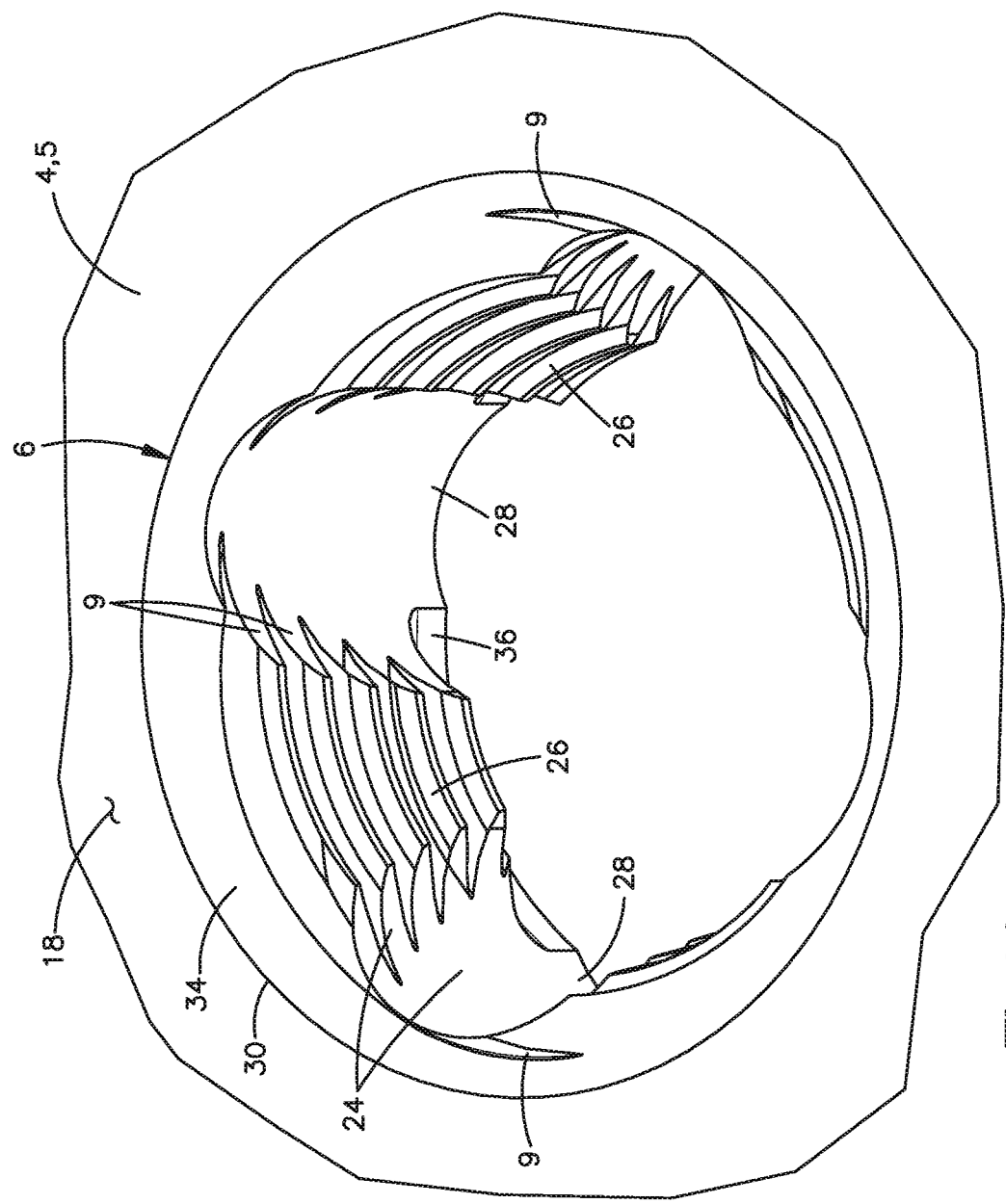
FIG. 2A is a perspective view of a locking hole of the bone plate illustrated in FIGS. 1A and 1B.
Figure 2C:
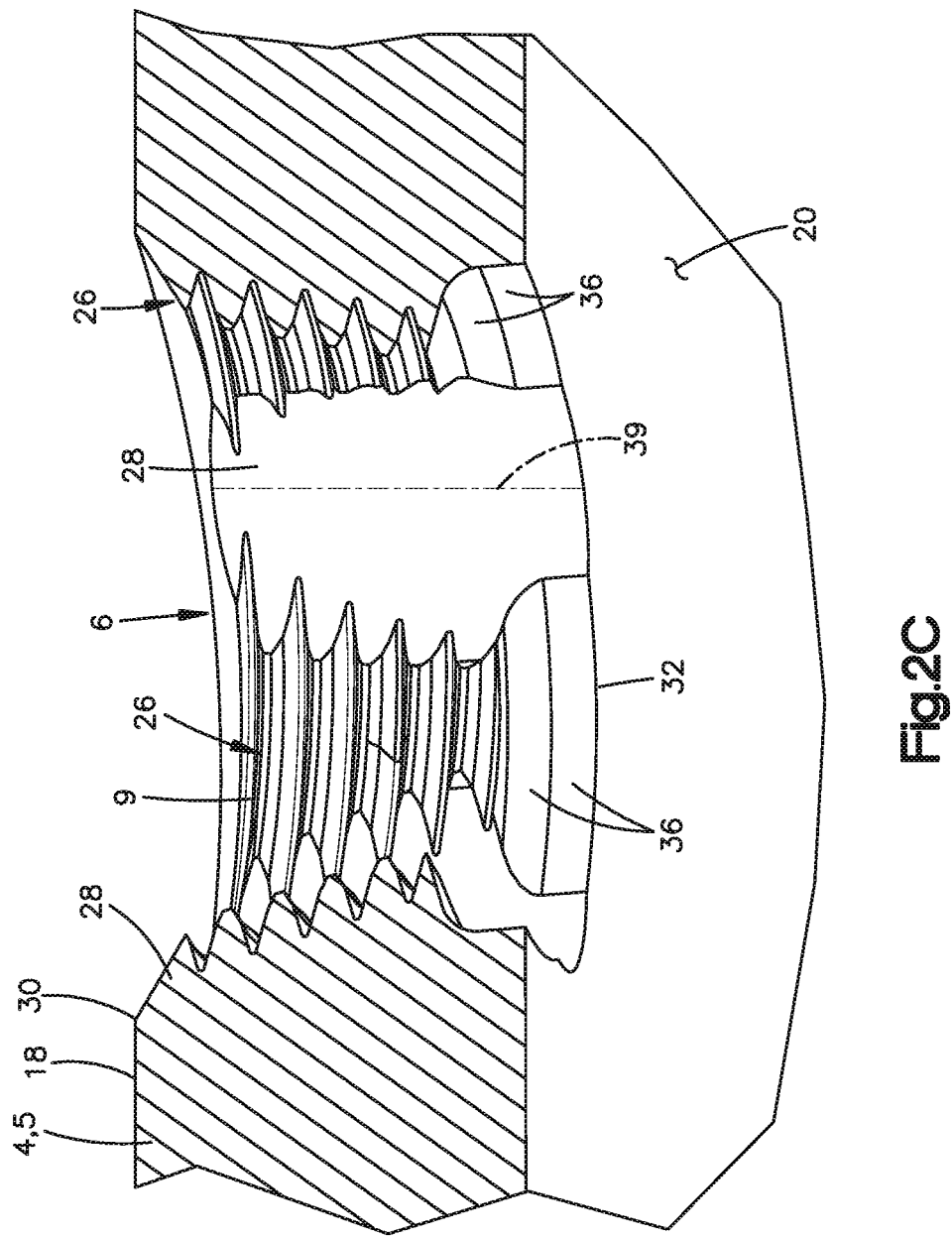
FIG. 2C is another sectional perspective view of the locking hole illustrated in FIG. 2A.
Figure 2D:
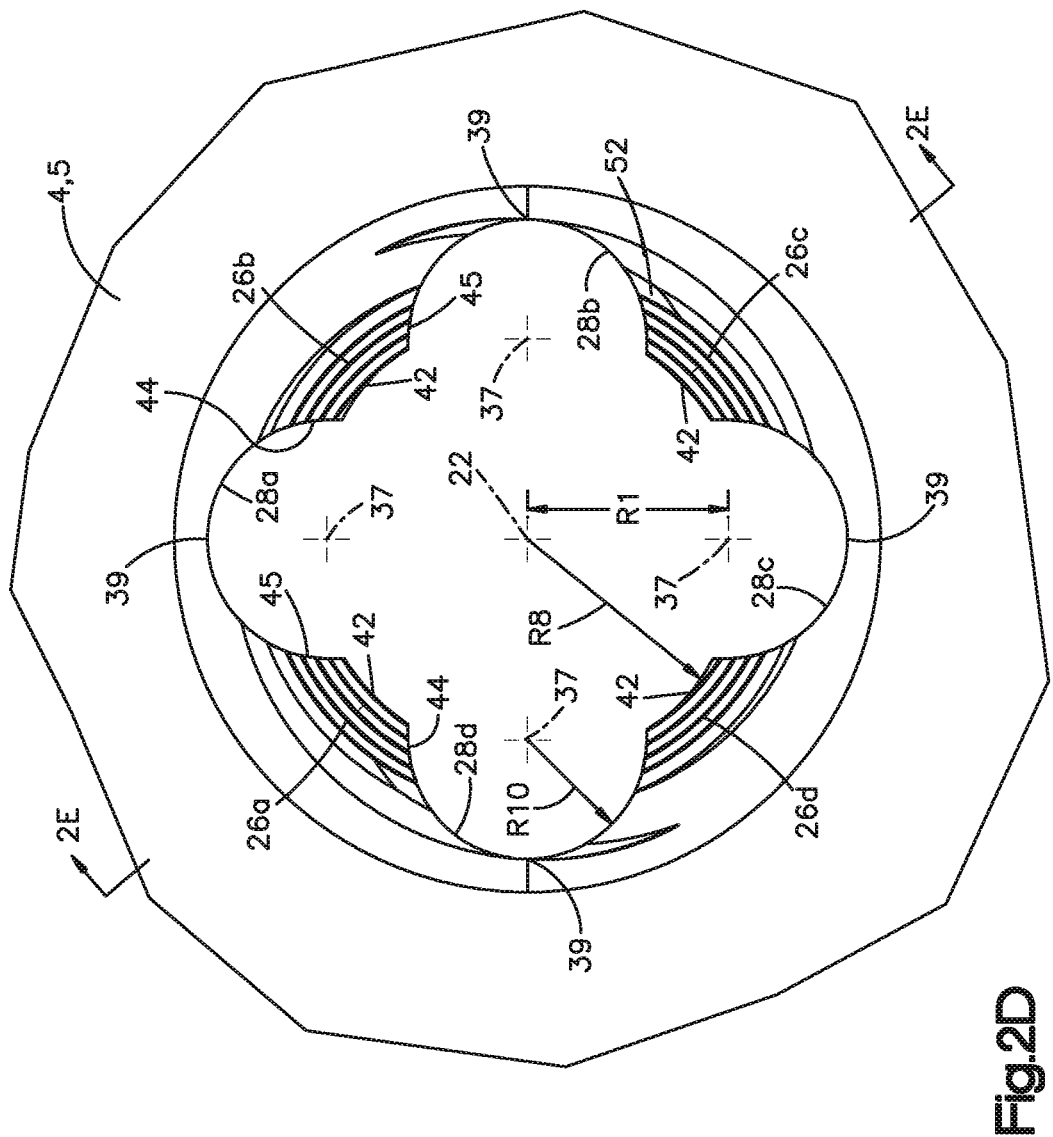
FIG. 2D is a top view of the locking hole of FIG. 2A.

Referring now to FIG. 2D, in an example embodiment, the VA locking hole 6 can include four (4) columns 26 and four (4) recesses 28 evenly spaced about the central hole axis 22. The columns 26 can include a first column 26a, a second column 26b, a third column 26c, and a fourth column 26d evenly spaced about the central hole axis 22. The recesses 28 can include: a first recess 28a located circumferentially between the first and second columns 26a, 26b; a second recess 28b located circumferentially between the second and third columns 26b, 26c; a third recess 28c located circumferentially between the third and fourth columns 26c, 26d, and a fourth recess 28d located circumferentially between the fourth and first columns 26d, 26a. It should be appreciated that the design of the VA locking hole 6 is not limited by the number of columns 26 and recesses 28, as described in more detail below.

Each of the recesses 28a-d can define a central recess axis 37, each of which can be parallel with the central hole axis 22, although other central recess axis 37 orientations are possible. Each central recess axis 37 can also be radially spaced from the central hole axis 22 by radial distance R1. Each recess defines a recess radius R10. As shown, each of the recesses 28a-d has a horizontal profile (i.e., a profile in a reference plane orthogonal to the central hole axis 22) that subsumes about half of a circle. In the illustrated embodiment, each of the recesses 28a-28d is generally shaped as a section of a cylinder. In other embodiments, one or more an up to all of the recesses can have a downward-tapering frusto-conical shape. Other recess shapes are also within the scope of the present disclosure. Each recess 28 defines a radially-outermost region or apex 39, as measured from the central hole axis 22. Each recess apex 39 can extend along a plane, along which the central hole axis 22 also extends. In the depicted embodiments, the recess apices 39 are parallel with the central hole axis 22. In other embodiments, the recess apices 39 can be oriented at an acute angle relative to the central hole axis 22.

Each column 26 can define a first surface 42 substantially facing the central hole axis 22. The first surface 42 can also be referred to as an "innermost surface" of the column 26. Thus, the first surface 42 defines the crests 56 of the column threads 54. In a horizontal reference plane (such as reference plane M shown in FIG. 2E), the first surface 42 of each column 26 preferably extends arcuately about the central hole axis 22 and defines a shared or common radius R8. The first surface 42 of each column 26 can also extend between a first side 44 and a circumferentially opposed second side 45 of the column 26. The first and second sides 44, 45 of each column 26 can define interfaces between the column 26 and the circumferentially adjacent recesses 28. For example, the first side 44 of the first column 26a can define an interface between the first column 26a and the fourth recess 28d; the second side 45 of the first column 26a can define an interface between the first column 26a and the first recess 28a; the first side 44 of the second column 26b can define an interface between the second column 26b and the first recess 28a; the second side 45 of the second column 26b can define an interface between the second column 26b and the second recess 28b; and so forth along the circumference of the interior surface 24. The first surfaces 42 of the columns 26 can collectively define circumferential segments of a downward-tapering frusto-conical shape, particularly one that defines a central cone axis coincident with the central hole axis 22.

Figure 2E:
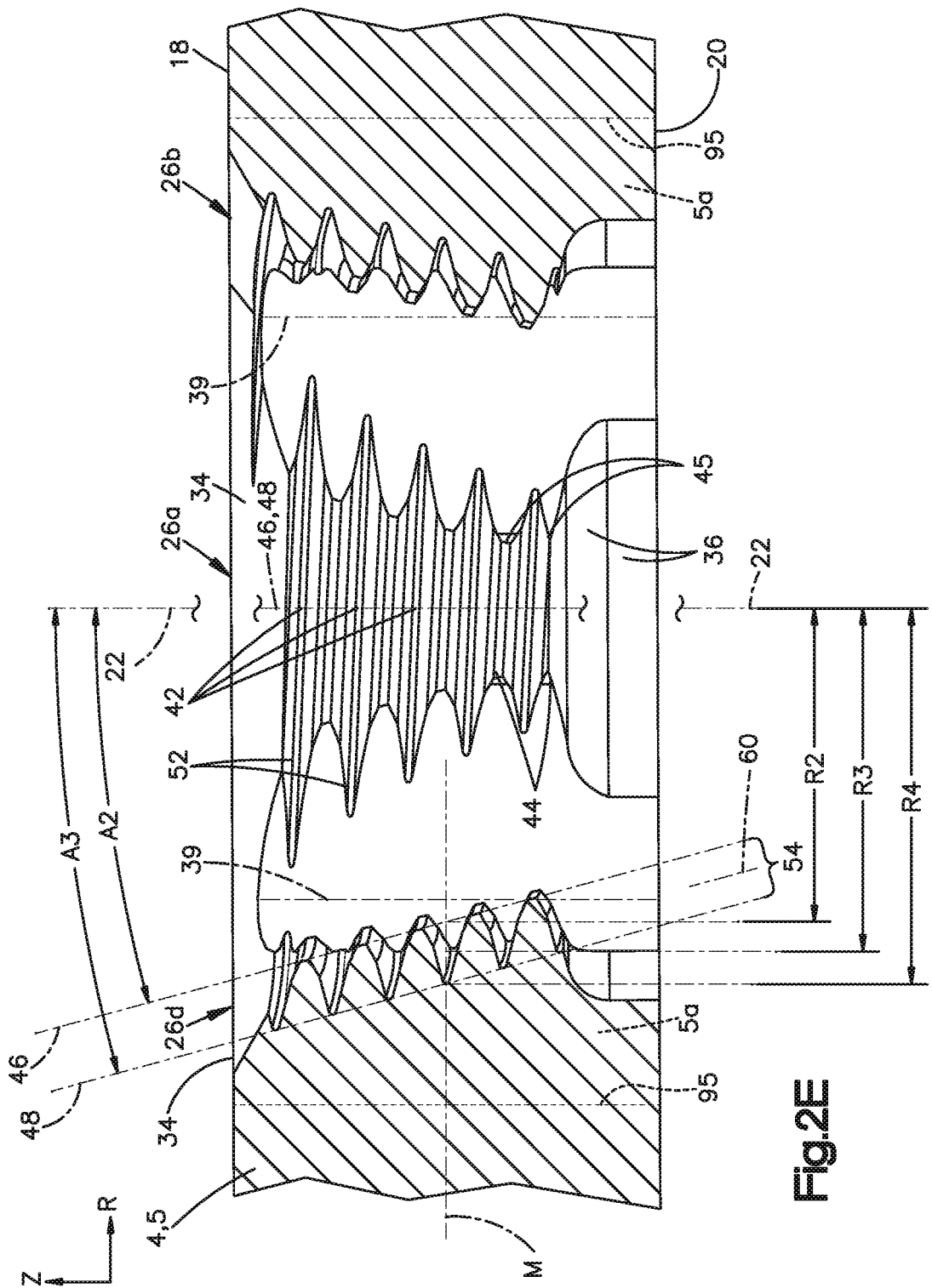
FIG. 2E is a side sectional view of the locking hole taken along section line 2E-2E illustrated in FIG. 2D, showing a threaded locking structure defined by an interior surface of the locking hole, wherein the threaded locking structure is configured to lock with a locking bone screw.
Figure 2F:
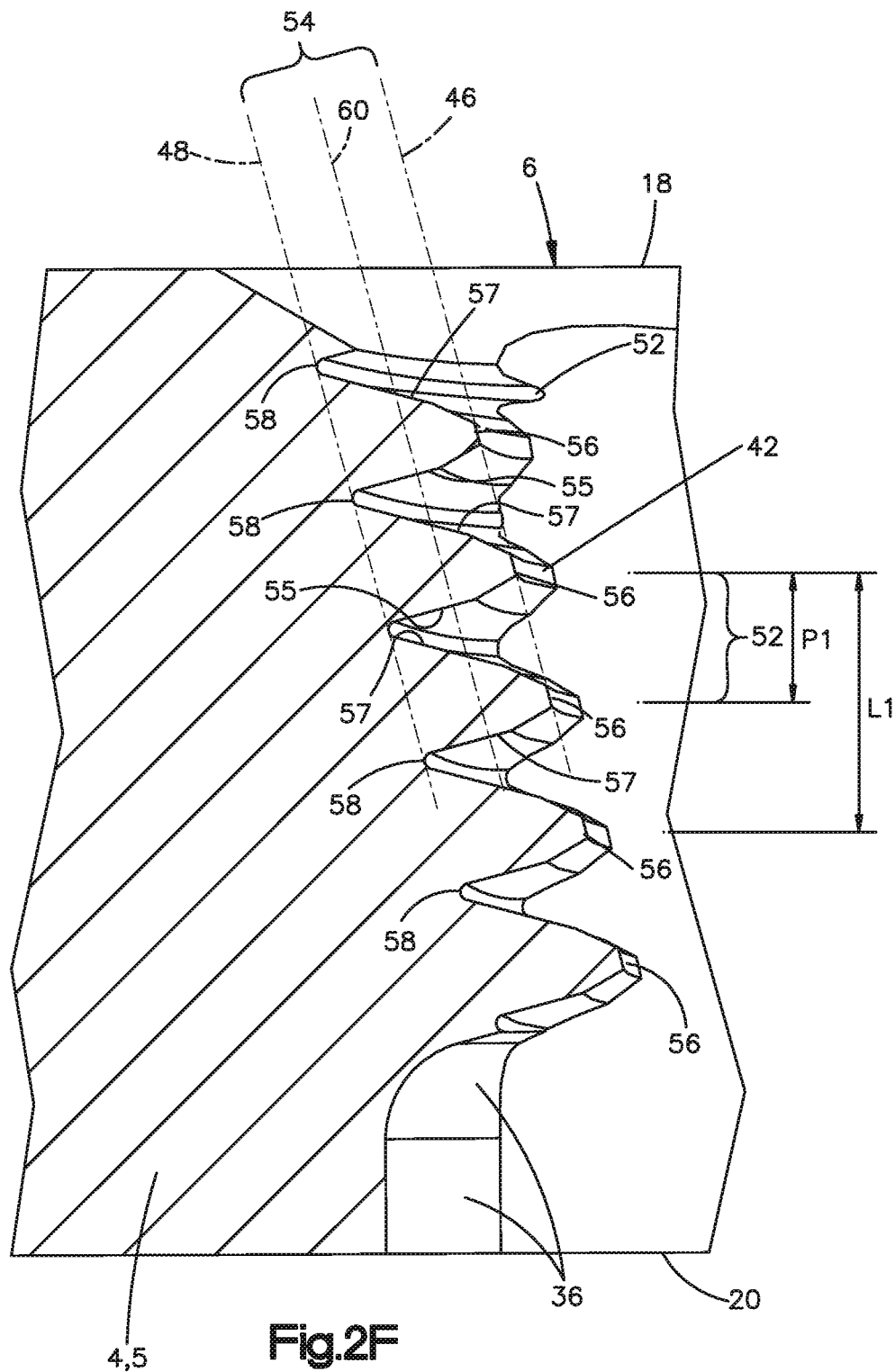
FIG. 2F is an enlarged sectional view of the threaded locking structure shown in FIG. 2E.

With reference to FIG. 2E, each column 26 can define a crest centerline 46 that is disposed circumferentially equidistantly between the first and second sides 44, 45 of the column 26. In each column 26, the crest centerline 46 extends along the first surfaces 42 and thus intersects the crests 56 of the column threads 54. The crest centerline 46 of each column 26 is coplanar with the central hole axis 22 in a respective axial reference plane. In this manner, each crest centerline 46 also defines a crest trajectory of the column threads 54 in the axial reference plane. Accordingly, the crest centerline 46 can also be referred to as a "crest trajectory axis" 46. Each column 26 can also define a root centerline 48 that is disposed circumferentially equidistantly between the first and second sides 44, 45 of the column 26. In each column 26, the root centerline 48 intersects the roots 58 of the column threads 54. The root centerline 48 of each column 26 is coplanar with the crest centerline 46 and the central hole axis 22 in the respective axial reference plane. In this manner, each root centerline 48 also defines a root trajectory of the column threads 54 in the axial reference plane. Accordingly, the root centerline 48 can also be referred to as a "root trajectory axis" 48. The crest trajectory axis 46 can be oriented at an acute angle A2 relative to the central hole axis 22. The root trajectory axis 48 can also be oriented at an acute angle A3 relative to the central hole axis 22. Acute angles A2 and A3 can be in a range of about 5 degrees to about 30 degrees. In additional embodiments, the angles A2, A3 can be in a range of about 10 degrees to about 20 degrees, and can further be in a range of about 13 degrees to about 17 degrees. The crest and root trajectory axes 46, 48 are preferably parallel, as shown. In other embodiments, however, the crest and root trajectory axes 46, 48 of one or more and up to all of the columns 26 can be oriented at an acute angle relative to one another, as described in the '761 Reference. The column threads 54 can also define a thread midline 60, which can lie in the common plane with the crest and root trajectory axes 46, 48 and the central hole axis 22, as also shown in FIG. 2F. The thread midline 60 is equidistantly spaced between the crest and root trajectory axes 46, 48.

The crest trajectory axis 46 can be radially spaced from the central hole axis 22 by a distance R2 measured along a reference plane M that is orthogonal to the central hole axis 22 and located at the vertical center of the VA locking hole 6. Thus, the reference plane M can be characterized as the axial "mid-plane" of the VA locking hole 6. The thread midline 60 can be radially spaced from the central hole axis 22 by a distance R3 measured along the hole mid-plane M. The root trajectory axis 48 can be radially spaced from the central hole axis 22 by a distance R4 measured along the hole mid-plane M. Distance R2 can be characterized as the mean crest radius of the column threads 54. Distance R3 can be characterized as the mean radius of the column threads 54. Distance R4 can be characterized as the mean root radius of the column threads 54. It should be appreciated that any of the mean crest radius R2, the mean radius R3, and the mean root radius R4 can optionally be used as a metric for categorizing the size of the hole 6.

Referring now to FIG. 2F, each plate thread segment 52, as an internal thread, can be axially centered at the root 58, and includes the upper flank 55 extending from the root 58 to the axially upward crest 56, and also includes the lower flank 57 extending from the root 58 to the axially lower crest 56. Each plate thread segment 52 is configured to intermesh with (i.e., at least partially house) at least one associated thread segment of the screw head threads 29, as described in more detail below. The plate threads 9 define a thread pitch P1 that extends between axially adjacent crests 56 along the axial direction. The plate threads 9 also define a thread lead L1, which can also be defined at the crests 56. The thread pitch P1 of the column threads 54 can be in a range of about 0.05 mm to about 5.0 mm, more particularly in a range of about 0.05 mm to about 2.0 mm, more particularly in a range of about 0.1 mm to about 1.5 mm, more particularly in ranges of about 0.2 mm to about 1.0 mm, about 0.3 mm to about 0.8 mm, about 0.4 mm to about 0.6 mm, about 0.15 mm to about 0.6 mm, and preferably about 0.4 mm. The thread lead L1 can be in a range of 0.05 mm to about 5.00 mm, about 0.05 mm to about 2.0 mm, about 0.1 mm to about 1.5 mm, about 0.2 mm to about 1.0 mm, about 0.3 mm to about 0.8 mm, about 0.4 mm to about 0.6 mm, about 0.3 mm to about 1.2 mm, about 0.15 mm to about 0.6 mm, about 0.4 mm, and preferably about 0.8 mm. It should be appreciated that in embodiments where the plate threads 9 are double-lead threads, such as those depicted, the thread lead L1 is twice the distance of the thread pitch P1 (i.e., L1=2×P1). In embodiments where the plate threads 9 are single-lead threads, the thread lead L1 and thread pitch P1 are equivalent to each other. In embodiments where the plate threads 9 are triple-lead threads, the thread lead L1 is three-times the distance of the thread pitch P1 (i.e., L1=3×P1). Thus, the thread "lead" factor is a multiple by which the thread lead L1 is measured relative to the thread pitch P1.

Figure 2G:
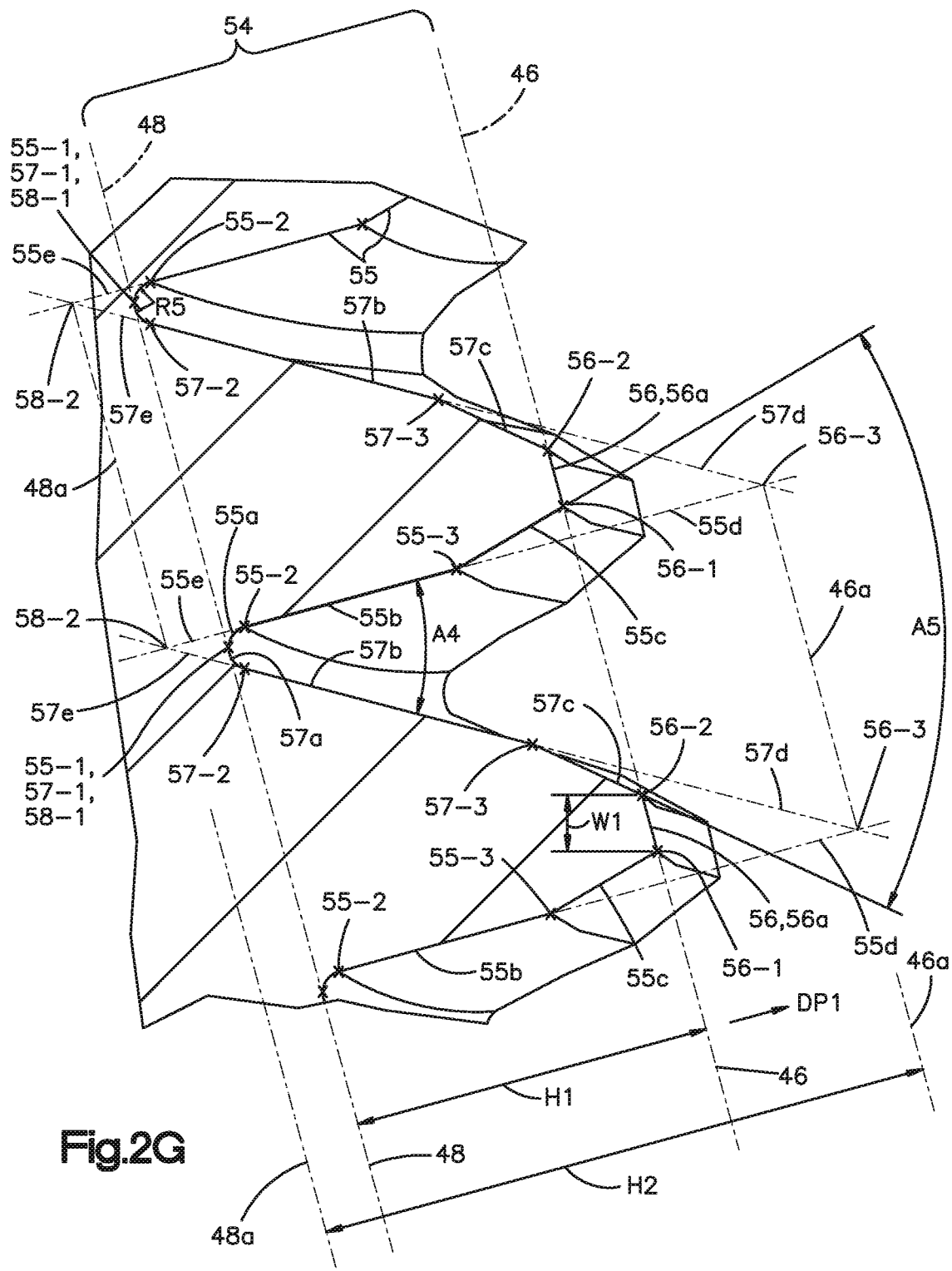
FIG. 2G is a further enlarged section view of a portion of the threaded locking structure shown in FIG. 2F.

Referring now to FIG. 2G, the cross-sectional profiles (i.e., thread-forms) of the plate threads 9 in the axial reference plane will now be described. These cross-sectional profiles can also be referred to herein simply as "thread profiles". In the illustrated embodiment, this reference plane also contains the root trajectory axis 48. The thread profiles of the plate threads 9 are substantially similar in each of the respective axial reference planes of the various thread columns 26. As described above, these thread profiles, and the edge geometries thereof, are configured to be complimentary with those of the screw head threads 29 to provide favorable mating engagement therebetween, such as for controlling thread deformation of, and/or reducing undesirable mechanical interference between, the plate threads 9 and the screw head threads 29.

The first and second flanks 55, 57 are offset from one another at an angle A4, which defines the thread angle of the plate threads 9. Accordingly, angle A4 can also be referred to as "thread angle" A4 of the plate threads 9 or the "plate thread angle" A4. In the illustrated embodiment, the crests 56 of the plate thread segments 52 are truncated for reducing undesirable mechanical interference with the screw head threads 29. Additionally, the first and second flanks 55, 57 can be offset from one another at a plurality of angles. For example, in the illustrated embodiment, upper and lower flanks 55, 57 of the plate thread segments 52 are also truncated adjacent the crests 56 in a manner providing the plate thread segments 52 with a second thread angle A5 adjacent the crests 56. The plate threads 9 of such an embodiment can be referred to as "dual-angle" threads. It should be appreciated that the flanks 55, 57 of the plate thread segments 52 can define yet additional thread angles, such as a third thread angle, a fourth thread angle, etc. In such multi-angle embodiments, including dual-angle embodiments, thread angle A4 can be referred to as a "first thread angle" A4. In yet further embodiments, the flanks 55, 57 (or at least portions thereof) can have arcuate profiles, which can theoretically define an infinite number of thread angles. The particular edge geometries of the thread profiles defined by the truncated crests and truncated flanks 55, 57 are described in more detail below.

In each plate thread segment 52, the root 58 defines a root profile, the crests 56 define crest profiles, and the upper and lower flanks 55, 57 define respective upper and lower flank profiles. In the illustrated embodiment, and with reference to a radially inward direction, the profile of the upper flank 55 includes:

a) a first upper flank portion 55a that extends from a first upper flank reference point 55-1 to a second upper flank reference point 55-2;

b) a second or "primary" upper flank portion 55b that extends along a consistent geometry from the second upper flank reference point 55-2 to a third upper flank reference point 55-3; and c) a third upper flank portion 55c that extends from the third upper flank reference point 55-3 to a lower crest reference point 56-1.

Similarly, in the illustrated embodiment, and with reference to the radially inward direction, the profile of the lower flank 57 includes:

a) a first lower flank portion 57a that extends from a first lower flank reference point 57-1 to a second lower flank reference point 57-2;

b) a second or primary lower flank portion 57b that extends along a consistent geometry from the second lower flank reference point 57-2 to a third lower flank reference point 57-3; and c) a third lower flank portion 57c that extends from the third lower flank reference point 57-3 to an upper crest reference point 56-2.

The first upper and lower flank portions 55a, 57a are coincident with each other and with a root reference point 58-1, which is located at the root 58 (i.e., the location of the thread segment 52 spaced furthest from the crest trajectory axis 46). Additionally, the first upper and lower flank portions 55a, 55b can each define a relief surface extending from the root 58. As shown, the first upper and lower flank portion 55a, 57a can each be arcuate and can define a shared or common relief radius R5, which is configured to reduce stress concentrations at the root 58. Thus, the first upper and lower flank portion 55a, 57a can be referred to as respective "root relief" portions 55a, 57a of the upper and lower flanks 55, 57. Because the root relief portions 55a, 57a of the illustrated embodiment have a common boundary at the first root reference point 58-1, the root 58 profile of each thread segment 52 substantially consists of a single point in the axial reference plane. In other embodiments, however, the root 58 can define an elongated root profile, which can extend linearly between the first upper and lower flank reference points 55-1, 57-1 along the root trajectory axis 48 (as described in more detail below with reference to the embodiment shown in FIGS. 5B and 5C).

The primary upper and lower flank portions 55b, 57b each extend along a consistent geometry in the axial reference plane. As used herein, the term "consistent geometry" means a line, a regular curve, or a portion of a non-regular curve which portion does not include an inflection and does not backtrack on itself. Non-limiting examples of such curves having a consistent geometry include an involute curve, as more fully described in the '047 Reference, and a curve having a constant, relatively large radius. In the illustrated embodiment, the primary flank portions 55b, 57b extend linearly and define the first thread angle A4. Additionally, the third upper and lower flank portions 55c, 57c of the illustrated embodiment define the second thread angle A5 therebetween and are offset from the respective primary flank portions 55b, 57b. The first thread angle A4 of the plate can be in a range of about 28 degrees to about 32 degrees, and can also be in a range of about 20 degrees to about 40 degrees, and can further be in a range of about 15 degrees to about 50 degrees. The second thread angle A5 of the plate can be in a range of about 53 degrees to about 57 degrees, and can also be in a range of about 45 degrees to about 65 degrees, and can further be in a range of about 40 degrees to about 75 degrees. In other embodiments, the primary flank portions 55b, 57b and the respective third upper and lower flank portions 55c, 57c of any and up to each of the flank profiles need not have a common boundary at the third lower flank reference point 57-3. For example, such flank profiles can include a transition portion, which can be arcuate, extending between the primary flank portions 55$b$, 57$b$ and the respective third upper and lower flank portions 55$c$, 57$c$. In such embodiments, it should be appreciated that the third upper and lower flank reference points 55-3, 57-3 continue to define radially inward ends of the primary flank portions 55$b$, 57$b$.

Furthermore, the thread profiles of the column threads 54 include crest profiles 56$a$ that are truncated. In the illustrated embodiment, the crest profile 56$a$ extends linearly from the lower crest reference point 56-1 to the upper crest reference point 56-2 along the crest trajectory axis 46, which is also linear. This linear crest profile 56$a$ is configured to further reduce stress concentrations at the crest 56. Additionally, each crest profile 56$a$ can define a crest width W1, as measured between the upper and lower crest reference points 56-1, 56-2 along the axial plate direction. Additionally, it should be appreciated that the third upper and lower flank portions 55$c$, 57$c$, which can be characterized as chamfers or bevels, can effectively define relief surfaces for the crest 56, which relief surfaces are configured to further reduce stress concentrations at the crest 56. Thus, the third upper and lower flank portion 55$c$, 57$c$ can be referred to as respective "crest relief" portions of the flank 55, 57 profiles.

It should be appreciated that the foregoing geometries of the plate thread profiles are provided as examples, and that other profile geometries are within the scope of the present disclosure. For example, the crest profile 56$a$ of one or more and up to all of the thread segments 52 in the column 26 can optionally be rounded, radiused, chamfered, and/or beveled, with the crest 56 itself located at the apex of the crest profile 56$a$. Moreover, the root relief portions 55$a$, 57$a$ of the flanks 55, 57 can be linear and can extend to the root 58.

The column threads 54 define a thread height H1 measured from the crests 56 to the roots 58 along a direction DP1 that is perpendicular to the crest trajectory axis 46. In particular, the thread height H1 of any of the plate thread segments 52 can be measured from the crest trajectory axis 46 to the root 58 of the respective thread segment 52 along direction DP1. Alternatively or additionally, the thread height H1 of any of the plate thread segments 52 can be measured from the crest 56 to the root trajectory axis 48 along direction DP1. The thread height H1 of the plate column threads 54 can be in a range of about 0.05 mm to about 2.0 mm, more particularly in a range of about 0.1 mm to about 1.5 mm, more particularly in a range of about 0.2 mm to about 1.0 mm, and more particularly in ranges of about 0.3 mm to about 0.55 mm, about 0.35 mm to about 0.48 mm, and about 0.40 mm to about 0.44 mm, and can also be in a range of about 0.32 mm to about 0.48 mm, and can further be in a range of about 0.20 mm to about 0.55 mm. It is to be appreciated that the thread height H1 of the plate thread segments 52 can be constant along the crests 56 of the column 26.

With continued reference to FIG. 2G, it should be appreciated that the thread profiles of the column threads 54 described above deviate from a reference cross-sectional thread profile (i.e., thread-form) that is V-shaped in the axial reference plane, such as the standardized reference threadforms of the Unified Thread Standard (UTS) and the International Organization for Standardization (ISO). The reference cross-sectional thread profile is also referred to herein as the "reference profile" of the column threads 54. The deviation of the thread profiles from the reference profiles of the column threads 54 cause the actual thread height H1 to be less than a theoretical maximum thread height H2 defined by the reference profiles. This theoretical maximum thread height H2 can also be referred to herein as the "reference height" H2 of the column threads 54. The crests 56 being truncated and/or relieved and the roots 58 being relieved collectively (and each individually) provides such deviations from the reference profile. Additionally, multi-angle flanks 55, 57 and/or or arcuate flank portions also provide deviations from the reference cross-sectional thread profile. The reference height H2 of the column threads 54 is measured, in the axial reference plane, along direction DP1 from a root reference axis 48$a$ to a crest reference axis 46$a$. The crest reference axis 46$a$ intersects crest reference points 56-3 defined at the apices of the reference profile on a first side thereof. Similarly, the root reference axis 48$a$ intersects root reference points 58-2 defined at apices of the reference profile on a second side thereof opposite the first side.

The reference profile is defined by the actual thread profile of the column threads 54. For example, the reference profile has a thread pitch and thread lead equivalent to those of the column threads 54. Additionally, the reference profile is coincident with the thread profile at least at one recurring location of each thread segment 52 in the axial reference plane. For example, as shown in FIG. 2G, the reference profile can be coincident with each of the upper and lower flanks 55, 57 at least at the second reference points 55-2, 57-2 thereof, and also at each location along the linear primary flank portions 55$b$, 57$b$, including at the third reference points 55-3, 57-3 thereof. Thus, for primary flank portions 55$b$, 57$b$ that are linear, as in the embodiment illustrated in FIG. 2G, each crest reference point 56-3 can also be defined as the intersection of: (1) a projection 55$d$ of the respective primary upper flank portion 55$b$, which projection 55$d$ extends from the third upper flank reference point 55-3 and along the consistent linear geometry of the primary upper flank portion 55$b$ toward the central hole axis 22, and (2) a projection 57$d$ of the respective primary lower flank portion 57$b$ the adjacent, axially upward thread segment 52, which projection 57$d$ extends from the third lower flank reference point 57-3 and along the consistent linear geometry of the primary lower flank portion 57$b$ toward the central hole axis 22. In such embodiments, the crest reference points 56-3 of the column threads 54 represent the theoretical crest locations at which these linear primary upper and lower flank portions 55$b$, 57$b$ would converge if they extended uninterrupted (i.e., in an un-truncated fashion) toward the central hole axis 22.

Similarly, in embodiments where the primary flank portions 55$b$, 57$b$ are linear, each root reference point 58-2 can also be defined as the intersection of: (1) a projection 55$e$ of the respective primary upper flank portion 55$b$, which projection 55$e$ extends from the second upper flank reference point 55-2 and along the consistent linear geometry of the primary upper flank portion 55$b$ away from the central hole axis 22, and (2) a projection 57$e$ of the respective primary lower flank portion 57$b$ the adjacent, axially downward thread segment 52, which projection 57$e$ extends from the second lower flank reference point 57-2 and along the consistent linear geometry of the primary lower flank portion 57$b$ away from the central hole axis 22. In such embodiments, the root reference points 58-2 of the column threads 54 represent the theoretical root locations at which these linear primary upper and lower flank portions 55$b$, 57$b$ would converge if they extended uninterrupted (i.e., in an un-relieved fashion) away from the central hole axis 22. Additionally, in view of the foregoing, it is to be appreciated that the reference height H2 represents the theoretical maximum thread height if the primary upper and lower flank portions 55b, 57b of the column threads 54 extended linearly from un-truncated or un-relieved crests (i.e., at the crest reference points 56-3) to un-relieved, intersecting roots (i.e., at the root reference points 58-2).

Figure 2H:
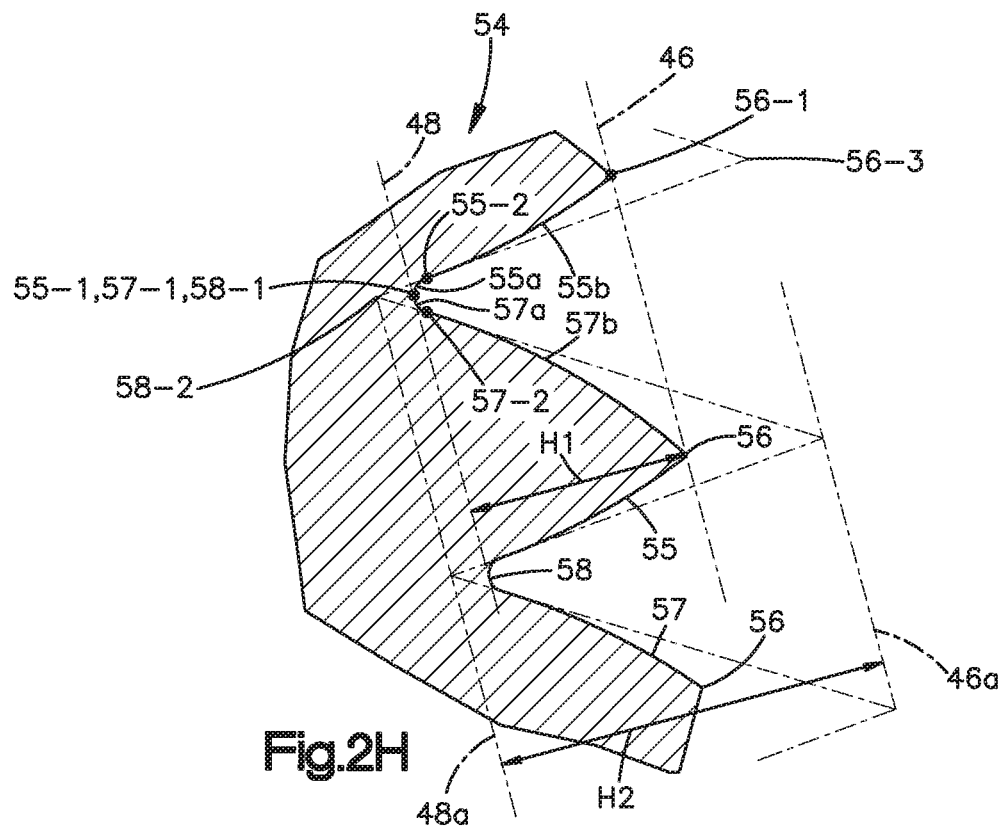
FIG. 2H is an enlarged sectional view of a portion of the threaded locking structure having an alternative geometry to that shown in FIG. 2G.

Referring now to FIG. 2H, an example embodiment of the column threads 54 is shown, in which the column threads 54 have arcuate flank profiles that deviate from the reference profile to cause the thread height H1 to be less than the reference height H2. In this example embodiment, the consistent geometry of the primary portions 55b, 57b of the upper and lower flanks 55, 57 is an involute curve, which extends radially inward from the respective second flank reference point 55-2, 57-2. In this particular example, the primary portions 55b, 57b extend all the way to the crest reference point 56-1 located at the crest 56. It should be appreciated that the crest 56 can optionally be further relieved and/or truncated, such as by being chamfered, beveled, and/or rounded, by way of non-limiting examples. The reference profile can be coincident with each of the upper and lower flanks 55, 57 at least at the second flank reference points 55-2, 57-2 thereof, that is, at the location at which the primary flank portions 55b, 57b intersect the root relief portions 55a, 57a. It should be appreciated that, when the root relief portions 55a, 57a are arcuate (including along an involute curve, as shown), the lines of the V-shaped reference profile can be defined as extending tangentially from the root relief portions 55a, 57a at the second reference points 55-2, 57-2. As described above, the lines of the reference profile extend from crest reference points 56-3 to root reference points 58-2.

Figure 2I:
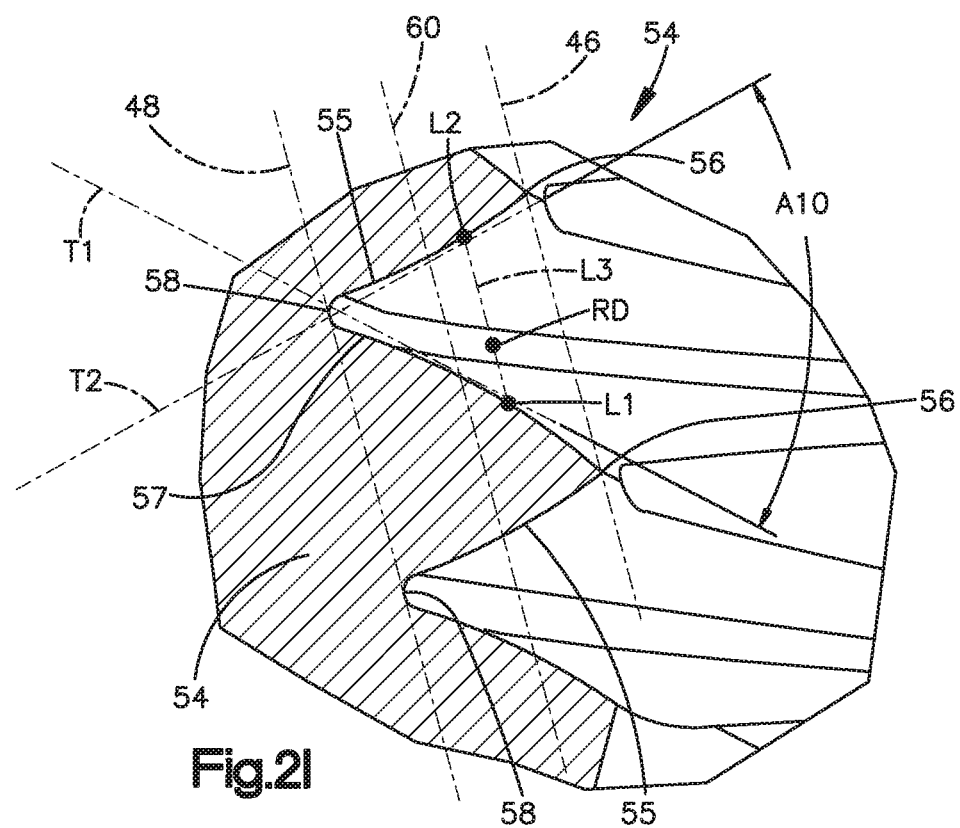
FIG. 2I is another view of the enlarged sectional view of FIG. 2H.

Referring now to FIG. 2I, the curved profile of the flanks 55, 57 defines a varying thread angle A10. At any radial location RD of the column threads 54, the varying thread angle A10 can be defined as the angle between a pair of tangent lines T1, T2 intersecting the primary flank portions 55b, 57b at respective locations L10, L20 along a reference line L30 parallel with the thread midline 60 and coincident with the radial location RD. In such embodiments, the varying thread angle A10 can vary within any of the ranged described above with reference to angle A4.

Figure 3A:
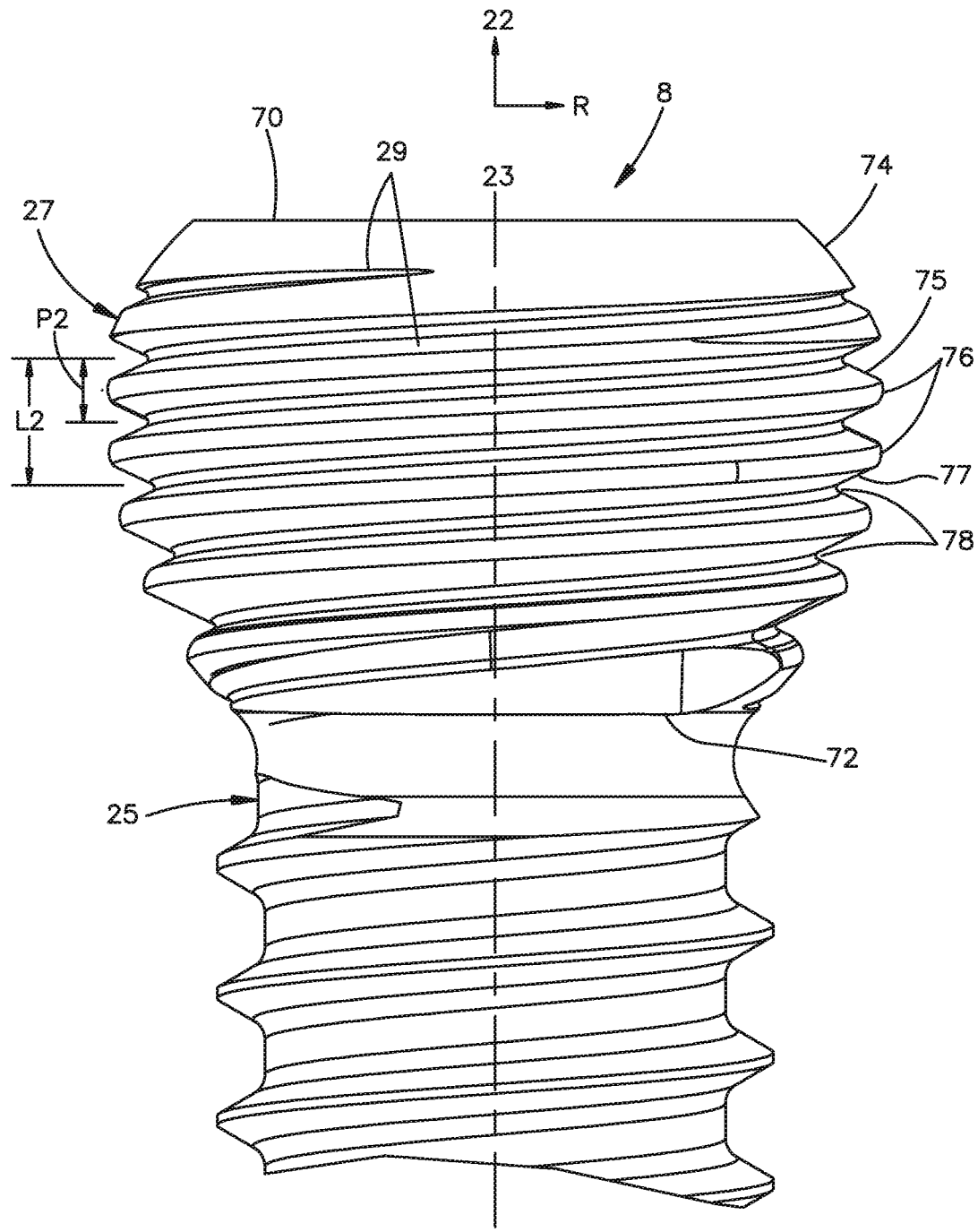
FIG. 3A is a side view of a head of a variable-angle (VA) locking screw configured to be locked to the bone plate of FIG. 1A within one of the locking holes.

Referring now to FIG. 3A, the head 27 of the VA locking screw 8 defines a proximal end 70 and a distal end 72 spaced from the proximal end 70 along an axial screw direction Z2 oriented along the central screw axis 23. The head 27 also defines an outer surface 74 that extends from the proximal end 70 to the distal end 72 and defines the external screw head threads 29. In the illustrated embodiment, the external screw head threads 29 extend substantially from the proximal end 70 to substantially the distal end 72 of the head 27 along one or more thread paths, which can be helical. The external screw head threads 29 define crests 76 spaced radially outwardly from roots 78 with respect to the central screw axis 23. The screw head threads 29 also define upper flanks 75 and lower flanks 77 that extend from the crests 76 to respective axially upper and lower roots 78.

The screw head threads 29 can define a thread pitch P2 and a thread lead L2, which can be measured with respect to the roots 78. As shown, the one or more thread paths can include a pair of non-intersecting thread paths, such as double-lead threads, in which the threads 29 define a thread lead L2 that is equivalent to twice the thread pitch P2. However, in other embodiments, the one or more thread paths of the screw head threads 29 can include a single thread path (i.e., single-lead) or three or more thread paths (e.g., triple-lead, etc.). The one or more thread paths of the plate head threads 29 are configured to be complimentary with the one or more thread paths of the plate threads 9. It should be appreciated, however, that the screw head threads 29 and the plate threads 9 need not have the same number of thread paths. By way of a non-limiting example, one of the plate threads 9 and the screw head threads 29 can be double-lead threads defining a thread pitch, while the other of the plate threads 9 and screw head threads 29 can be single-lead threads having a thread lead that is substantially equivalent to the foregoing thread pitch. Other variations in the thread paths of the plate threads 9 and the screw threads 29 are also within the scope of the present disclosure.

Referring now to FIG. 3B, in an axial reference plane that extends along the central screw axis 23, the external screw head threads 29 define a crest trajectory axis 86 that intersects the crests 76 and a root trajectory axis 88 that intersects the roots 78. As shown, the crest trajectory axis 86 and the root trajectory axis 88 can define arcuate, convex shapes, which is advantageous for angulated locking with the plate threads 9. In additional embodiments, the crest and root trajectory axes 86, 88 can be generally spherical. As used herein, the term "spherical" its derivatives means at least a portion of a sphere or at least a portion of a spheroid, including such portions of a prolate spheroid and/or an oblate spheroid, by way of non-limiting examples, and also encompasses substantial approximations of such portions of a sphere and/or spheroid. It should be appreciated, however, that other crest and root trajectory axis 86, 88 geometries are within the scope of the present disclosure, including those described more fully in the '284 Reference.

The external screw head threads 29 can be characterized as defining a sequence of helically-adjacent screw head thread segments 73, which can extend continuously or discontinuously along the one or more thread paths. As depicted, the screw head threads 29 can define thread segments 73 that are axially adjacent. Because the screw head threads 29 are external threads, each thread segment 73 thereof can be axially centered at the crest 76, and includes the upper flank 75 ascending from the crest 76 to the axially upward root 78, and also includes the lower flank 77 descending from the crest 76 to the axially lower root 78. Accordingly, each thread segment 73 of the screw head threads 29 is configured to intermesh with (i.e., at least partially reside within) at least one associated thread segment 52 of the plate threads 9. The upper and lower flanks 75, 77 of axially adjacent thread segments 73 are offset from one another at an angle A6, which defines the thread angle of the screw head threads 29. Thus, angle A6 can also be referred to the "head thread angle" A6.

Figure 3C:
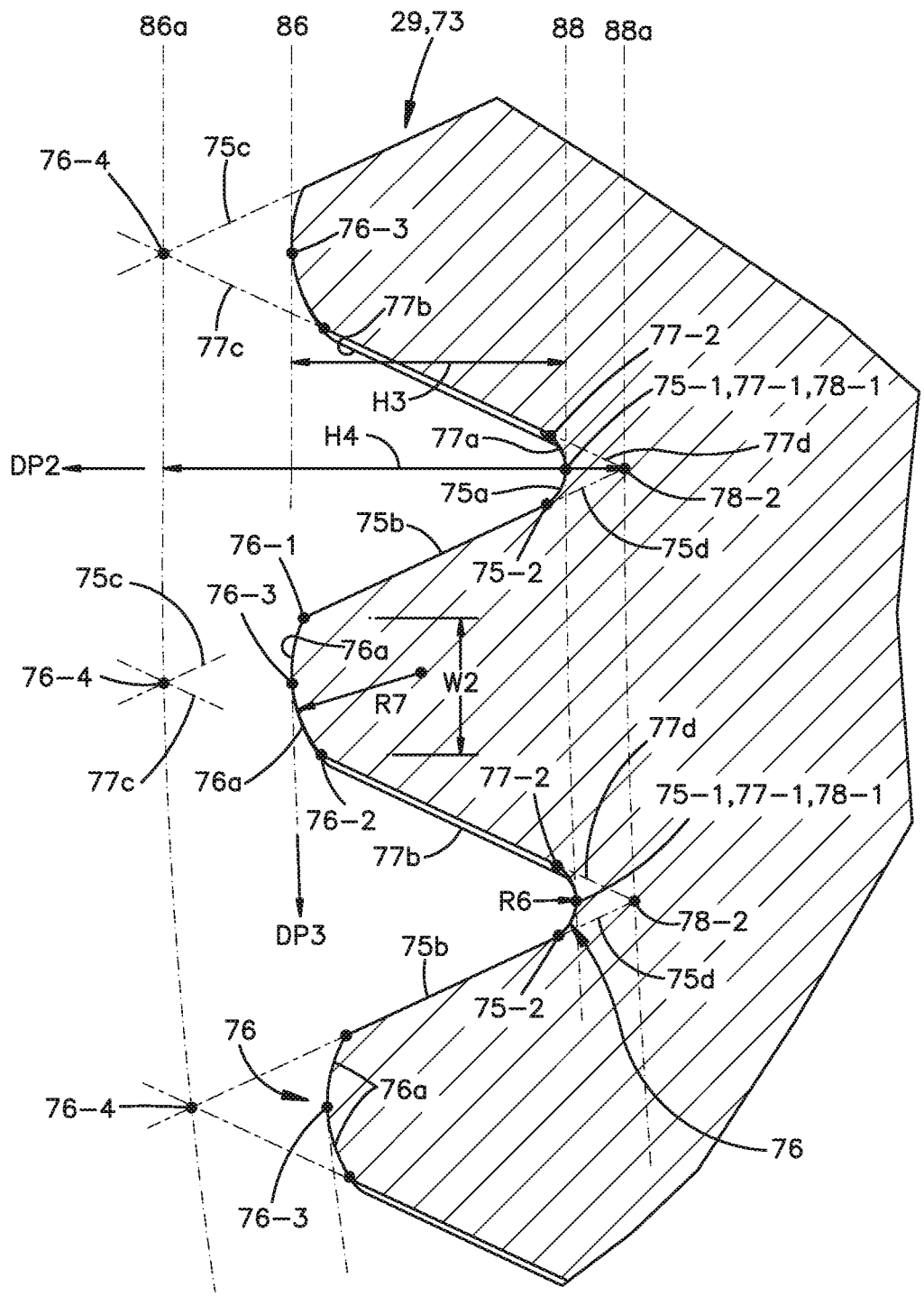
FIG. 3C is an enlarged sectional side view of a portion of the VA locking screw illustrated in FIG. 3B.

Referring now to FIG. 3C, the thread profiles (i.e., threadforms) of the screw head threads 29 will now be described, as defined within the axial reference plane that contains (and is thus oriented along) the central screw axis 23.

As above, the crests 76 define crest profiles; the roots 78 define root profiles; and the upper and lower flanks 75, 77 define respective upper and lower flank profiles. In the illustrated embodiment, and with reference to a radially outward direction away from the central screw axis 23, the profile of the upper flank 75 includes:
  a) a first upper flank portion 75a (also referred to as a "root relief portion") that extends from a first upper flank reference point 75-1 to a second upper flank reference point 75-2; and
  b) a second or "primary" upper flank portion 75b that extends along a consistent geometry from the second upper flank reference point 75-2 to an upper crest reference point 76-1.

Similarly, in the illustrated embodiment, and with reference to the radially inward direction, the profile of the lower flank 77 includes:
  a) a first lower flank portion 77a (also referred to as a "root relief portion") that extends from a first lower flank reference point 77-1 to a second lower flank reference point 77-2; and
  b) a second or primary lower flank portion 77b that extends along a consistent geometry from the second lower flank reference point 77-2 to a lower crest reference point 76-2.

As above, the root relief portions 75a, 77a are configured for reducing stress concentrations at the roots 78 of the screw head threads 29. In the illustrated embodiment, the lower root relief portion 77a of a thread segment 73 is coincident with the upper root relief portion 75a of the axially lower head thread segment 73. In particular, reference points 77-1 and 75-1 are coincident with each other and with a root reference point 78-1, which is coincident with the root 78 (i.e., the nadir of the thread segment 73). As shown, these contiguous root relief portions 77a, 75a can each be arcuate and can define a common relief radius R6, which can be in a range of about 0.005 mm to about 0.10 mmm, more particularly in a range of about 0.02 mm to about 0.08 mm, more particularly in a range of about 0.03 mm to about 0.05 mm, and can also be greater than 0.10 mm (i.e., not less than 0.10 mm), including a relief radius large enough to approximate a linear root profile in the axial reference plane. Accordingly, the first lower and upper flank portions 77a, 77a can be referred to as respective "root relief" portions of the flanks 77, 75. As depicted, the root 78 profile of each head thread segment 73 can consist of a single point 78-1, although in other embodiments the root profile can be elongated, including linearly, in the axial reference plane.

In the illustrated embodiment, the consistent geometries of the primary flank portions 75b, 77b are linear, and define the head thread angle A6, which can be in a range of about 48 degrees to about 52 degrees, and can also be in a range of about 40 degrees to about 60 degrees, and can further be in a range of about 25 degrees to about 75 degrees. It should be appreciated that the primary flank portions 75b, 77b can alternatively define consistent geometries that are non-linear, such as curved, including an involute curve, similarly as described above with reference to FIGS. 2H and 2I, or a curve having a constant, relatively large radius.

The head thread segments 73 define crest profiles 76a that extend between the upper and lower crest reference points 76-1, 76-2. The crest profiles 76a can be convex, and are preferably radiused, rounded, chamfered, beveled, or otherwise truncated and/or relieved for reducing stress concentrations along the crest profile 76a. As depicted, the crest profile 76a can define a relief radius R7, which can be in a range of about 0.01 mm to about 0.40 mm, and/or in a range of about 0.11 mm to about 0.13 mm, and/or in a range of about 0.07 mm to about 0.15 mm, and/or in a range of about 0.03 mm to about 0.18 mm. In such convex profiles, a crest tip reference point 76-3 is defined at the apex of the crest profile 76a, as measured from the central screw axis 23. The crest trajectory axis 86 intersects each of the crest tip reference points 76-3. Additionally, the crest profiles 76a can define respective crest widths W2, as measured between the upper and lower crest reference points 76-1, 76-2 along a direction DP3 oriented along the crest trajectory axis 86 at the crest tip reference point 76-3. The crest width W2 can be in a range of about 0.11 mm to about 0.15 mm, and/or in a range of about 0.08 mm to about 0.18 mm, and/or in a range of about 0.01 mm to about 0.20 mm. In some embodiments, the crest width W2 is 0.10 mm or greater (i.e., no less than 0.10 mm). It should be appreciated that the foregoing geometries of the crest profiles 76a are provided as non-limiting examples, and that other crest profile geometries are within the scope of the present disclosure, including linear crest profiles 76a.

The screw head threads 74 define a head thread height H3 measured from the crest 76 to the root 78 in the axial reference plane. In particular, the head thread height H3 of any of the head thread segments 73 is measured between the root reference point 78-1 to the crest trajectory axis 86, along a direction DP2 perpendicular to that portion of the crest trajectory axis 86. The head thread height H3 can be in a range of about 0.05 mm to about 2.00 mm, and can also be in a range of about 0.10 mm to about 1.50 mm, and can also be in a range of about 0.11 mm to about 0.50 mm, and can also be in a range of about 0.24 mm to about 0.28 mm, and can also be in a range of about 0.20 mm to about 0.30 mm, and can further be in a range of about 0.12 mm to about 0.34 mm.

Similarly as described above with reference to the plate threads 9, the thread profiles of the screw head threads 29 deviate from a reference cross-sectional thread profile (i.e., "reference profile") that is V-shaped in the axial reference plane. This deviation from the reference profile of the screw head threads 29 causes the actual head thread height H3 to be less than a theoretical maximum head thread height H4 comprising un-truncated and/or un-relieved crests 76 and un-relieved roots 78. This theoretical maximum head thread height H4 can also be referred to herein as the "reference height" H4 of the screw head threads 29. The reference height H4 of the screw head threads 29 is measured, in the axial reference plane, from a root reference axis 88a to a crest reference axis 86a, along direction DP2. The crest reference axis 86a intersects reference points 76-4, which are defined at the apices of the reference profile on a first side thereof. Also similarly, the root reference axis 88a intersects reference points 78-2, which are defined at apices of the reference profile on a second side thereof opposite the first side. The reference height H4 of the screw head threads 29 represents the theoretical maximum head thread height should the primary upper and lower flank portions 75b, 77b extend from a un-truncated crest to an un-relieved root.

As above, the reference profile of the screw head threads 29 is defined by the actual thread profile of the screw head threads 29, and has a thread pitch and thread lead equivalent to those of the screw head threads 29. Additionally, the reference profile is coincident with the thread profile at least at one recurring location of each thread segment 73 in the axial reference plane. For example, as shown in FIG. 3C, the reference profile can be coincident with each of the upper and lower flanks 75, 77 at least at the second flank reference points 75-2, 77-2 thereof, and also at each location along the linear primary flank portions 75b, 77b, including at reference points 76-1 and 76-2. Thus, for linear primary flank portions 75b, 77b: each crest reference point 76-4 can also be defined by intersections of projections 75c, 77c of the upper and lower primary flank portions 75b, 77 along their respective consistent geometries away from the central screw axis 23; and each root reference point 78-2 can also be defined by intersections of projections 75d, 77d of the primary flank portions 75b, 77 along their respective consistent geometries toward the central screw axis 23.

Referring now to FIGS. 4A and 4B, the complimentary thread proportions described above can enhance the mechanical strength of the locked thread interface between the plate threads 9 and the screw head threads 29. For example, the thread profile geometry of the dual-angle column threads 54 can provide an increased form-fit, particularly at angulated screw 9 insertion trajectories, such as that depicted in FIGS. 4A and 4B. Additionally, the axial space between the opposed flank profiles 55a-c, 57a-c provides favorable clearance between the roots 58 of the plate threads 9 and the crests 76 of the screw head threads 29. Such crest-to-root 76-58 clearance is particularly beneficial at angulated insertion trajectories because it prevents or at least reduces undesirable mechanical interference between the head crests 76 and the plate roots 58. Additionally, the rounded crest profiles 76a of the screw head threads 29, particularly those having relatively large relief radii R7, effectively rounds or removes sensitive edges of the screw head threads 29 that could otherwise deleteriously mechanically interfere with plate threads 9.

A further advantage provided by the thread proportions described herein is that a measure of control is provided over the thread deformation at the thread interface. In particular, by interfacing the stronger profile of the screw head thread segments 73 against the more malleable profile of the plate thread segments 52, a vast majority of the thread deformation can be imparted to the plate threads 9. At angulated screw 9 insertion trajectories, such controlled deformation can allow the plate threads 9 to deform so as to effectively re-align to the angulated central screw axis 23. Such controlled deformation also provided enhanced locking with the angulated screw head 27. After form-fit is achieved, further rotational advancement of the VA locking screw 8 with respect to the column threads 54 can commence deforming the one or more column threads 54, preferably at the crests 56, as shown at interference regions 99 in FIG. 4B. This deformation occurs primarily radially outward, although some measure of axial and/or circumferential deformation can occur (mostly when a timing-error is present). Moreover, the radial deformation can include plastic and elastic deformation, which compresses the one or more column threads 54 in a manner exerting a reactive compressive force against the associated screw head threads 29, primarily at the roots 78 thereof, achieving a locking press-fit with the screw head 27. It is to be appreciated that the plate threads 9 are also axially deformable, which allows the plate threads 9 to deform axially downward or upward, such as when the VA locking screw 8 is inserted with timing error.

With respect to the foregoing aims of enhancing the mechanical strength of the locked thread interface and reducing cross-threading, particularly at of the screw head 27 at angulation, and also limiting cross-threading so that is occurs substantially entirely within the plate threads 29 and as an act of plastic and elastic thread deformation, the inventors have identified, through their own extensive testing, particularly effective parameters of the thread proportions discussed above. One such thread proportion parameter for the plate threads 9 and screw head threads 29 is the relationship between the actual thread height H1, H3 versus the reference height H2, H4. For example, the plate threads 9, particularly the column threads 54, define a plate thread height factor ("HF-P"), which is calculated as a ratio of the actual thread height H1 to the reference height H2 of the column threads 54 (i.e., (HF-P)=H1/H2). The plate thread height factor (HF-P) is preferably in a range of about 0.50 to about 0.60, and can also be in a range of about 0.40 to about 0.75, and can further be in a range of about 0.30 to about 1.00. Similarly, the screw head threads 29 define a screw head thread height factor ("HF-S"), which is calculated as a ratio of the actual thread height H3 to the reference height H4 of the screw head threads 29 (i.e., (HF-S)=H3/H4). The screw head thread height factor (HF-S) is preferably in a range of about 0.63 to about 0.67, and can also be in a range of about 0.55 to about 0.75, and can further be in a range of about 0.40 to about 0.90. The screw head thread height factor (HF-S) is preferably combined with a rounded crest profile 76a having a relatively large crest width W2, as well as a relatively large relief radius R7, such as the values of W2 and R7 described above.

Additionally, the plate threads 9 (particularly the column threads 54) and the screw head threads 29 can define a comparative height factor ("CHF"), which is calculated herein as a ratio of the actual thread height H1 of the plate threads 9 to the actual thread height H3 of the screw head threads 29 (i.e., CHF=H1/H3). The comparative height factor (CHF) is preferably in a range of about 1.58 to about 1.62, and can also be in a range of about 1.30 to about 1.90, and can further be in a range of about 1.00 to about 2.00.

In combination with the foregoing values recited for the plate thread height factor (HF-P), the screw head thread height factor (HF-S), and the comparative height factor (CHF), the inventors have discovered through their extensive testing that particularly favorable thread deformation occurs when plate thread angle A4 is in a range from 25 degrees to 35 degrees and the head thread angle A6 is in a range from 45 degrees to 60 degrees, including the multi-angle embodiments where A4 is the first thread angle of the plate threads 9. The inventors have discovered, surprisingly and unexpectedly, that the foregoing combination of parameters can cause most if not substantially all of the thread deformation at the locking interface between the plate threads 9 and screw head threads 29 to occur within the plate threads 9. Stated differently, the inventors have discovered a particular combination of thread parameters that effectively cause the screw head threads 29 to plastically deform the plate threads 9 substantially without being plastically deformed themselves.

It is to be appreciated that the designs of the VA locking holes 6 and the screw head 27, including the thread proportion parameters thereof, can be adjusted while remaining within the scope of the present disclosure. For example, additional embodiment of the VA locking hole 6 will now be described with reference to FIGS. 5A through 9D. The VA locking holes 6 of these additional embodiments are generally similar to the VA locking hole 6 described above with reference to the preceding embodiment described above with reference to FIGS. 2A through 2G. Accordingly, like reference numbers from the preceding embodiment will also be used in these additional embodiments. Moreover, it should be appreciated that, for the sake of brevity, the following disclosure will focus primarily on the differences between the VA locking holes 6 of these additional embodiment and the preceding embodiment.

Figure 5A:
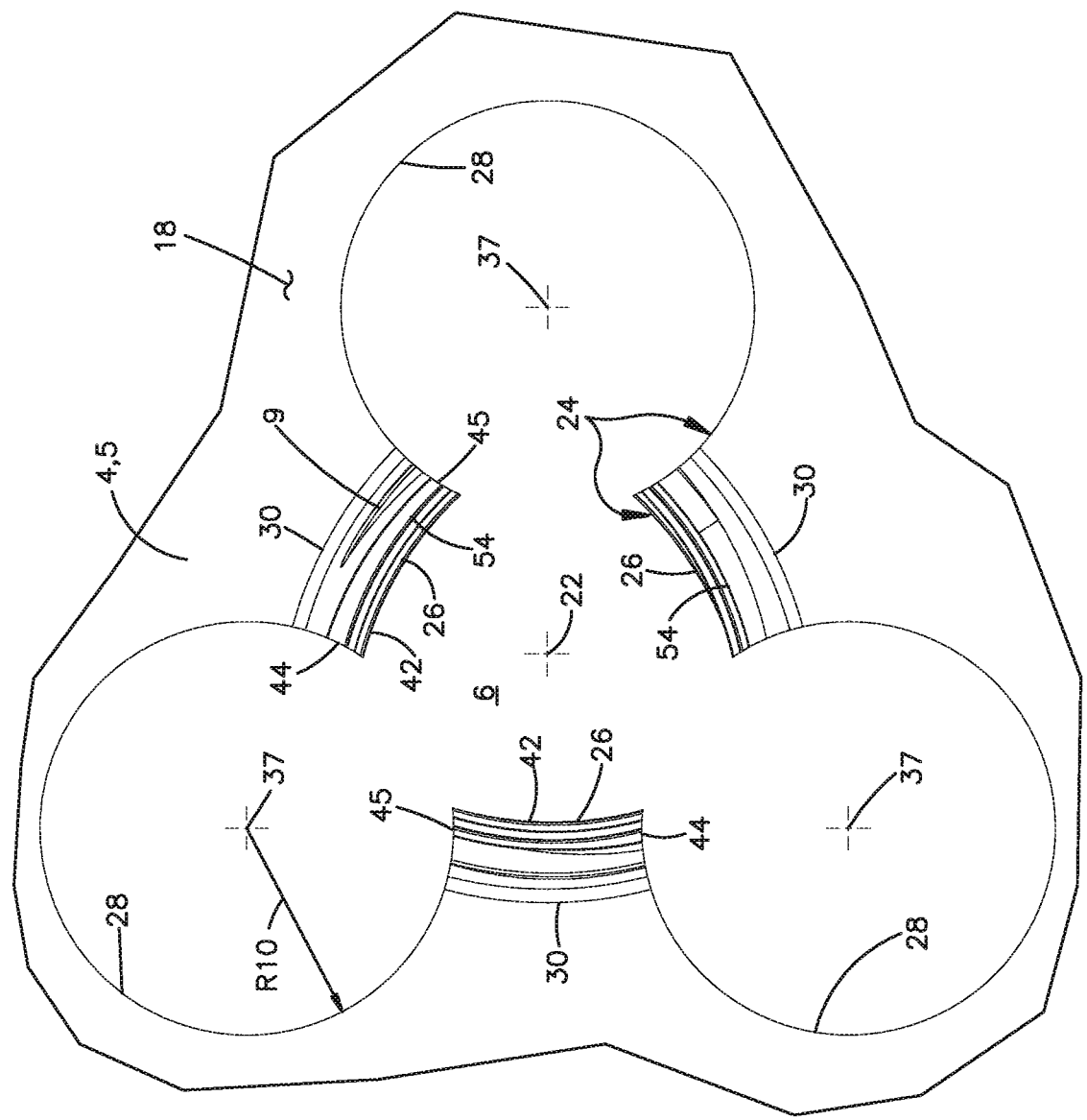
FIG. 5A is a top view of another locking hole, which has a threaded locking structure defined by an interior surface of the locking hole, according to another embodiment of the present disclosure.
Figure 5B:
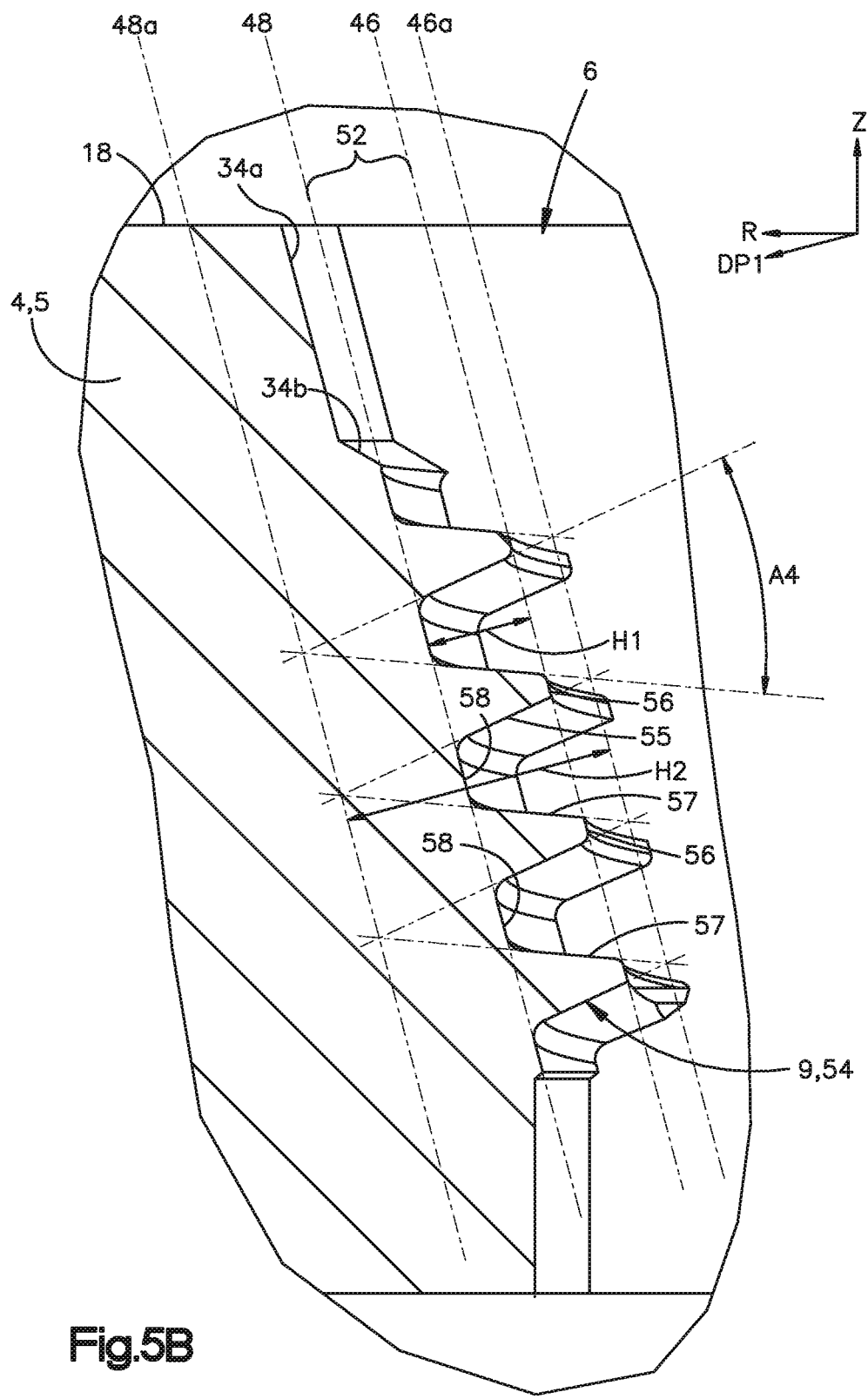
FIG. 5B is an enlarged sectional view of the threaded locking structure of the locking hole illustrated in FIG. 5A.

Referring now to FIGS. 5A through 5D, an additional embodiment of the VA locking hole 6 is shown having, among other things, a thinner thread profile and larger recesses 28 than those of the preceding embodiment. As shown in FIG. 5A, the recesses 28 of the present disclosure define a recess radius R10 greater than that of the preceding embodiment, such that the recesses 28 of the present embodiment each have a horizontal profile that subsumes a majority of a circle. Accordingly, at least a portion of the first and second sides 44, 45 of each threaded column 26, particularly the portions contiguous with the first surface 42, can taper toward each other. As depicted, the VA locking hole 6 of the present embodiment can have three (3) threaded columns 26 and three (3) recesses 28 sequentially located circumferentially between the columns 26, although the present embodiment can have fewer than three (3) or more than three (3) columns 26 and recesses 28. As shown in FIG. 5B, the hole 6 can also have a first lead in surface 34*a* that is steeper than the lead in surface 34 of the preceding embodiment. A second, lower lead in surface 34*b* can be contiguous with the first lead in surface 34*a*, an can be oriented at a shallower angle relative to the first lead in surface 34*a*.

Figure 5C:
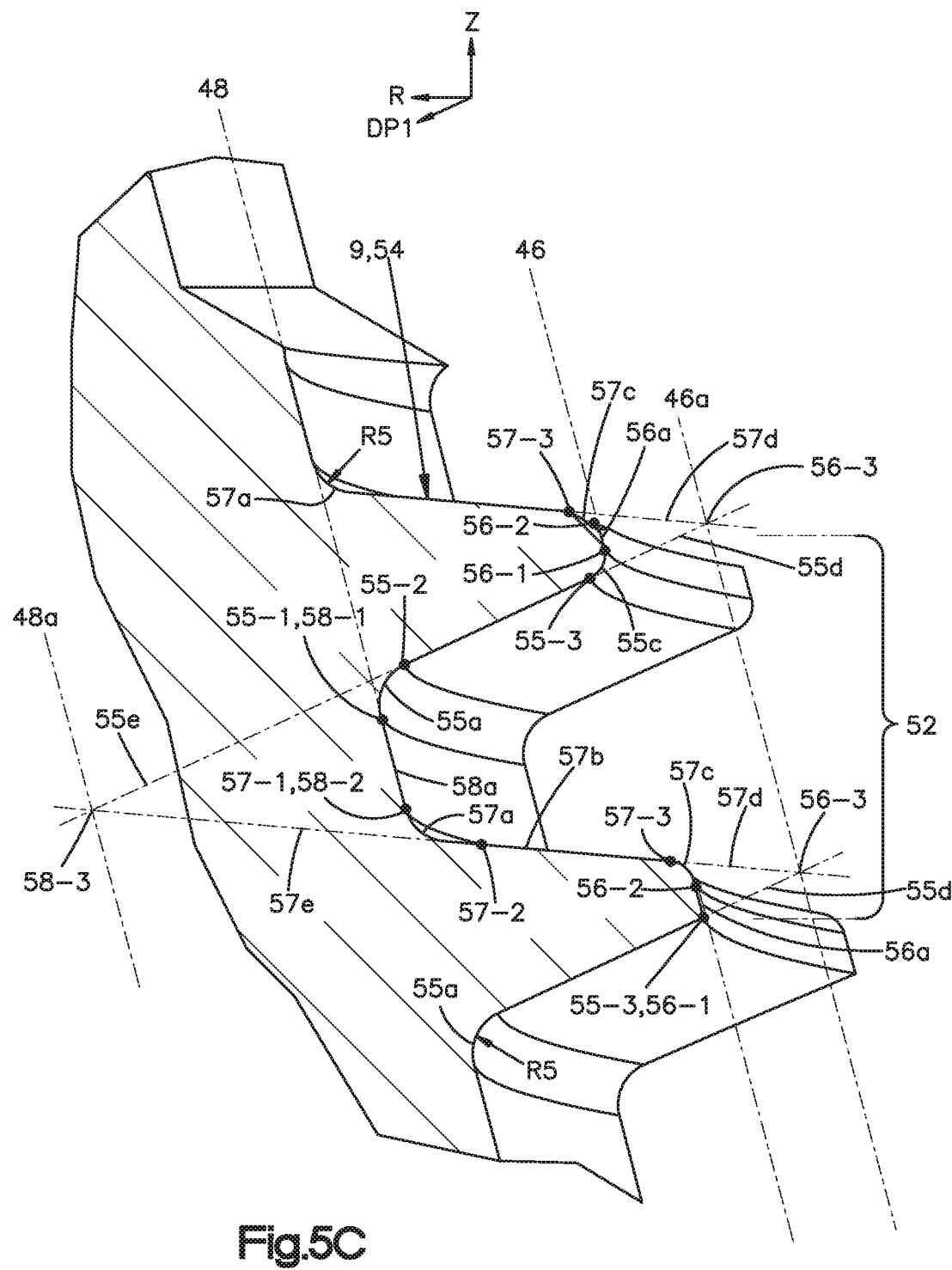
FIG. 5C is a sectional side view of a threaded head of another VA locking screw, which is configured to be locked at least with the locking hole illustrated in FIG. 5A.

Referring now to FIGS. 5B and 5C, as above, the crests 56 of the column threads 54 extend along the crest trajectory axis 46, and the roots 58 of the column threads extend along the root trajectory axis 48. Also, the column threads 54 define a thread angle A4 measured between the upper flank 55 and the lower flank 57 of a thread segment 52. In addition to having thinner profiles, the column threads 54 of the present embodiment define a single thread angle A4, which can be in a range of about 25 degrees to about 35 degrees, and can also be in a range of about 20 degrees to about 50 degrees, and can further be in a range of about 15 degrees to about 75 degrees. The column threads 54 of the present embodiment define a thread height H1 and a reference height H2. As above, the thread height H1 represents the actual thread height of the column threads 54, while the reference height H2 represents the theoretical maximum thread height comprising un-truncated crests 56 and un-relieved roots 58. At any of the thread segments 52, the thread height H1 is measured from the crest trajectory axis 46 to the root 58 along the direction DP1 perpendicular to the crest trajectory axis 46, while the reference height H2 is measured from the crest reference axis 46*a* to the root reference axis 48*a* along direction DP1.

As shown in FIG. 5C, the roots 58 of the present embodiment define elongated root profiles 58*a* that extend linearly along the root trajectory axis 48, which increases the total area between the opposed flanks 55, 57. This increases area between the flanks 55, 57, in combination with the thinner thread profiles, allows the column threads 54 to have beneficial malleability (and thus deformability) when engaged with the screw head threads 29. Furthermore, with reference to a radially inward direction, the profile of the upper flank 55 includes:
 a) a first upper flank portion 55*a* (or upper "root relief" portion 55*a*) that extends from a first upper flank reference point 55-1 to a second upper flank reference point 55-2;
 b) a second or "primary" upper flank portion 55*b* that extends along a consistent geometry from the second upper flank reference point 55-2 to a third upper flank reference point 55-3; and
 c) a third upper flank portion 55*c* (or upper "crest relief" portion 55*c*) that extends from the third upper flank reference point 55-3 to a lower crest reference point 56-1.

Similarly, with reference to the radially inward direction, the profile of the lower flank 57 includes:
 a) a first lower flank portion 57*a* (or lower "root relief" portion 57*a*) that extends from a first lower flank reference point 57-1 to a second lower flank reference point 57-2;
 b) a second or primary lower flank portion 57*b* that extends along a consistent geometry from the second lower flank reference point 57-2 to a third lower flank reference point 57-3; and
 c) a third lower flank portion 57*c* (or lower "crest relief" portion 57*c*) that extends from the third lower flank reference point 57-3 to an upper crest reference point 56-2.

In the present embodiment, the root profile 58*a* extends from an upper root reference point 58-1, which is coincident with the first upper flank reference point 55-1, to a lower root reference point 58-2, which is coincident with the first lower flank reference point 57-1. As before, the upper and lower root relief portions 55*a*, 57*a* can each be arcuate and define a root relief radius for reducing reduce stress concentrations at the root 58. The root relief radius R5 can optionally be the same (i.e., common) for the upper and lower root relief portions 55*a*, 57*a*. It should be appreciated that the root relief radius R5 of the plate threads 9 can optionally be substantially equivalent to the crest relief radius R7 of the screw head threads 29. Additionally, in the present embodiment, the upper and lower crest relief portions 55*c*, 57*c* can be arcuate and define a crest relief radius for reducing stress concentrations at the crest 56. As shown, one or more of the thread segments 52 of the present embodiment can have a primary flank profile portion 55*b*, 57*b* that extends to the respective upper or lower crest reference point 56-1, 56-2. Stated differently, one or more of the crests 56 need not have both upper and lower crest relief portions 55*c*, 57*c*. Moreover, as above, a transition portion, which can be arcuate, can optionally extend between the primary flank portions 55*b*, 57*b* and the respective third upper and lower flank portions 55*c*, 57*c* of any and up to all of the profiles flanks 55, 57.

As above, the crest reference axis 46*a* intersects crest reference points 56-3 of the reference profile, and the root reference axis 48*a* intersects root reference points 58-3 of the reference profile. Also similarly as described above, when the primary flank portions 55*b*, 57*b* are linear, the crest reference points 56-3 and the root reference points 58-3 can also be defined by respective intersections of the projections 55*d*, 57*d* and 55*e*, 57*e* of the primary flank portion 55*b*, 57*b* along their consistent geometries.

In the present embodiment, the thread height H1 can be in a range substantially equivalent to that described above with reference to FIG. 2G. Additionally, the plate thread height factor (HF-P) of the present embodiment can be in a range of about 0.36 to about 0.40, and can also be in a range of about 0.34 to about 0.70, and can further be in a range of about 0.30 to about 1.00. It should be appreciated that the elongated root profile 58*a* of the present embodiment effectively moves the root reference axis 48*a* further away from the central hole axis 22 relative to the preceding embodiment, which can also reduce the plate thread height factor (HF-P) relative to the preceding embodiment.

Figure 5D:
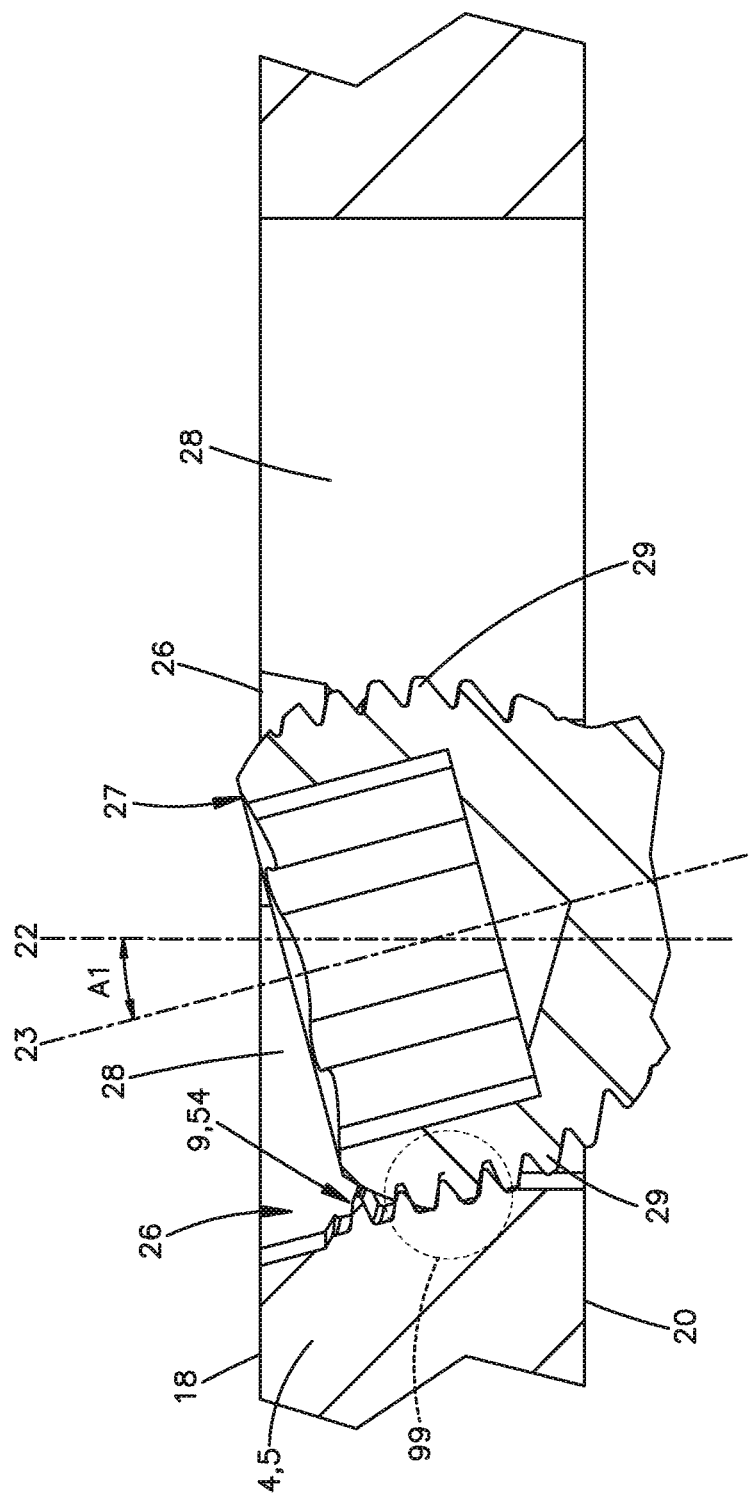
FIG. 5D is a sectional side view of the head of the VA locking screw illustrated in FIG. 5C in locking engagement with the locking hole illustrated in FIG. 5A.

Referring now to FIG. 5D, the thinner thread profiles of the present embodiment can also provide enhanced locking with the VA screw head 27, including advantageous thread deformation and enhanced mechanical locking strength, compared to prior art thread designs. Although the column threads 54 of the present embodiment might not provide as much radial clearance between the column thread roots 58 and the crests 76 of the screw head threads 29 as the preceding embodiment, the thinner profiles of the column threads 54 of the present embodiment can allow the column threads 54 to deform more readily upon engagement with the screw head threads 29, including at angulated screw insertion trajectories. For example, as shown in FIG. 5D, at angulation (such as an angulation A1 of about 15 degrees), the column threads 54 can deform favorably in the radial direction R (as well as along direction DP1) at their crests 56 and flanks 55, 57 responsive to engagement with the screw head threads 29 at interference region 99. Additionally, the upper and lower flanks 55, 57 of the column threads 54 are generally positioned at complimentary orientations with the upper and lower flanks 75, 77 of the screw head threads 29 at angulation, which provides a beneficial form fit at angulation. As above, by interfacing the stronger profiles of the screw head thread threads 29 against the thinner, malleable profile of the column threads 54 of the present embodiment, the vast majority of the thread deformation can be imparted to the plate threads 9, allowing the plate threads 9 to deform so as to effectively re-align to the angulated central screw axis 23. Additionally, the foregoing deformation, as above, occurs primarily radially outward, although some measure of axial and/or circumferential deformation can occur (mostly when a timing-error is present).

Figure 6A:
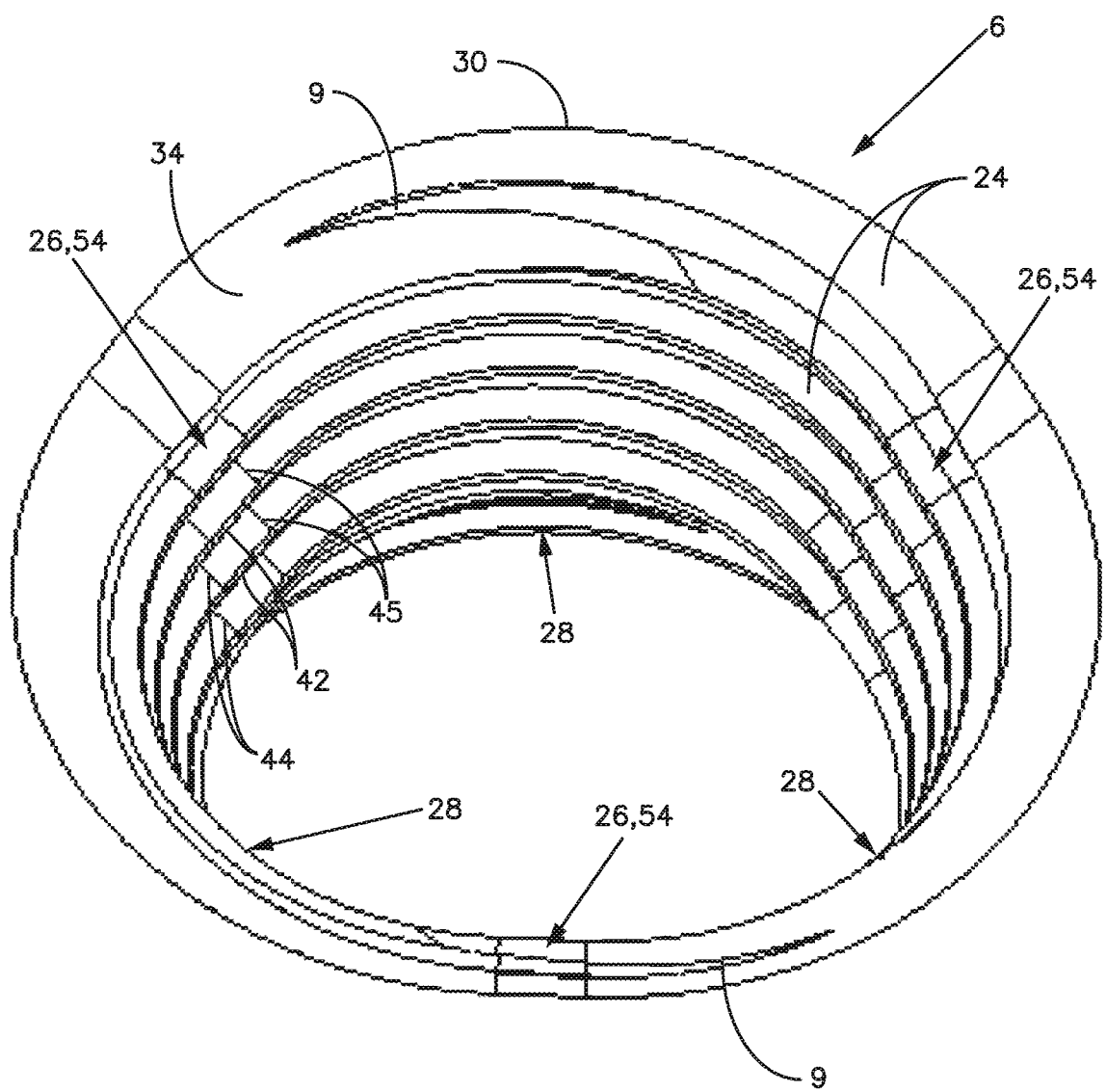
FIG. 6A is a perspective view of another locking hole, which has a trigon horizontal hole profile, and includes a threaded locking structure defined by an interior surface of the locking hole, according to an additional embodiment of the present disclosure.
Figure 6B:
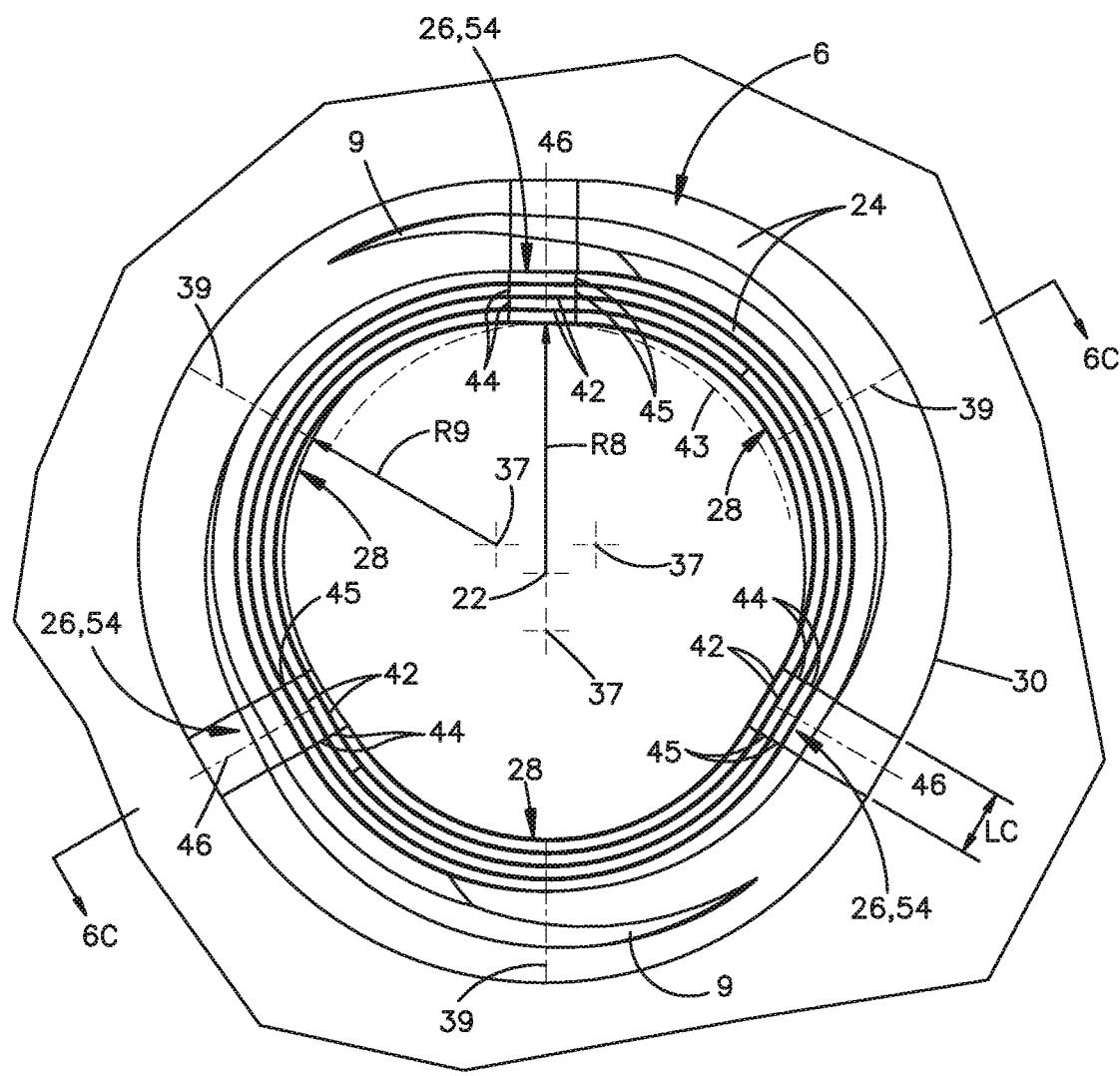
FIG. 6B is a top view of the locking hole illustrated in FIG. 6A.

Referring now to FIGS. 6A and 6B, in additional embodiments, the VA locking hole 6, or at least an axial portion thereof, can have a horizontal hole profile that is non-circular. By way of non-limiting example, at least an axial portion of the hole 6 can have a generally polygonal horizontal hole profile. In particular, the present embodiment of the VA locking hole 6 is shown having a trigon (i.e., generally triangular) horizontal profile, although other polygonal shapes are within the scope of the present disclosure. The interior surface 24 of the plate body 5 within the hole 6, or at least an axial portion thereof, defines a corresponding non-circular (e.g., trigon) horizontal profile. Additionally, plate threads 9 extend along a thread path that has a corresponding non-circular (e.g., trigon) horizontal profile. Moreover, one or more and up to each of the upper perimeter 30, the one or more lead in surfaces 34, the one or more undercut surfaces 36, and the lower perimeter 32 of the hole 6 can also have corresponding non-circular (e.g., trigon) horizontal profiles.

In the illustrated embodiment, the first surfaces 42 of the columns 26 have linear horizontal profiles. In other embodiments, one or more of the first surfaces 42 can have arcuate profiles having a relatively large radii. In either of such embodiments, the first surfaces can tangentially intersect a reference circle 43 centered at the central hole axis 22. In particular, the first surfaces 42 can intersect the reference circle 43 substantially at the crest trajectory axis 46. Is should be appreciated that the reference circle 43 illustrates the hole's departure from a circular horizontal profile. The reference circle 43 in FIG. 6B is shown intersecting an axially lowermost one of the first surfaces 42 within the polygonal hole 6, at which axial location the reference circle 43 also illustrates the minimum diameter within the hole 6 (and thus also the minimum minor diameter of the plate threads 9). The reference circle 43 defines a radius R8, which, for the depicted reference circle 43, is equivalent to one-half (½) the minimum minor thread diameter of the hole 6. For the depicted reference circle 43, the radius R8 can be in a range of about 2.0 mm to about 2.1 mm, and can also be in a range of about 1.8 mm to about 2.5 mm. In additional embodiments, including those for use with VA locking screws 8 with screw shafts 25 having a major diameter in the ranges listed above with reference to FIG. 1A (i.e., ranges of about 0.5 mm to about 10.0 mm, about 1.0 mm to about 7.0 mm, about 2.0 mm to about 4.0 mm, and more particularly a major diameter of about 3.5 mm), radius R8 can be in a range of about 0.5 mm to about 15.0 mm, more particularly in a range of about 1.0 to about 10.0 mm, more particularly in a range of about 1.0 mm to about 5.0 mm, more particularly in a range of about 1.5 mm to about 5.0 mm, and more particularly in ranges of about 2.0 mm to about 4.0 mm, about 0.5 mm to about 3.5 mm, about 1.8 mm to about 2.5 mm, and about 2.0 mm to about 2.1 mm. It should be appreciated that radius R8 can optionally be used as a metric for categorizing the size of the hole 6 (for example, as an alternative of, or in addition to, any of the mean crest radius R2, the mean radius R3, and the mean root radius R4 described above). As above, the first surface 42 of each column 26 extends between a first side 44 and a second side 45, which sides 44, 45 define interfaces between the column 26 and the circumferentially adjacent recesses 28. In the present embodiment, however, the recesses 28 extend tangentially from the first and second sides 44, 45 of the associated columns 26. In this manner, the first surfaces 42 of the columns 26 effectively define the sides of the trigon, while the recesses 28 effectively define the corners of the trigon, each as viewed in the horizontal reference plane. Accordingly, the columns 26 and recesses 28 of the present embodiment can also be referred to respectively as "sides" and "corners" 28 of the trigon-shaped hole 6. Each of the corners 28 can define a corner radius R9, measured from the corner axis 37 to the corner apex 39. The corner radii R9 can be in a range from about 0.0 mm to marginally smaller than R8 and further to about R8. The crests 56 and roots 58 of the plate threads 9 extend along respective splines that revolve about the central hole axis 22 helically along the trigon profile of the interior surface 24 between the upper plate surface 18 and the lower plate surface 20. Additionally, the interior surface 24, including the columns 26 as well as the corners 28, tapers inwardly toward the central hole axis 22 from the upper plate surface 18 toward the lower plate surface 20. Moreover, as shown, the plate threads 9 can circumferentially traverse the columns 26 and the corners 28 in an uninterrupted fashion (i.e., the plate threads 9 need not bottom-out in the corners 28). Accordingly, the plate threads 9 can transition smoothly and continuously between the column threads 54 and the portions of the threads 9 that traverse the corners 28.

The first surfaces 42 of each column 26 define a column length LC measured between the sides 44, 45 of the column 26. In the present embodiment, the column length LC can be substantially consistent within each column 26 as the thread path advances between the upper and lower surfaces 18, 20 of the plate 4. In such embodiments, the column length LC can also be referred to as a "side length" LC of the trigon-shaped hole 6. The columns 26 of the present embodiment can have substantially equivalent column lengths LC, thus providing the hole 6 with a substantially equilateral triangular shape, as shown. The column length LC can be in a range from about 0.010 mm to about 4.00 mm, and more particularly in a range from about 0.25 mm to about 3.25 mm, and more particularly in a range of about 0.50 mm to about 2.85 mm. For example, in a preferred embodiment, the column length LC can be in a range from about 0.20 mm to about 0.35 mm. In another embodiment, the column length LC can be in a range from about 0.50 mm to about 0.60 mm, and preferably in a range of about 0.530 mm to about 0.570. Alternatively, the column lengths LC of two or all of the columns can differ from one another. In further embodiments, the column length LC of one or more and up to all of the columns 26 can successively increase as the thread path advances from the upper surface 18 toward the lower surface 20 of the plate 4, thereby causing the corner radii R9 to progressively decrease toward the lower surface 20 of the plate 4.

Figure 6C:
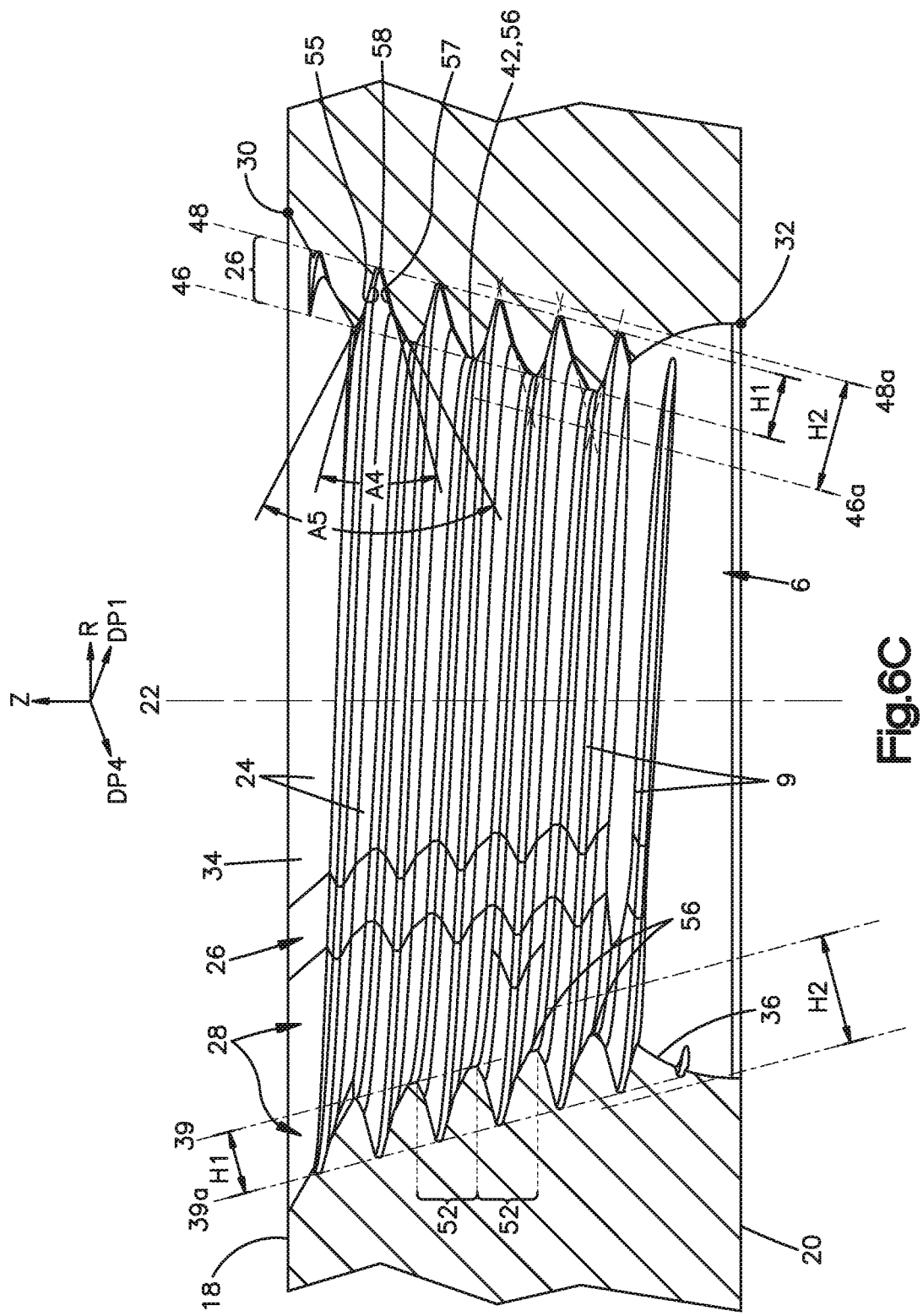
FIG. 6C is a sectional side view of the locking hole taken along section line 6C-6C shown in FIG. 6B, illustrating the threaded locking structure of the hole.

Referring now to FIG. 6C, the plate threads 9 of the present embodiment can have a substantially consistent thread profile and thread height H1 as the threads 9 revolve along their thread path(s) about central hole axis 22, including along one or more revolutions. Thus, the thread height H1 can be substantially equivalent at the crest centerlines 46 of the columns 26 and at the corner apices 39, and also at the portions of the columns 26 and corners 28 therebetween. As shown in FIG. 6C, the corner apices 39 can be defined along the crests 56 of the threads 9, and a corner root axis 39a can extend linearly in a manner intersecting the roots 58 of the threads 9. At the corner apex 39, the thread height H1 is measured between the crest 56 (or the corner apex 39) and the root 58 (or the corner root axis 39a) along a direction DP4 perpendicular to the corner apex 39. In the present embodiment, each corner apex 9 and corner root axis 39a shares a common axial plane with the crest trajectory axis 46 and root trajectory axis 48 of an opposed one of the columns 26. Thus, with respect to the thread profile, the recess apex 39 is analogous to the crest trajectory axis 46, while the corner root axis 39a is analogous to the root trajectory axis 48. Accordingly, the crest trajectory axis 46 and the corner apex 39 can each be oriented at angle A2 described above, while the root trajectory axis 48 and the corner root axis 39a can each be oriented at angle A3 described above.

Moreover, the plate threads 9 of the present embodiment can also define a helical series of thread segments 52 having substantially consistent thread profiles along the thread path(s), including at the crest centerlines 46, at the corner apices 39, and locations circumferentially therebetween. In particular, the crests 56, roots 58, and upper and lower flanks 55, 57 of the threads 9 of the present embodiment can each have substantially consistent profiles along the thread path(s). It is to be appreciated that, in the present embodiment, the crests 56 can define crest profiles 56a, the roots can define root profiles 58a, and the upper and lower flanks 55, 57 can define respective upper and lower flank profile portions 55a-c, 57a-c (including optional transition portions), each in a similar manner as those described above with reference to FIG. 2G. Accordingly, the threads 9 at the columns 26 and corners 28 can be multi-angle threads, including dual-angle threads, particularly with first and second thread angles A4, A5 as described above. Alternatively, as shown in FIGS. 16A through 16H, the plate thread profiles of the trigon-shaped VA locking hole can be configured similarly to the single-angle threads described above with reference to FIGS. 5B through 5D, or can include arcuate thread profiles as described above with reference to FIGS. 2H and 2I. Moreover, the thread segments 52 of the column threads 54 also define a reference thread height H2 measured between a crest reference axis 46a and a root reference axis 48a, which are also defined in the manner described above with reference to FIG. 2G. It should be appreciated that the threads 9 of the corners 28 also define a reference height H2, which, at the corner apex 39, is measured along direction DP4 between an un-truncated crest reference point and an un-relieved root reference point, which are defined by the thread profiles at the corners in an analogous manner as described above with reference to FIG. 2G. It should also be appreciated that the thread height H1 and reference thread height H2 can be substantially equivalent at the columns 26 and corners, respectively, and can also be within the respective ranges described above.

It is to be appreciated that the trigon-shaped VA locking hole 6 described above increases the total contact area between the plate threads 9 and the screw head threads 29, while also providing the plate threads 9, particularly the column threads 54 thereof, with a measure of the favorable deformation qualities described above. In this manner, the locking interface of the plate threads 9 and screw head threads 29 can provide the locking screw 8 with an overall cantilever strength (i.e., resistance to a force applied perpendicularly to the central axis 23 of the screw 8) greater than that of the preceding embodiments, while also causing most if not substantially all of the thread deformation at the locking thread interface to be imparted plastically and elastically to the plate threads 9. The inventors have discovered, surprisingly and unexpectedly, through their own extensive testing, that the plate threads 9 of the present embodiment and the screw head threads 27 described above have a locking thread interface that, at certain angulations, has a cantilever strength that approaches and can even exceed the ultimate bending strength of the screw 8. For example, the inventors' tests have shown that a VA locking screw 8, configured as described above and fully seated in the VA locking hole 6 of the present embodiment at an angulation from nominal to about 6 degrees, will fail (i.e., break, or bend to an extent categorized as failure of a VA locking screw) at a location of the screw shaft 25 proximate the distal end 72 of the head 27. Stated differently, at the foregoing conditions, the screw shaft 25 will fail before the locking thread interface fails. Moreover, at a fully seated insertion at angulations in a range from about 6 degrees to about 15 degrees, the cantilever strength of the locking thread interface decreases to within a range of about 30 percent to 40 percent of the ultimate bending strength of the screw 8. These cantilever strengths of the locking thread interface, particularly at angulation, represent significant improvements over prior art VA locking hole-screw systems.

Figure 7A:
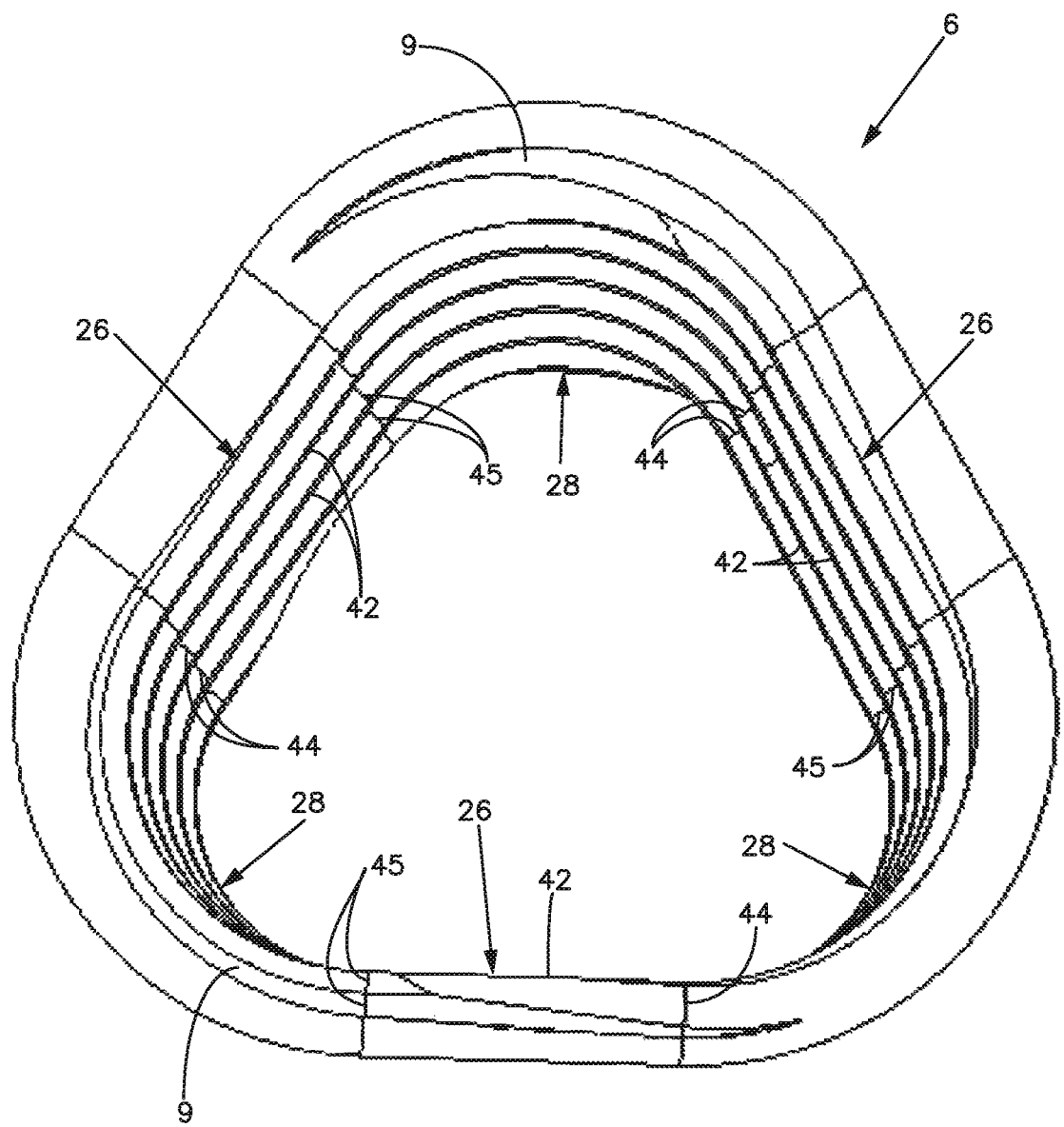
FIG. 7A is a perspective view of another locking hole, which has a trigon horizontal hole profile with smaller corner radii relative to the locking hole of FIG. 6A, and which includes a threaded locking structure defined by an interior surface of the locking hole, according to a further embodiment of the present disclosure.
Figure 7B:
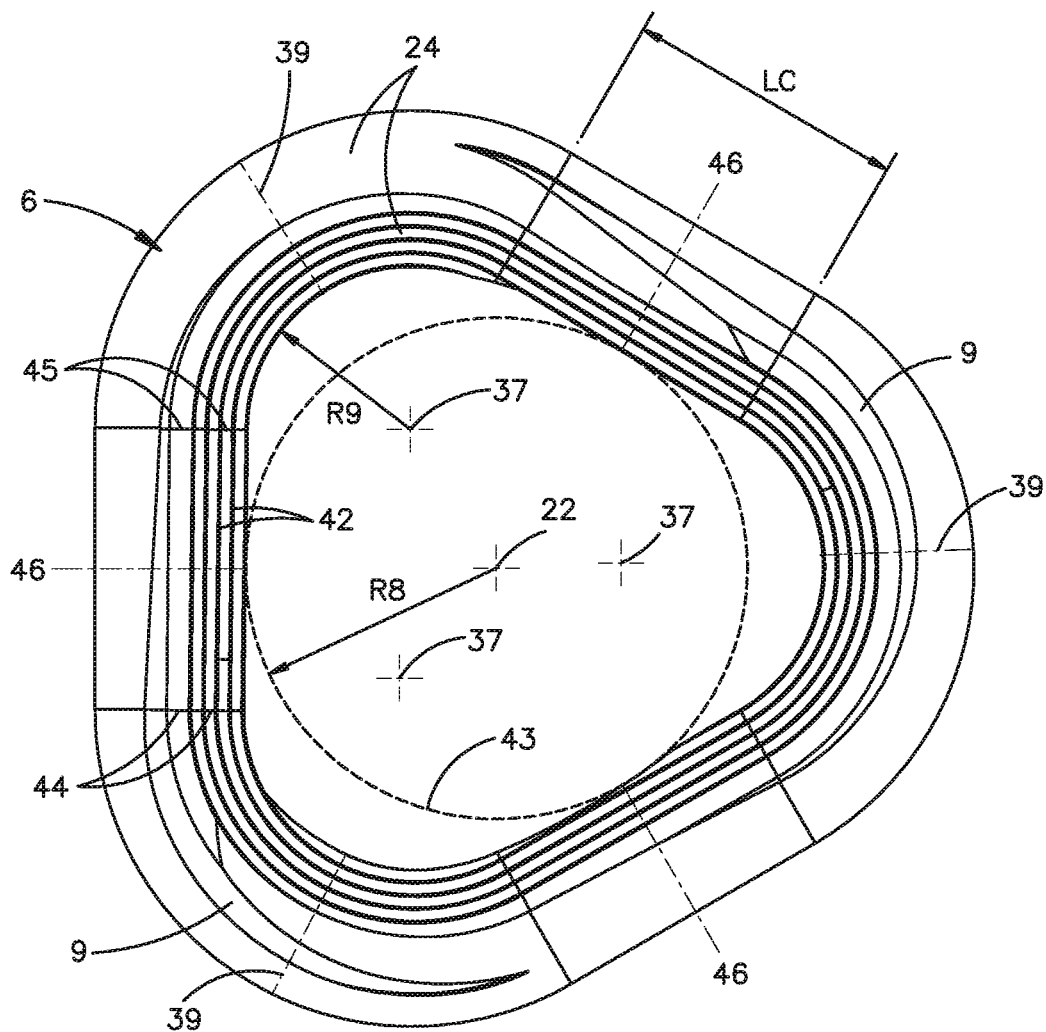
FIG. 7B is a top view of the locking hole illustrated in FIG. 7A.

Referring now to FIGS. 7A and 7B, in further embodiments, the corner radii R9 of the polygonal-shaped (e.g., trigon-shaped) VA locking hole 6 can be reduced and the column length LC (i.e., the length of the first surfaces 42 of the thread columns 26, as measured between the sides 44, 45) can be increased relative to the hole 6 shown in FIGS. 6A through 6C, thereby providing the polygonal hole 6 of the present embodiment with sharper corners 28, and thus a more profound polygonal (e.g., triangular) shape. Accordingly, the plate threads 9, and thus the crests 56 and roots 58 thereof, can extend along a thread path that also has a more profound triangular shape as it traverses the columns 26 and corners 28. The other parameters of the trigon-shaped hole 6 can be maintained as described above with reference to FIGS. 6A through 6C, including the radius R8 of the reference circle 43, the axial taper angles A2, A3, the thread profiles, the thread angles A4, A5, the thread height H1, and the reference height H2. Alternatively, one or more of these other parameters can be adjusted as needed.

It is to be appreciated that reducing the corner radii R9 and increasing the length of the first surfaces 42 of the polygonal-shaped VA locking hole 6 effectively distributes forces between the plate threads and the screw head threads 29 in a more tangential manner relative to the force distribution of the polygon-shaped locking hole 6 described above with reference to FIGS. 6A through 6C.

Figure 8A:
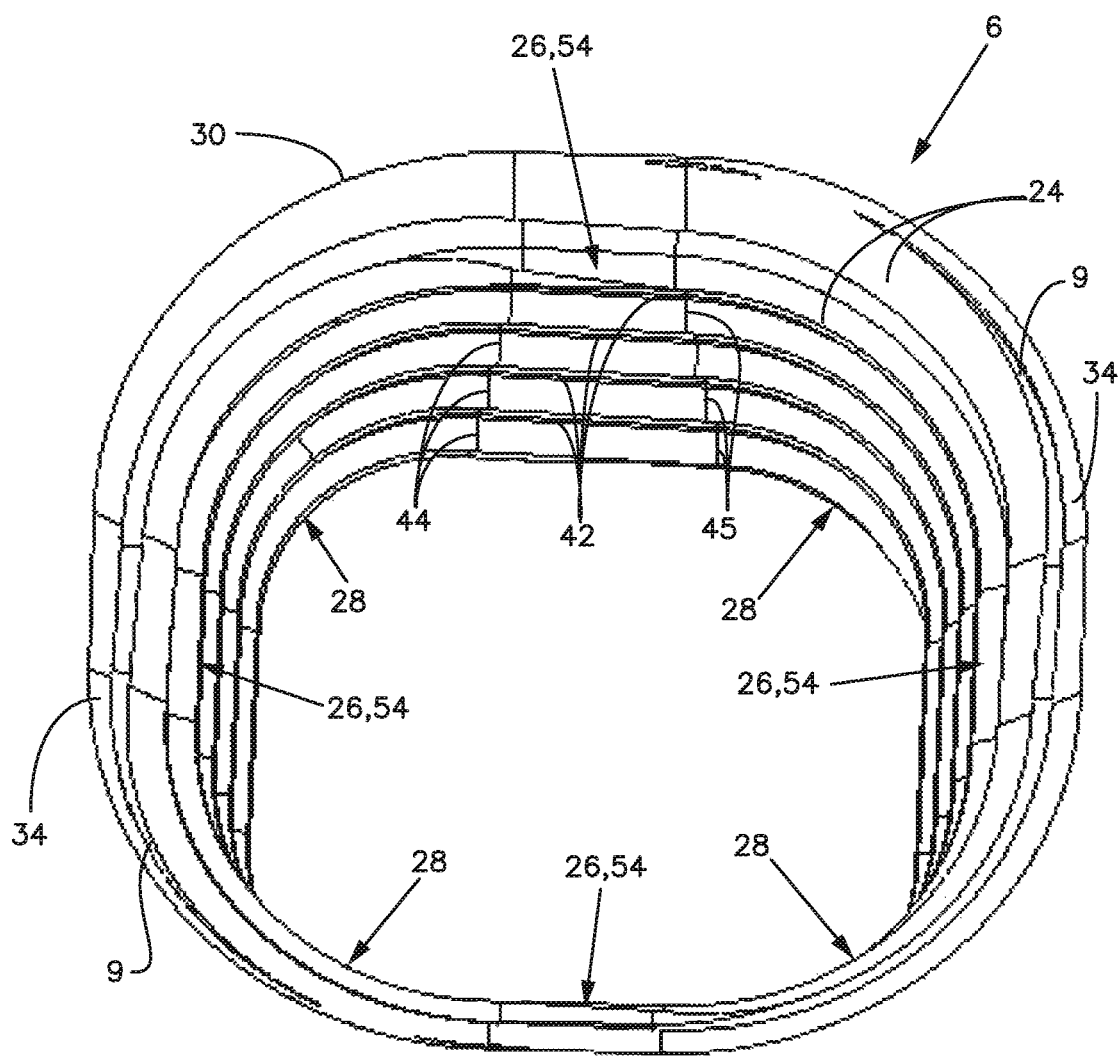
FIG. 8A is a perspective view of another locking hole, which has a tetragon horizontal hole profile, and which includes a threaded locking structure defined by an interior surface of the locking hole, according to yet another embodiment of the present disclosure.
Figure 8B:
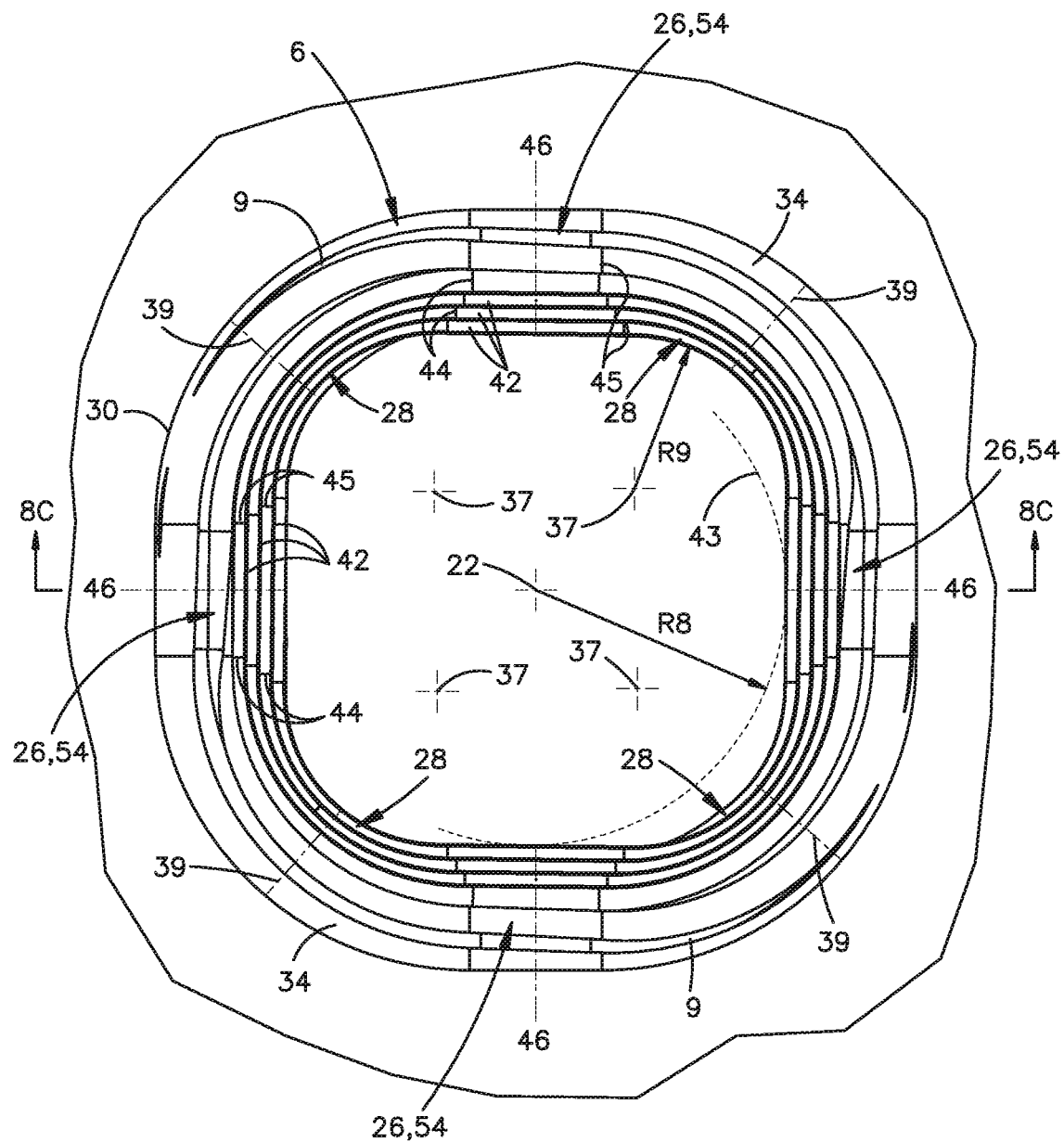
FIG. 8B is a top view of the locking hole illustrated in FIG. 8A.

Referring now to FIGS. 8A and 8B, in additional embodiments, the VA locking hole 6 can have a polygonal horizontal profile in the shape of a tetragon (i.e., a four-sided polygon). Accordingly, the interior surface 24 of the plate body 5 within the hole 6 defines a corresponding tetragon horizontal profile. Additionally, the upper perimeter 30, the one or more lead in surfaces 34, the one or more undercut surfaces 36, and the lower perimeter 34 of the hole 6 preferably can also have corresponding tetragon horizontal profiles.

As in the polygonal-shaped holes described above, the first surfaces 42 of the columns 26 have linear horizontal profiles that tangentially intersect the reference circle 43. In particular, each of the first surfaces 42 intersects the reference circle 43 substantially at the crest trajectory axis 46. The radius R8 of the reference circle 43 can be within the ranges described above. The corners 28 extend tangentially from the first and second sides 44, 45 of each column 26, such that the first surfaces 42 define the sides of the tetragon extending between the corners 28. In the present embodiment, the corner radii R9 can be in any of the ranges described above with reference to FIGS. 6A through 7C.

In the present embodiment, the length of the first surfaces 42, and thus the distance between the sides 44, 45 of each column 26, can successively increase as the thread path advances toward the lower surface 20 of the plate 4. Accordingly, the respective engagement forces between the plate threads 9 and the screw head threads 29 can be progressively distributed in a more tangential manner as the screw head 27 advances within the hole 6, including at an angulated insertion trajectory. Alternatively, the first surfaces 42 of each column 26 can have a substantially consistent length along the thread path.

Similar to the manner described above, the crests 56 and roots 58 of the plate threads 9 extend along respective splines that revolve about the central hole axis 22 helically along the tetragon profile of the interior surface 24 between the upper plate surface 18 and the lower plate surface 20. Additionally, the interior surface 24, including the columns 26 as well as the corners 28, tapers inwardly toward the central hole axis 22 from the upper plate surface 18 toward the lower plate surface 20. Moreover, as shown, the plate threads 9 can circumferentially traverse one or more an up to each of the corners 28 in an uninterrupted fashion (i.e., the plate threads 9 need not bottom-out in the corners 28).

Figure 8C:
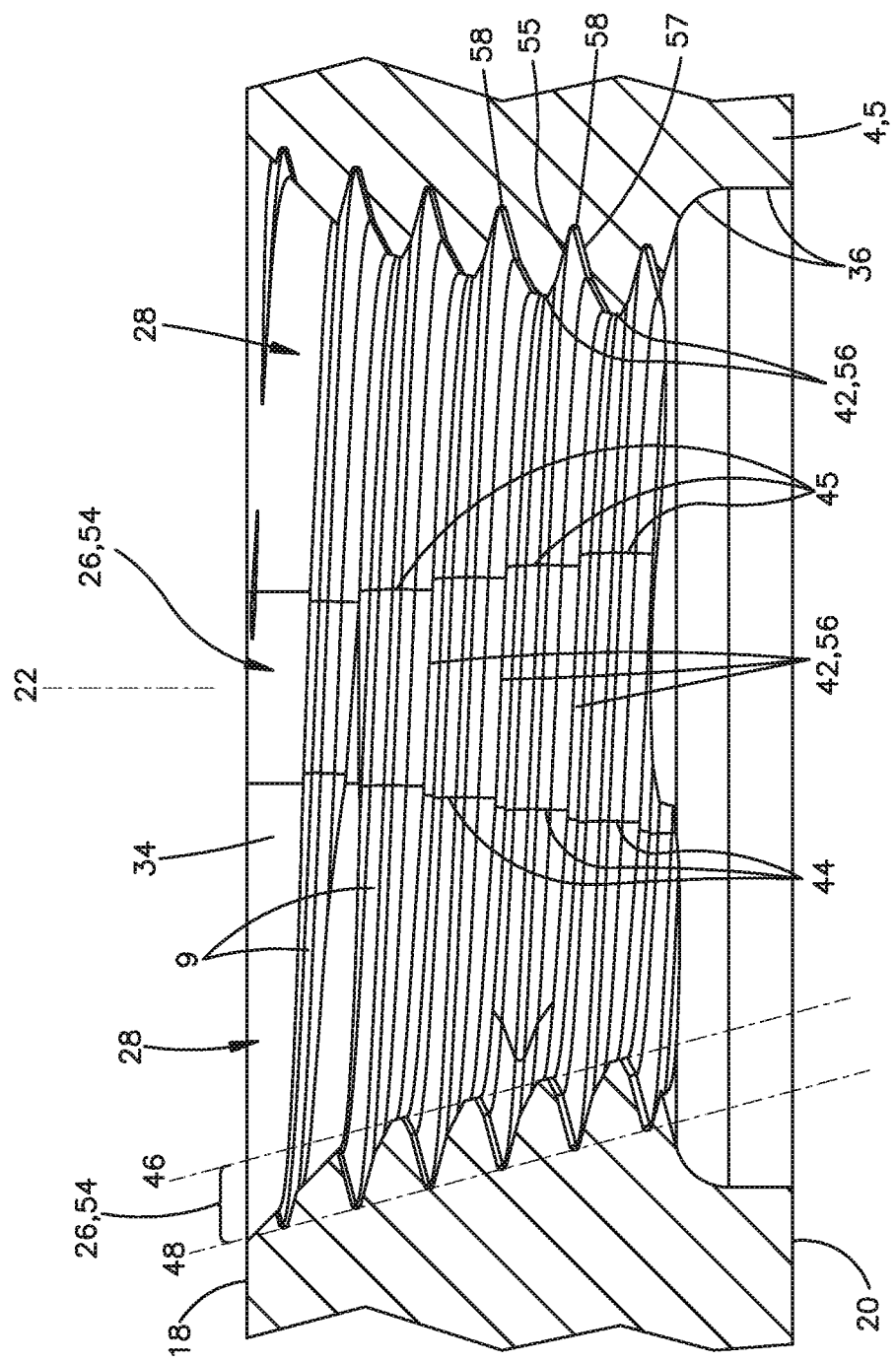
FIG. 8C is a sectional side view of the locking hole taken along section line 8C-8C shown in FIG. 8B, illustrating the threaded locking structure of the hole.

Referring now to FIG. 8C, the plate threads 9 of the present embodiment can define thread profiles similar to those described above with reference to FIG. 2G, as well as with reference to the trigon-shaped VA locking holes 6. Moreover, it should be appreciated that the thread profiles, including the crest 56, roots 58, and flanks 55, 57 thereof, can be substantially consistent along the thread path, including at the columns 26 and at the corners 28, as described above with reference to the trigon-shaped holes 6. Accordingly, the threads 9 can have a substantially consistent thread height H1, as well as a substantially consistent reference height H2, along the thread path(s). The thread height H1 and reference height H2 can be defined as described above.

As with the trigon-shaped VA locking holes 6 described above, the tetragon-shaped holes 6 of the present embodiment effectively increase the total contact area between the plate threads 9 and the screw head threads 29, while also providing the threads 9 with a measure of the favorable deformation qualities described above. In this manner, the locking thread interface of the tetragon-shaped hole 6 can exhibit an overall cantilever strength greater than that of the embodiments described above with reference to FIGS. 2A through 2G and 4A through 5D.

It should be appreciated that the VA locking holes 6 of the present disclosure can have other polygonal horizontal profiles, including pentagonal (i.e., five sides 42 and five corners 28), hexagonal (i.e., six sides 42 and six corners 28), heptagonal (i.e., seven sides 42 and seven corners 28), octagonal (i.e., eight sides 42 and eight corners 28), nonagonal (i.e., nine sides 42 and nine corners 28), decagonal (i.e., ten sides 42 and ten corners 28), etc., up to a number of sides 42 that substantially defines a circular horizontal hole profile. It should also be appreciated that in any of the polygonal-shaped VA locking holes 6 of the present application, the threads 9 can extend in continuous and un-interrupted fashion along the columns 26 and corners 28, or optionally the threads 9 can bottom-out in the corners 28. Moreover, the thread profiles in any of the non-circular (e.g., polygonal-shaped) VA locking holes 6 of the present application can be single-angle (e.g., similar to that described above with reference to FIGS. 5B through 5D), dual- or additional multi-angle, or arcuate, as described above.

In further embodiments, the VA locking holes 6 of the present disclosure can have a horizontal hole profile according to any of the shapes described above, wherein the horizontal hole profile itself revolves about the central hole axis 22 from the upper plate surface 18 toward the lower plate surface 20, thereby defining a twisted or spiraling hole profile geometry. Moreover, the VA locking holes 6 of the present disclosure can extend obliquely through the bone plate 4, such that the central hole axis 22 is oriented at a non-orthogonal angle relative to one or both of the upper plate surface 18 and the lower plate surface 20. Furthermore, the upper and lower plate surfaces 18, 20 of the bone plate 4, or at least portions thereof, need not be flat, but can instead be bent, contoured, textured, roughened, dimpled, bulgy, or have any other geometry for providing an enhanced interface or fit with the anatomy of the underlying bone. In additional embodiments, the VA locking holes 6 of the present disclosure can have multiple horizontal hole profiles (i.e., hole shapes) along the central hole axis 22. For example, the internal surface 24 within any of the VA locking holes 6 can optionally include at least a first axial portion adjacent the upper plate surface 18 and defining a first horizontal hole profile and at least a second axial portion extending axially between the first axial portion and the lower plate surface 20 and defining a second horizontal hole profile that is different than the first horizontal hole profile. By way of one non-limiting example, the first axial portion of the interior surface 24 can extend from the upper perimeter 30 of the hole 6 and can include the lead-in surface(s) 34 and the threads 9 having a fully-developed thread-form, while the second axial portion of the interior surface 24 can include the undercut surface 36 and can extend to the lower perimeter 32 of the hole 6. The first axial portion can have any of the circular or non-circular horizontal profiles described herein (including any of the polygonal profiles), while the second axial portion can have any of the foregoing profiles that is different than the first axial portion. In such multi-profile hole embodiments, the interior surface 24 can also include a transition portion between the first and second axial portions, in which the horizontal hole profile transitions between the first and second horizontal hole profiles. It should be appreciated that the interior surface 24 can also include one or more additional axial portions each having a horizontal hole profile that is different than at least one other of the horizontal hole profiles within the VA locking hole 6.

Figure 9:
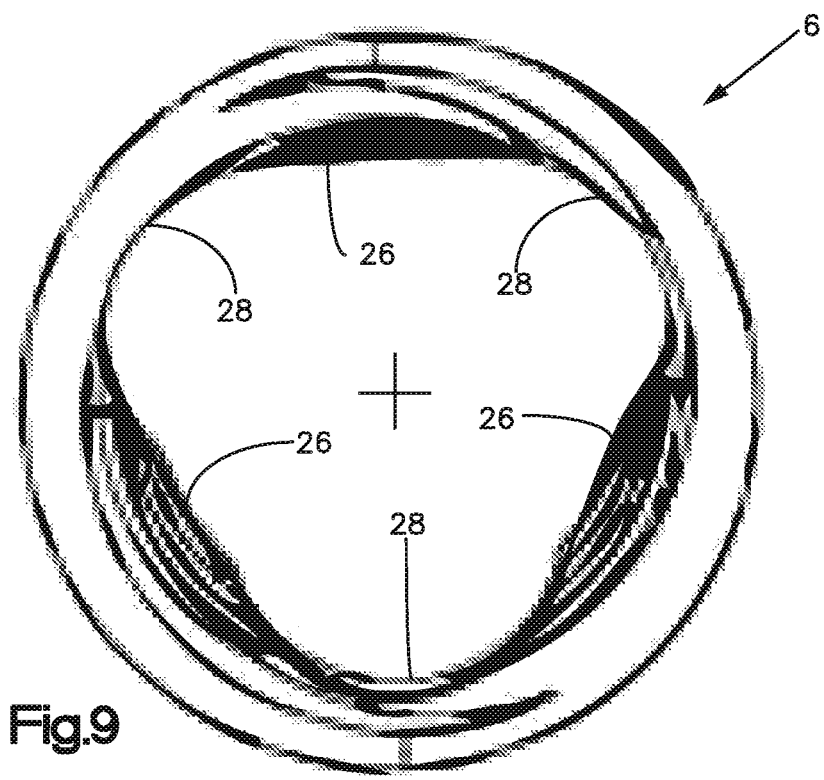
FIG. 9 is a top view of a locking hole having three (3) threaded locking structures and three (3) recesses, and otherwise being configured similarly to the locking hole shown in FIG. 2D.
Figure 10:
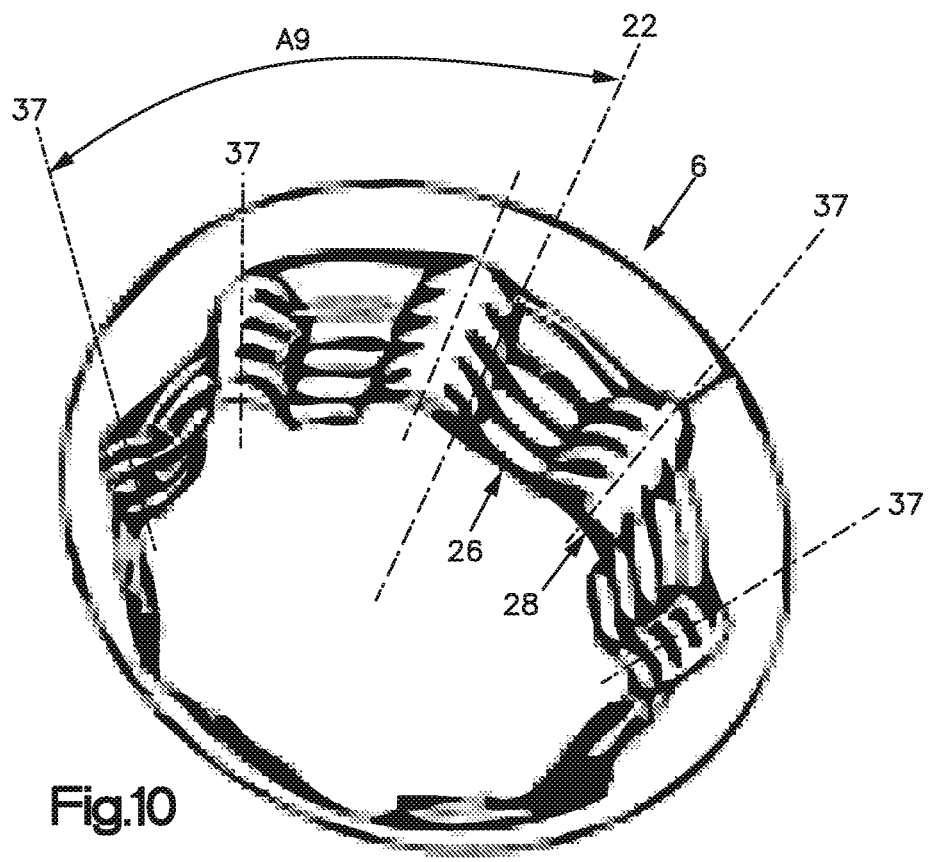
FIG. 10 is a perspective view of another locking hole having eight (8) threaded locking structures and eight (8) recesses, according to another embodiment of the present disclosure.

Furthermore, as mentioned above, the design of the VA locking hole 6 is not limited by the number of columns and recesses or corners 28. Accordingly, by way of a non-limiting example, the hole 6 can have three (3) columns 26 circumferentially spaced between three (3) recesses 28, as shown in FIG. 9. Moreover, the hole 6 can alternatively have more than four (4) each of columns 26 and recesses 28. In further embodiments, the VA locking hole 6 can have five (5), six (6), seven (7), eight (8), nine (9), ten (10), eleven (11), twelve (12), thirteen (13), fourteen (14), fifteen (15), sixteen (16), or more than sixteen (16) each of columns 16 and recesses 28. By way of another non-limiting example, FIG. 10 shows a VA locking hole 6 having eight (8) columns 26 circumferentially spaced between eight (8) recesses 28. Additionally, as shown, the recesses 28 can define central recess axes 37 that are oriented at an acute angle A9 with respect to the central hole axis 22. In such embodiments, the angle A9 can be substantially equivalent to the angle A2 at which the crest trajectory axis 46 is oriented, as described above with reference to FIG. 2E.

It should also be appreciated that any of the VA locking holes 6 described above, including any features thereof (such as the thread geometries, by way of a non-limiting example), can be incorporated into a combination hole (also referred to as a "combi-hole") with another hole, such as a compression hole, within the bone plate 4. With reference to FIGS. 11A through 15B and 17 through 20, embodiments of a combi-hole 90 will be described in which the VA locking hole 6 portion thereof is trigon-shaped, similar to the embodiments described above with reference to FIGS. 6A through 7B.

Figure 11A:
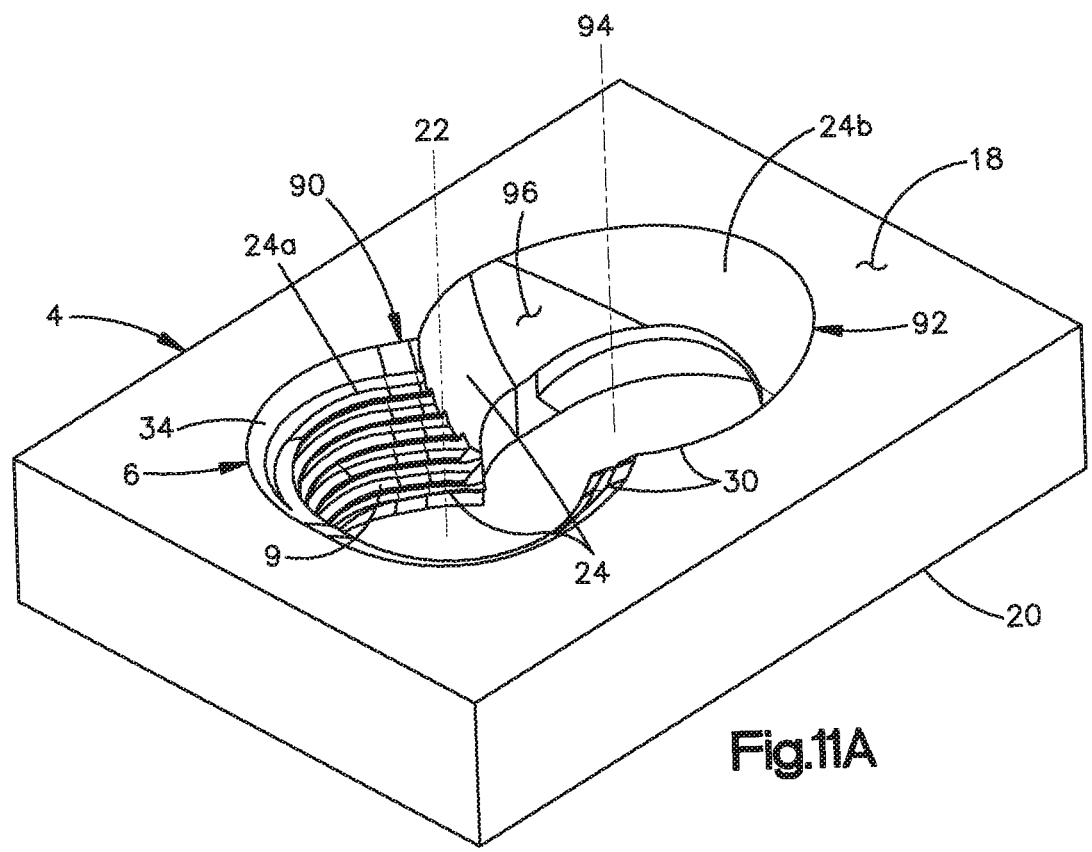
FIG. 11A is a perspective view of a bone plate having a combination hole that includes a trigon locking hole intersected by a compression hole, according to another embodiment of the present disclosure.
Figure 11B:
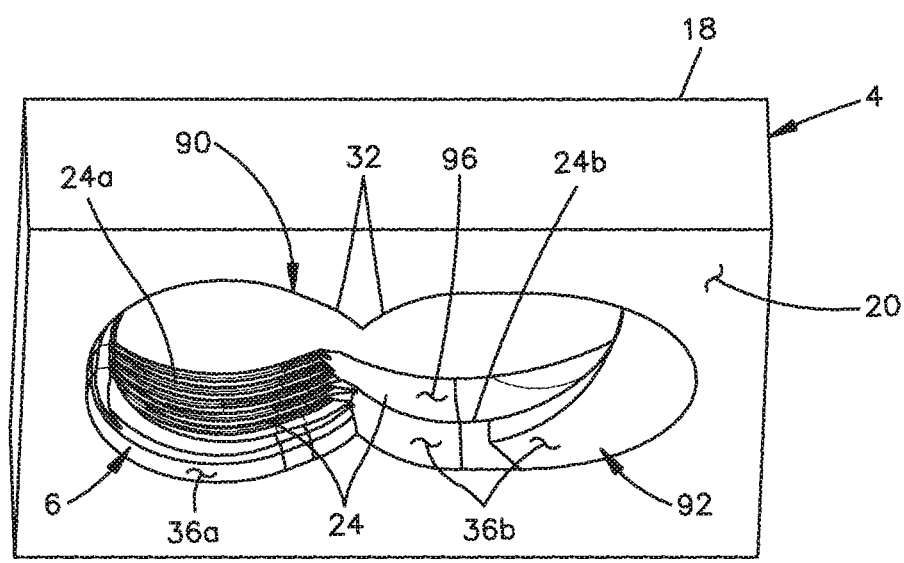
FIG. 11B is another perspective view of the bone plate illustrated in FIG. 11A.

Referring now to FIGS. 11A and 11B, one example of such a combi-hole 90 includes a compression hole 92 in combination with the VA locking hole 6, such that the VA locking hole 6 and the compression hole 92 overlap one another and are open to each other. In this manner, interior surface 24 of the plate body 5 can define both the VA locking hole 6 and the compression hole 92, each extending from the upper plate surface 18 to the lower plate surface 20. An upper perimeter 30 of the combi-hole 90 can define an upper opening to each of the VA locking hole 6 and the compression hole 92. Similarly, a lower perimeter 32 of the combi-hole 90 can define a lower opening to each of the VA locking hole 6 and the compression hole 92. It should be appreciated that the VA locking hole 6 and the compression hole 92 can be referred to as respective "portions" of the combi-hole 90 can each be referred to as a respective "hole." Moreover, the portion of the interior surface 24 that defines the VA locking hole 6 can be referred to as a first or "locking" surface 24a. Similarly, the portion of the interior surface 24 of the combi-hole 90 that defines the compression hole 92 can be referred to as a second surface 24b. The locking surface 24a can define one or more lead-in surfaces 34 that taper axially downward from the upper perimeter 30 to plate threads 9 in the VA locking hole 6.

The second surface 24b can define a compression surface 96 of the compression hole 92. At least a portion up to an entirety of the compression surface 96 can be unthreaded. Accordingly, the compression surface 96 defines a bearing surface against which the unthreaded compression head of a compression screw is configured to bear so as to apply a compressive force against the bone plate 4 toward the underlying bone. In one example, the compression surface 96 can be concave in the axial direction with respect to a central hole axis 94 of the compression hole 92. For instance, the compression surface 96 can be dish shaped or semi-spherical. Alternatively, the compression surface 96 can have a linear profile that tapers radially inwardly toward central hole axis 94 from the upper plate surface toward the lower plate surface 20. The locking surface 24a can define a first undercut surface 36a that tapers axially upward from the lower perimeter 32 of the combi-hole 90 to the plate threads 9. The second surface 24b can define a second undercut surface 36b that tapers axially upward from the lower perimeter 32 to the compression surface 96.

Figure 17:
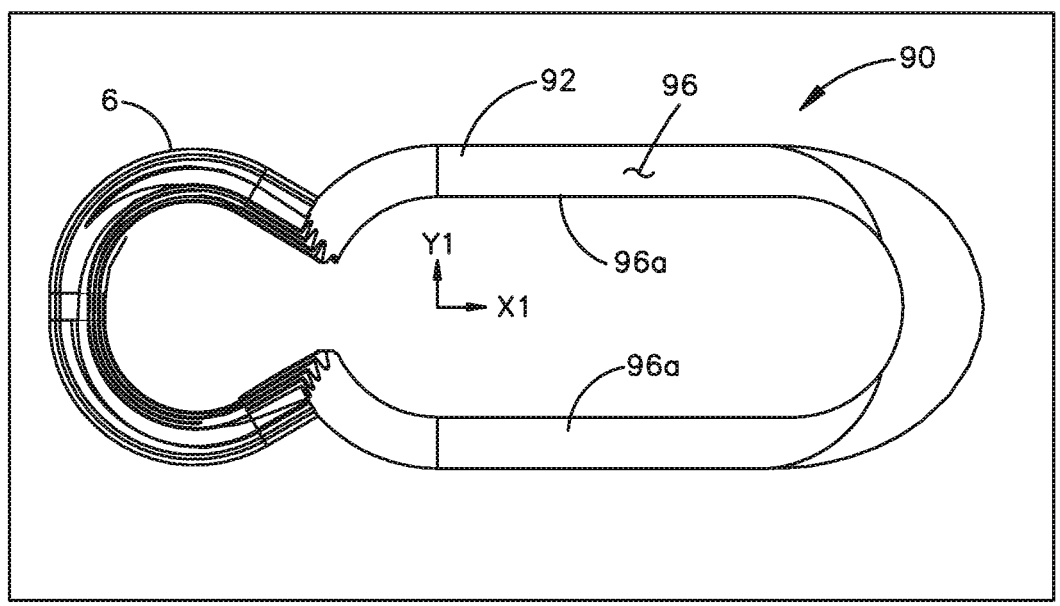
FIG. 17 is a top view of a combination hole having an elongated compression hole, according to another embodiment of the present disclosure.

Referring now to FIGS. 11C and 11D, in the combi-hole 90, the VA locking hole 6 and the compression hole 92 can be open to each other along a direction X1, which is preferably oriented along an intersection axis 97 that intersects the central hole axis 22 of the VA locking hole 6 and a central hole axis 94 of the compression hole 92. Direction X1 can be referred to as the "longitudinal hole direction" X1 and can be oriented along the longitudinal direction X of the plate 4, or along any suitable alternative direction as desired. The compression hole 92 can be elongate along the longitudinal hole direction X1. For example, the compression hole 92 can have a horizontal hole profile that is substantially elliptical. In such embodiments, the intersection axis 97 can be coextensive with the major axis of the elliptical horizontal hole profile. Moreover, the central axis 94 of the compression hole 90 can be located at a midpoint between the foci of the elliptical horizontal hole profile. The combi-hole 90 defines a first axis separation distance LA1 between the central axes 22, 94 of the VA locking hole 6 and the compression hole 92 along the longitudinal hole direction X1. It should be appreciated that the compression hole 92 can have non-elliptical horizontal hole profiles in other embodiments. For example, the compression hole 92 can have a circular horizontal hole profile. As shown in FIG. 17, the combi-hole 90 can optionally have a compression hole 92 having semi-circular ends and elongate sides 96a extending therebetween along the longitudinal hole direction X1, or similar such geometries.

For purposes of this disclosure, the central axis 94 of the compression hole 92 extends through the geometric midpoint of a theoretical completed version of the compression hole 92. Stated differently, central axis 94 extends through what could be considered the geometric midpoint of the compression hole 92 if the compression hole 92 were not interrupted by the VA locking hole 6. The intersection axis 97 can also intersect a midpoint 46 of a first of the columns or "sides" 26a of the trigon VA locking hole 6. Stated differently, the intersection axis 97 can intersect the crest centerline 46 of the first column 26a of the trigon VA locking hole 6, which column 26a can be referred to as the "base" column 26a. In such embodiments, the second and third columns 26b, 26c of the trigon VA locking hole 6 can be equidistantly spaced from the intersection axis 97 along a lateral hole direction Y1 oriented perpendicular to the longitudinal hole direction X1. The locking surface 24a and the second surface 24b can intersect one another along an intersection boundary 119. In particular, a first portion of the intersection boundary 119 on a first side of the intersection axis 97 is separated from a second portion of the intersection boundary 119 on a second side of the intersection axis 97 by a gap 124 (FIG. 11C) that is open to the trigon VA locking hole 6 and the compression hole 92. The gap 124 defines a minimum gap distance G (FIG. 11D) measured along the lateral hole direction Y1. The interior surface 24 can also define a hole intersection zone 120 in which the intersection boundary 119 is located.

Referring now to FIGS. 11E and 11F, the intersection boundary 119 can be defined by interface edges 122 between the locking surface 24a and the second surface 24b. In particular, the interface edges 122 include edges between the plate threads 9 and the compression surface 96, which edges 122 tend to be abrupt and/or sharp as a result of the process(es) by which the combi-hole 90 is formed. Accordingly, the interior surface 24 within the hole intersection zone 120 is preferably adapted to reduce the abruptness and/or sharpness of the interface edges 122 to avoid, minimize, or at least reduce contact between such abrupt and/or sharp edges 122 of the plate threads 9 and surfaces of the screw head 27, such as the described screw head threads 29. One way to achieve this is to truncate, chamfer, bevel, or otherwise trim the interior surface 24 within the hole intersection zone 120 to define relief surfaces 126 therein. The relief surfaces 126 can be planar and can be parallel with the intersection axis 97, although other relief configurations are within the scope of the present disclosure.

The interface edges 122 can be spaced from a reference point along the central axis 22, such as an axial midpoint 22a thereof between the upper and lower surfaces 18, 20 of the plate 4. The axial midpoint 22a coincides with the location at which the central axis 22 intersects a reference plane M that is orthogonal to the central hole axis 22 and located at the vertical center of the VA locking hole 6, similarly as described above with reference to FIG. 2E. Thus, the axial midpoint 22a is located at what could be considered the geometric midpoint of the VA locking hole 6 if it weren't intersected by the compression hole 92. The VA locking hole 6 can define a minimum straight line distance D1 between the axial midpoint 22a and the nearest interface edge 122 of the plate threads 9, which in the present embodiment can be located at a crest 56 or, for example, at an upper flank 55 near a crest truncated by a relief surface 126. Thus, the relief surfaces 126 can be configured to increase the minimum straight line distance D1 to the intersection boundary 119. The VA locking hole 6 can also define a maximum straight line distance D2 between the axial midpoint 22a and the furthest interface edge 122 of the plate threads 9, which in the present embodiment can be located at a root 58 adjacent the lead-in surface 34. Although FIG. 11E depicts the intersection boundary 119 on only one lateral side of the combi-hole 90, it should be appreciated that the minimum and maximum straight line distances D1, D2 can be substantially similar at the intersection boundary 119 on the other lateral side of combi-hole 90 (i.e., the opposite side across the gap 124 along lateral hole direction Y1, as shown in FIG. 11C).

One of the challenges of providing a combi-hole 90 that incorporates the trigon VA locking holes 6 of the present disclosure is providing sufficient threaded engagement between the screw head threads 29 and plate threads 9 within the hole intersection zone 120 while also minimizing contact between the screw head 27 (particularly the screw head threads 29 thereof) and sharp edges of the plate threads 9 (particularly the interface edges 122 thereof), especially when the screw head 27 is angulated into the hole intersection zone 120 and thus also into the gap 124. Such an angulation A1 of about 15 degrees between the screw axis 23 and the central axis 22 of the trigon VA locking hole 6 is indicated in FIG. 11F. It should be appreciated that, alternatively or in addition to the relief surfaces 126, the combi-hole 90 geometry can be further adapted to avoid, minimize, or at least reduce contact between abrupt and/or sharp edges 122 of the plate threads 9 and the screw head 27 while also providing sufficient threaded engagement at high angulation A1 into the gap 124.

Figure 11G:
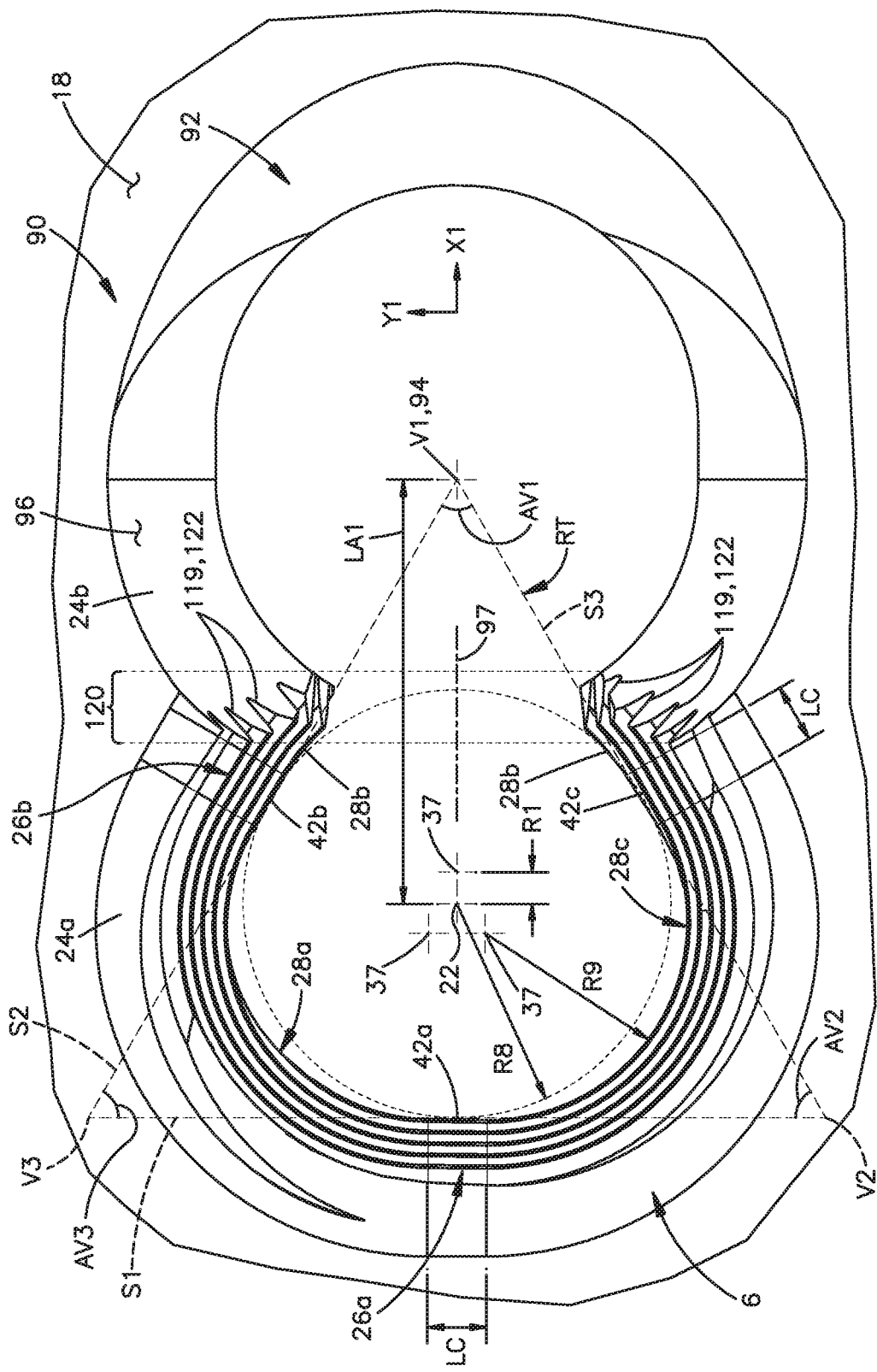
FIG. 11G is an enlarged top plan view of the combination hole illustrated in FIG. 11A.

Referring now to FIG. 11G, a discussion of such adaptations to the combi-hole 90 geometry can be assisted with reference to a reference triangle RT shown in dashed lines intersecting the reference circle 43 described above at the respective locations at which the reference circle 43 intersects the plate threads 9 and/or the crest trajectory axes 46 (see FIGS. 6B and 7B). The trigon VA locking hole 6 of the present embodiment is substantially equilateral, i.e., the columns 26 have substantially equidistance side lengths LC and the corners 28 have substantially equidistant corner radii R9. Accordingly, the reference triangle RT has first, second, and third sides S1, S2, S3 that are substantially equilateral and extend between first, second, and third vertices V1, V2, V3 that define respective angles AV1, AV2, AV3 each being about 60 degrees. The first vertex V1 is located opposite the first column 26a, the second vertex V2 is located opposite the second column 26b, and the third vertex V3 is located opposite the third column 26c. For purposes of the following disclosure: the first side S1 intersects the reference circle 43 tangentially at the same location at which the first surface 42 of the first column 26a intersects the reference circle 43; the second side S2 intersects the reference circle 43 tangentially at the same location at which the first surface 42 of the second column 26b intersects the reference circle 43; and the third side S3 intersects the reference circle 43 tangentially at the same location at which the first surface 42 of the third column 26c intersects the reference circle 43. The combi-hole 90 of the present embodiment is configured such that the first vertex V1 is substantially coincident with the central axis 94 of the compression hole 92, although in other embodiments the first vertex V1 can be offset from the central axis 94 of the compression hole 92. It should be appreciated that the central axes 22, 94 of the combi-hole 90 can be parallel (as shown), although they need not be parallel.

Exemplary dimensions for the combi-holes 90 of the present disclosure will now be described, particularly for a subset of combi-holes 90 configured to receive locking screws 8 having shafts 25 with major diameters from about 0.5 mm to about 10.0 mm, more particularly from about 1.0 mm to about 7.0 mm, and more particularly in a range from about 2.0 mm to about 4.0 mm, and preferably about 3.5 mm. It should be appreciated that the following dimensions are provided for exemplary purposes, and that these combi-hole sizes can be scaled upward or downward in size as needed depending on the desired medical treatment. The radius R8 of the reference circle 43 can be in a range from about 0.40 mm to about 5.50 mm, more particularly in a range from about 1.00 mm to about 3.00 mm, and more particularly in a range from about 1.40 mm to about 2.00 mm. The first axial separation distance LA1 can be in a range from about 0.80 mm to about 10.00 mm, and more particularly in a range from about 2.00 mm to about 5.00 mm, and more particularly in a range from about 3.00 mm to about 4.00 mm. The corner radii R9 can be in a range from about 0.20 mm to about 4.50 mm, and more particularly in a range from about 0.50 mm to about 2.00 mm, and more particularly in a range from about 0.75 mm to about 1.60 mm. The distance R1 between the central axis 22 and the corner axes 37 of the trigon VA locking hole 6 can be in a range from about 0.01 mm to about 3.50 mm, and more particularly in a range from about 0.15 mm to about 0.75 mm, and more particularly in a range from about 0.300 mm to about 0.325 mm. The column lengths LC can be in a range from about 0.01 mm to about 4.00 mm, and more particularly in a range from about 0.25 mm to about 3.25 mm, and more particularly in a range from about 0.50 mm to about 2.85 mm.

According to one non-limiting example of the present embodiment, the radius R8 of the reference circle can be about 2.050 mm, the first axial separation distance LA1 can be in a range from about 4.0 mm to 4.8 mm, the corner radii R9 of each corner 28a-c can be about 1.95 mm, the distance R1 between the central axis 22 and the corner axes 37 of the trigon VA locking hole 6 can be about 0.142 mm, and the first surfaces 42a-c of the columns 26a-c are each linear and have column lengths LC of about 0.2 mm to about 0.35, and more particularly from about 0.274 mm to about 0.276 mm. As shown, the hole intersection zone 120 can be located along the second corner 28b of the trigon VA locking hole 6 (i.e., the corner 28b opposite the base column 26a) and can optionally be entirely contained within the second corner 28b such that interface surfaces 122 between the VA locking hole 6 and compression hole 92 are entirely spaced from the second and third columns 26b, 26c.

Figure 12A:
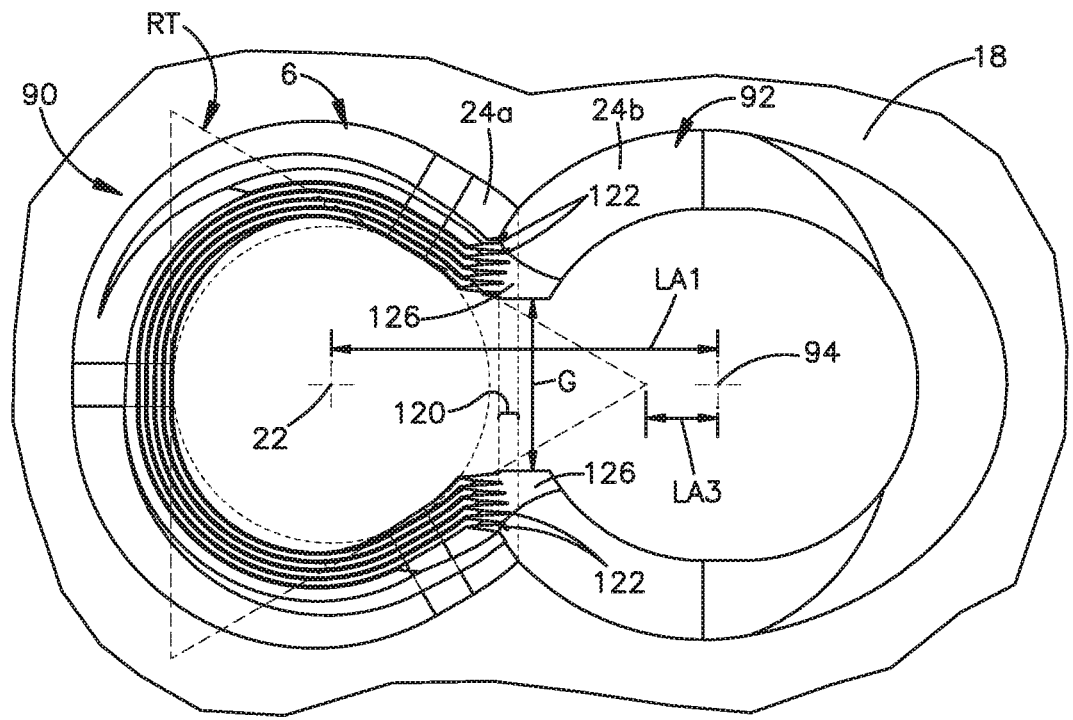
FIG. 12A is a top plan view of a combination hole having relief surfaces, according to another embodiment of the present disclosure.
Figure 12B:
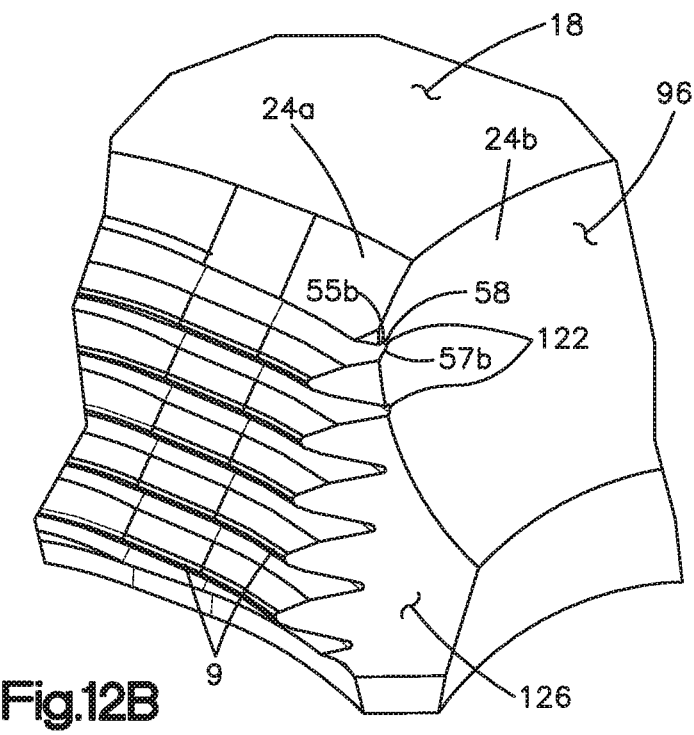
FIG. 12B is an enlarged perspective view of a relief surface of the combination hole illustrated in FIG. 12A.
Figure 14B:
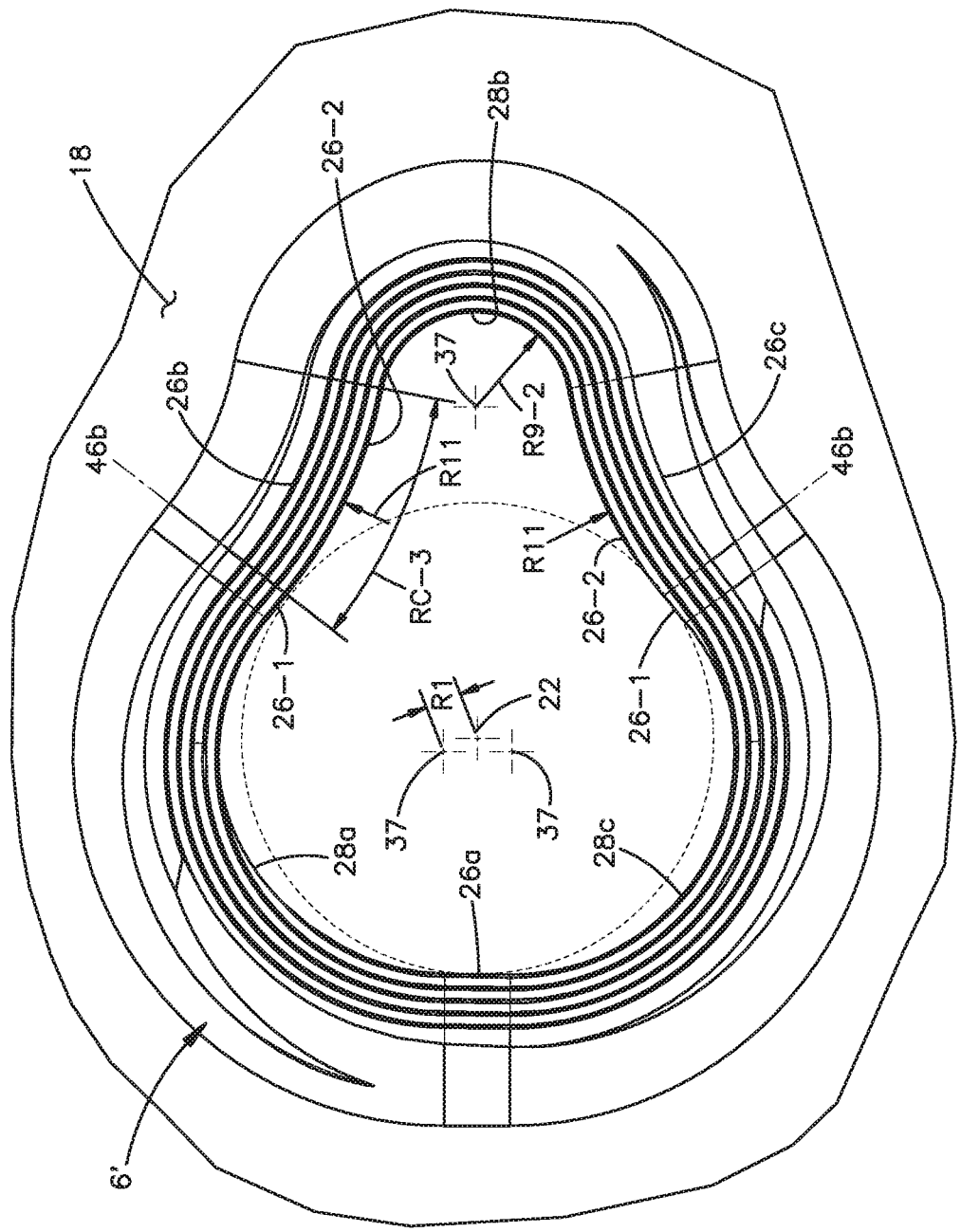
FIG. 14B is a top plan view of a base version of the locking hole employed in the combination hole illustrated in FIG. 14A.
Figure 15A:
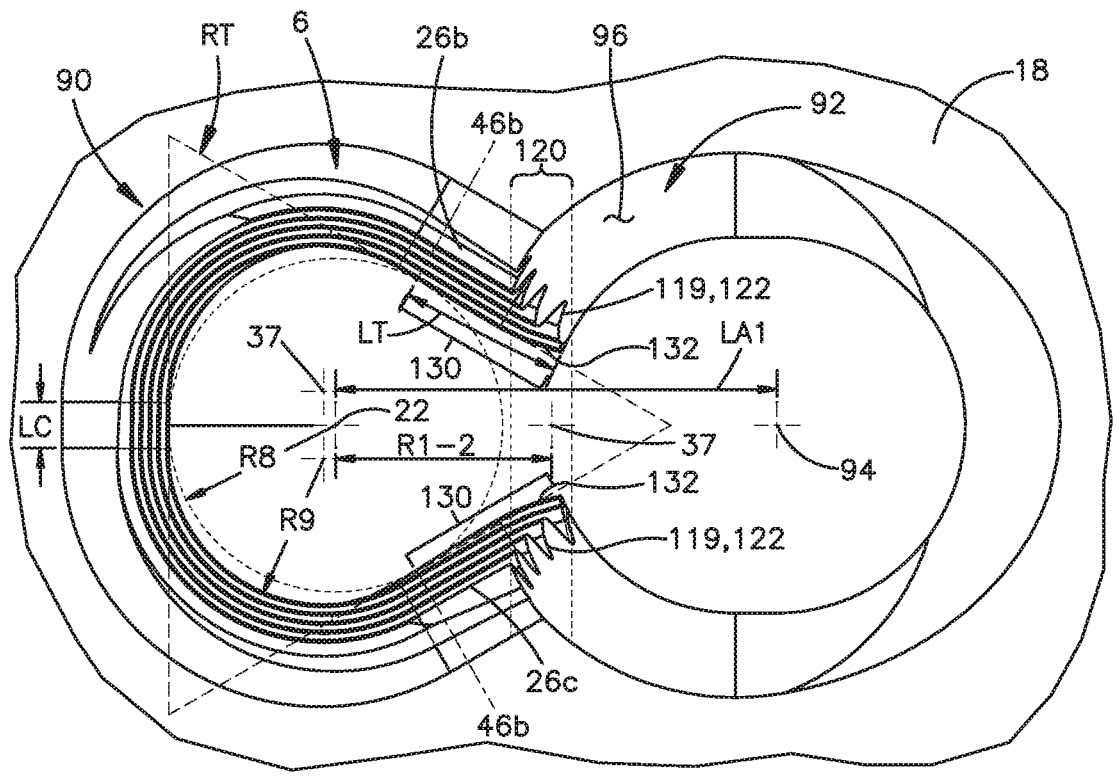
FIG. 15A is a top plan view of a combination hole having an arcuate, elongated and convex transition zone between the trigon locking hole and the compression hole, according to another embodiment of the present disclosure.
Figure 15B:
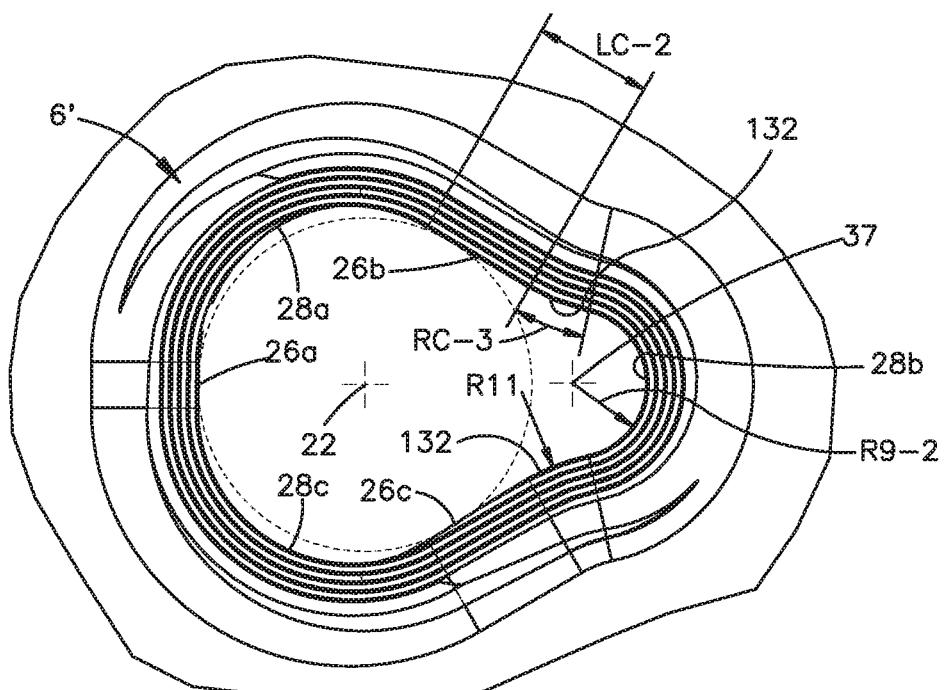
FIG. 15B is a top plan view of a base version of the locking hole employed in the combination hole illustrated in FIG. 15A.
Figure 16A:
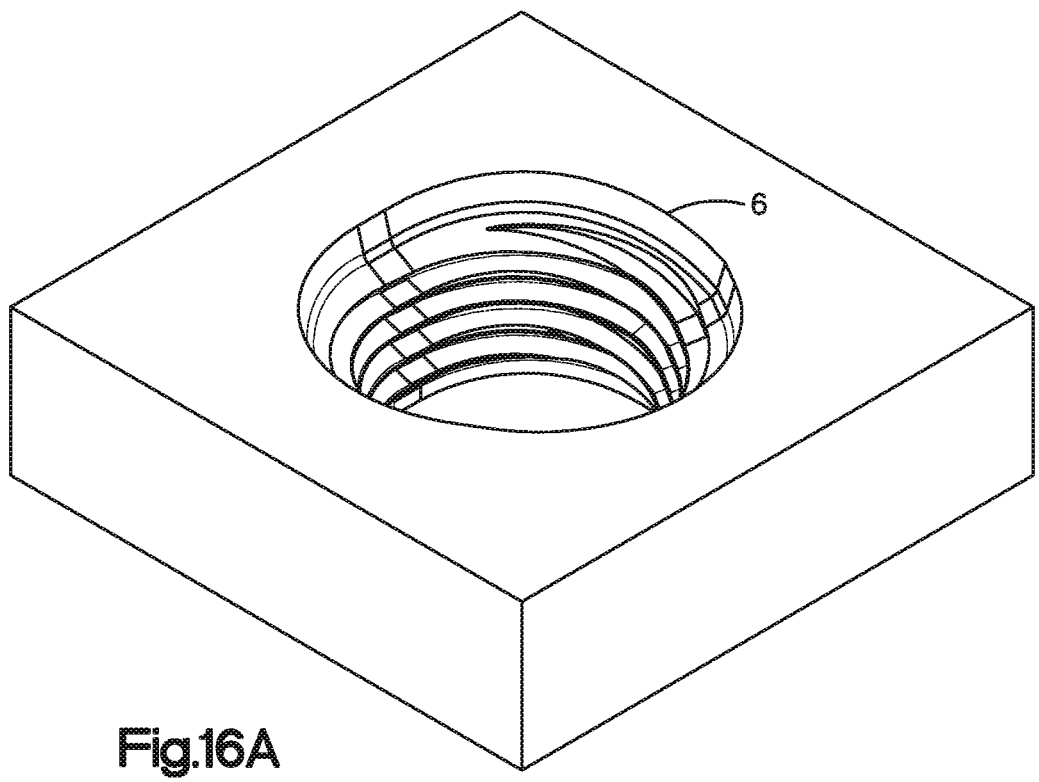
FIG. 16A is a perspective view of a bone plate having a trigon locking hole, according to another embodiment of the present disclosure.
Figure 16B:
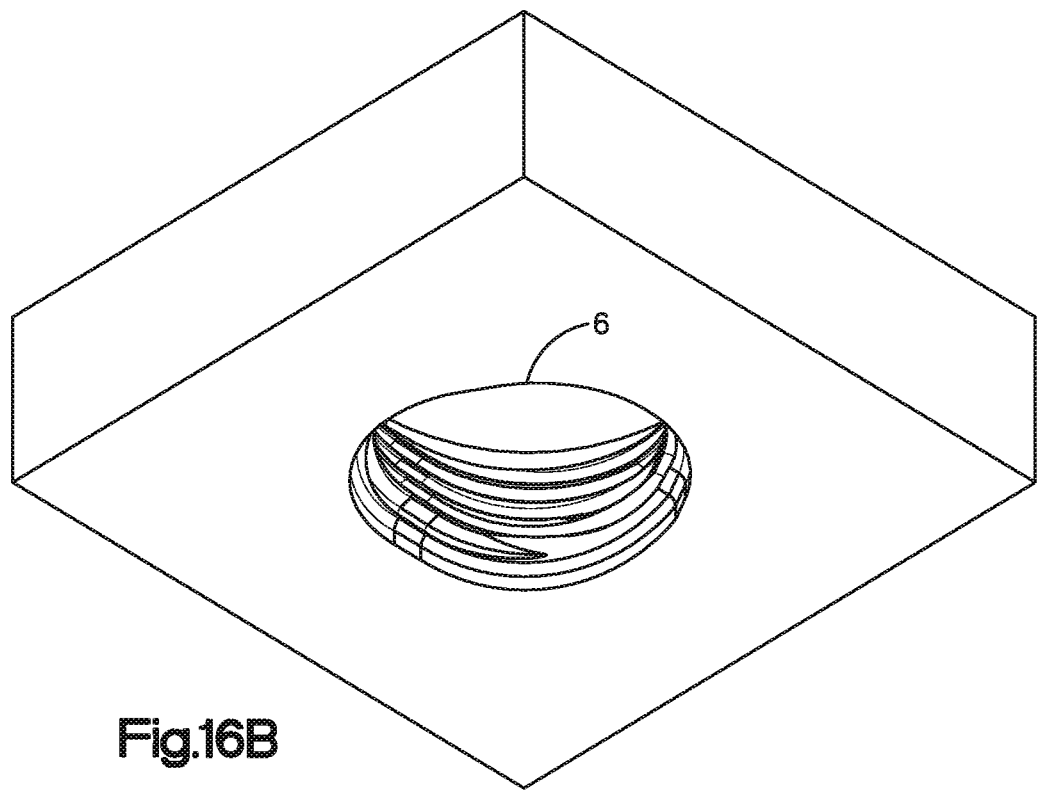
FIG. 16B is a perspective view of the bone plate having the trigon locking hole taken from the opposite perspective illustrated in FIG. 16A.
Figure 16D:
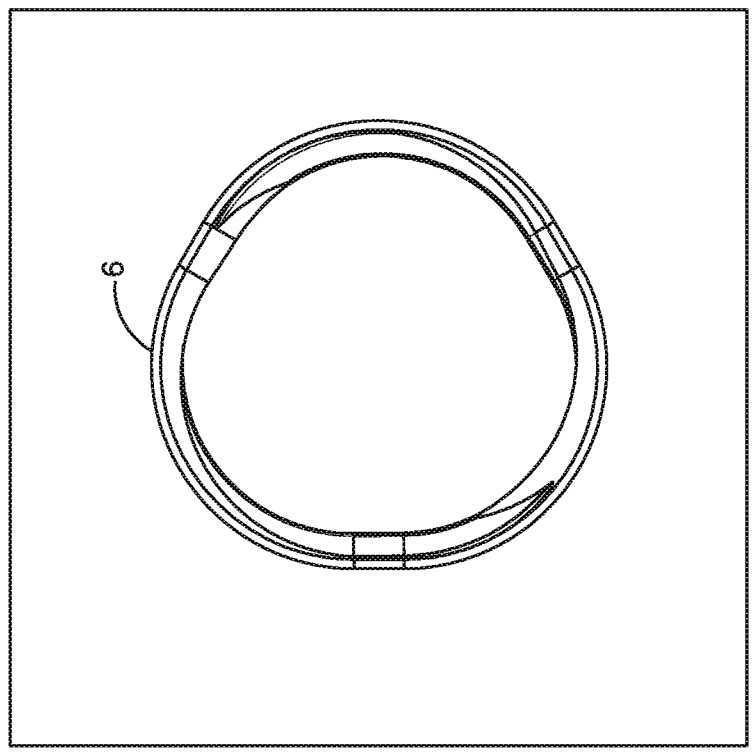
FIG. 16D is a bottom plan view of the trigon locking hole illustrated in FIG. 16A.
Figure 16C:
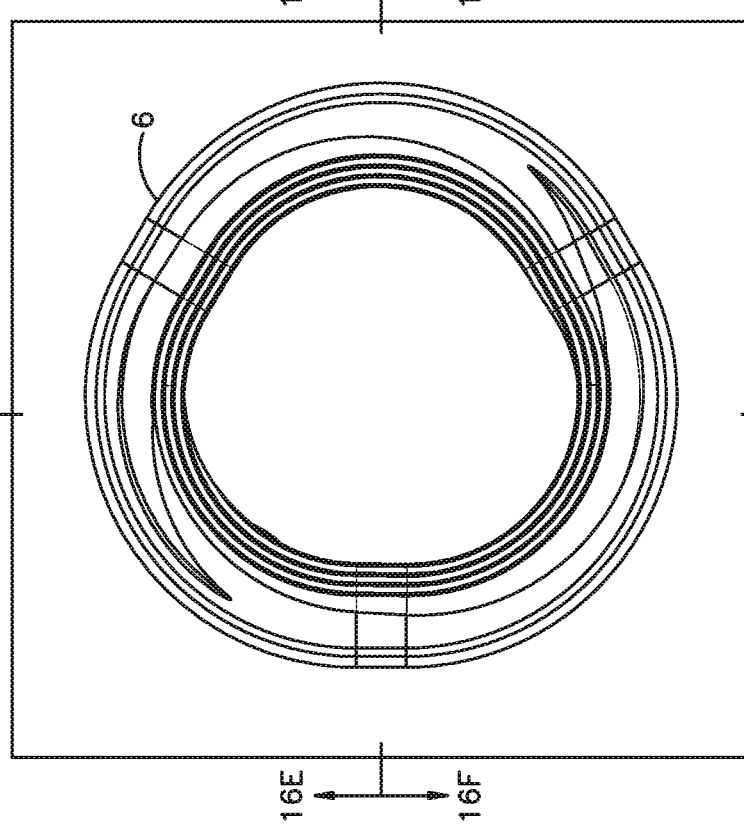
FIG. 16C is a top plan view of the trigon locking hole illustrated in FIG. 16A.
Figure 16E:
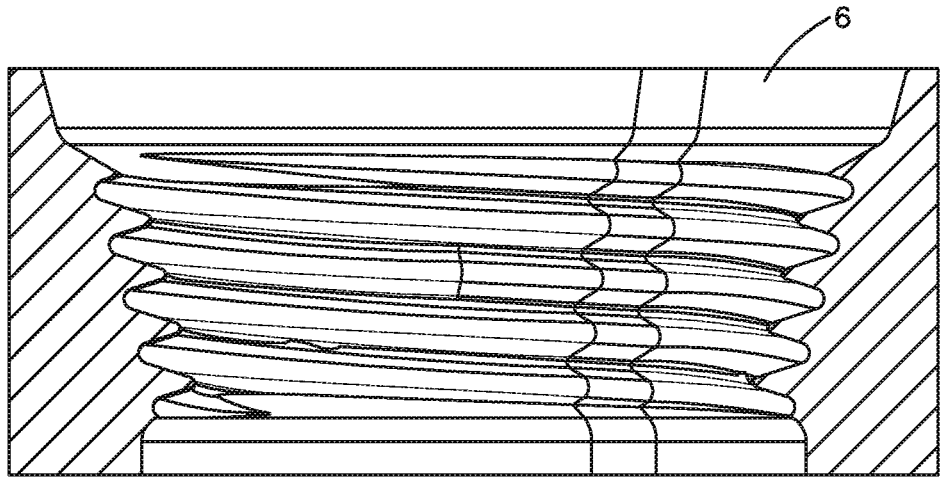
FIG. 16E is a sectional side view of the trigon locking hole taken along section line 16E-16E illustrated in FIG. 16C.
Figure 16F:
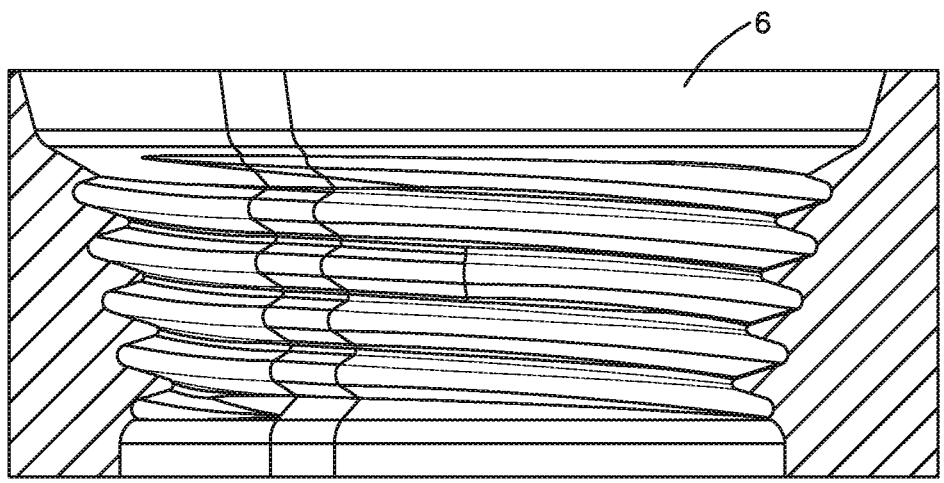
FIG. 16F is a sectional side view of the trigon locking hole taken along section line 16F-16F illustrated in FIG. 16C.
Figure 16G:
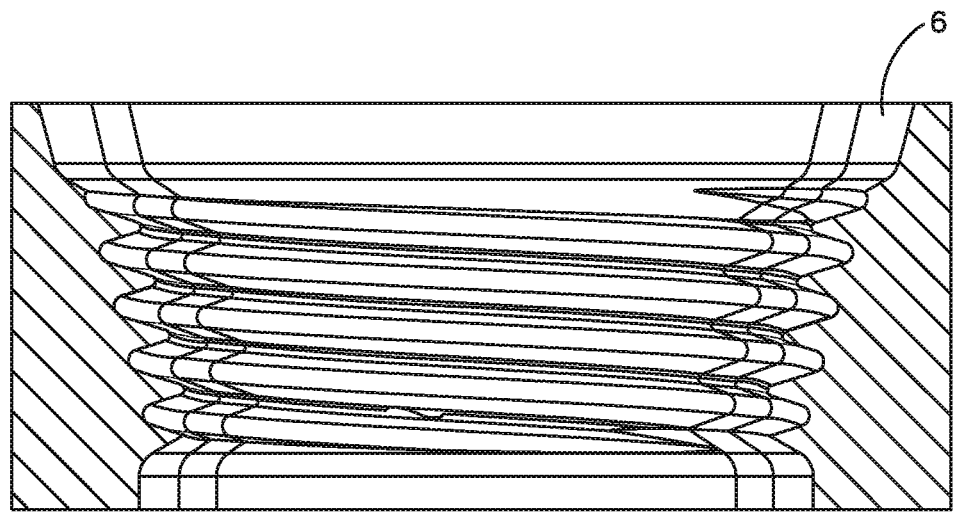
FIG. 16G is a sectional side view of the trigon locking hole taken along section line 16G-16G illustrated in FIG. 16C.
Figure 16H:
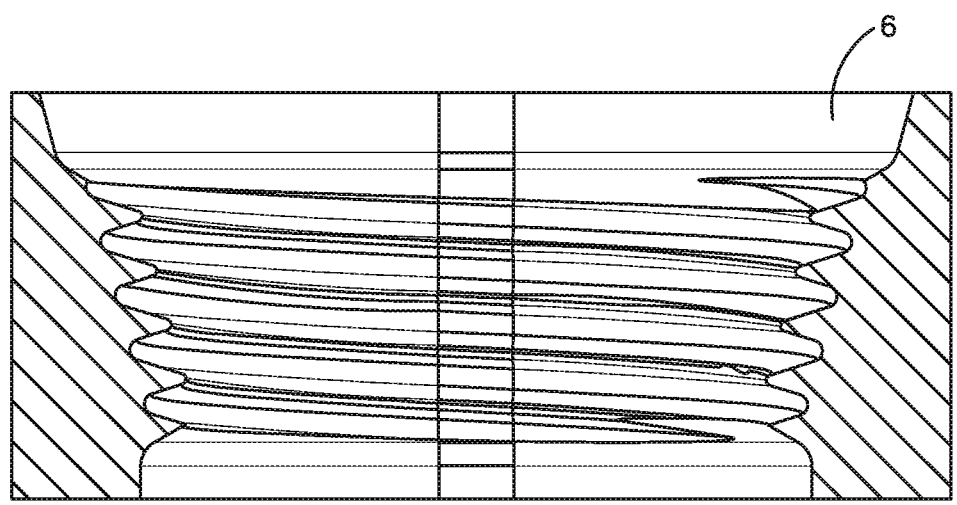
FIG. 16H is a sectional side view of the trigon locking hole taken along section line 16H-16H illustrated in FIG. 16C.

Referring now to FIG. 12A, in additional embodiments, the combi-hole 90 can be configured such that the trigon VA locking hole 6 and the compression hole 92 thereof retain their respective base geometries while the first axial separation distance LA1 is increased relative to that of the embodiment shown in FIG. 11G by an axial distance LA3. Stated differently, the VA locking hole 6 and compression hole 92 can be moved slightly away from each other in the combi-hole 90 of the present embodiment. In this manner, as shown in FIG. 12B, the interface edges 122 can effectively be limited to a few roots 58 and contiguous regions of the upper and lower flank portions 55b, 57b of the plate threads 9. As used herein with respect to a hole (e.g., the VA locking hole 6 and the compression hole 92), the terms "base geometry", "base version", and derivatives thereof refer to a stand-alone version of the hole 6, 92 that is not intersected by another hole. Thus, the "base geometry" or "base version" of the VA locking hole 6 refers to a stand-alone version of the VA locking hole 6 that is not intersected by a compression hole 92 or another type of hole; and the "base geometry" or "base version" of the compression hole 92 refers to a stand-alone version of the compression hole 92 that is not intersected by the VA locking hole 6 or another type of hole. For example, FIGS. 13B, 14B, and 15B show the respective base versions of the VA locking holes 6 of the combination holes 90 shown in FIGS. 13A, 14A, and 15A. Accordingly, the features and geometries of the base versions of the VA locking holes 6 shown in FIGS. 13B, 14B, and 15B (and reference numbers therein) are instructive regarding such features and geometries of the respective VA locking holes 6 of the combination holes 90 shown in FIGS. 13A, 14A, and 15A. Thus, the reader will appreciate that FIGS. 13A and 13B should be viewed together, as should FIGS. 14A and 14B, and also FIGS. 15A and 15B.

Figure 13A:
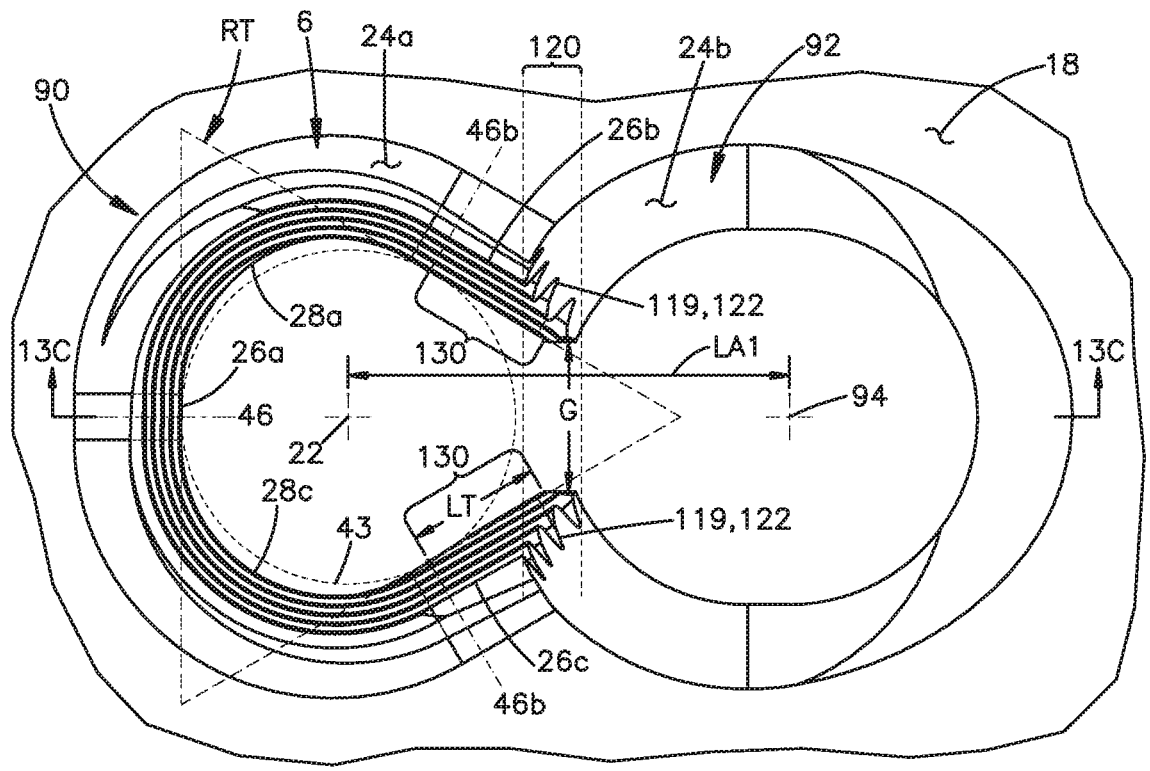
FIG. 13A is a top plan view of a combination hole having a linear elongated thread transition zone between the trigon locking hole and the compression hole, according to another embodiment of the present disclosure.
Figure 13B:
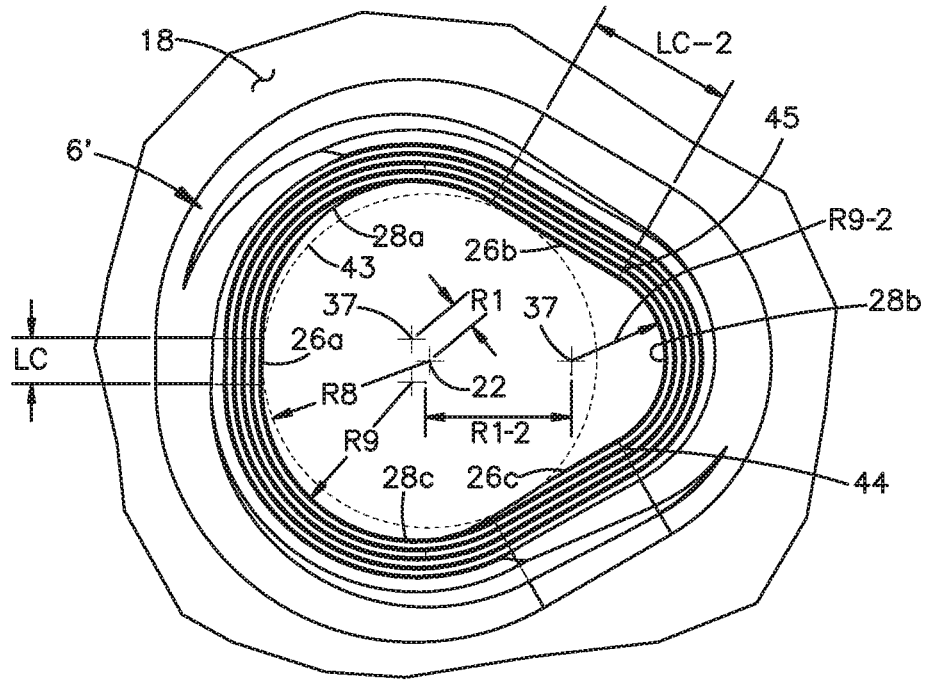
FIG. 13B is a top plan view of a base version of the locking hole employed in the combination hole illustrated in FIG. 13A.

Referring now to FIGS. 13A through 13E, in further embodiments, the locking surface 24a can define a thread transition zone 130 in which the horizontal hole profile (and the thread path about central axis 22) deviates from the equilateral configuration in a manner elongating the thread path as it approaches and departs from the hole intersection zone 120. In the depicted embodiment, such deviation occurs between respective column axes 46b of the second and third columns 26b, 26c, which column axes 46b are positioned and oriented where the column centerlines 46 of the second and third columns 26b, 26c would be if these columns 26b, 26c were equilateral with the base column 26a. As shown in FIG. 13A, the thread transition zone 130 can effectively move the hole intersection zone 120 entirely outside the radius R8 of the reference circle 43. Thus, it can be said that radius R8 is less than a minimum distance measured from the central axis 22 of the VA locking hole 6 to the intersection boundary 119 with respect to the longitudinal hole direction.

As shown in FIGS. 13A and 13B, the second and third columns 26b, 26c can be elongated linearly along the thread transition zone 130 so as to define columns lengths LC-2 that are greater than the column length LC of the base column 26a. The plate threads 9 on either side of the intersection axis 97 can define a transition length LT measured from the respective column axis 46b of the second and third columns 26b, 26c to the intersection boundary 119. As best shown in FIG. 13B, which depicts an uninterrupted or "base" version 6' of the trigon VA locking hole 6 employed in the combi-hole 90 of FIG. 13A, the distance R1-2 between the central axis 22 and the corner axis 37 of the second corner 28b is thus greater than the distance R1 between the central axis 22 and the corner axes 37 of the first and third corners 28a, 28c. To maintain a smooth thread path along the second corner 28b of the base trigon VA locking hole 6', the second corner 28b can extend tangentially from the second side 45 of the second column 26b to the first side 44 of the third column 26c. Accordingly, the second corner 28b of the base trigon VA locking hole 6' can define a corner radius R9-2 smaller than corner radii R9 of the first and third corners 28a, 28c. Additionally, to maintain the thread pitch P1 both outside and inside the thread transition zone 130, the helix angle of the plate threads 9 is less inside the thread transition zone 130 and is greater outside the thread transition zone 130. Stated differently, the helix angle diminishes or "flattens out" inside the thread transition zone 130.

The thread transition zone 130 provides the plate threads 9 with a smoother entry to and departure from the intersection boundary 119 along the thread path about the central axis 22. In this manner, the thread transition zone 130 provides a reduction in the sharpness of the interface edges 122 while also maintaining the thread profiles of the plate threads 9 to a greater extent in the hole intersection zone 120, such as with a narrower lateral gap distance G and/or with less profound relief surfaces 126 (or optionally no relief surfaces 126) therein. Thus, even when the screw 8 is inserted at high angulations A1 that cause the head 27 to enter the hole intersection zone 120, the thread transition zone 130 can provide increased locking thread interface between the plate threads 9 and screw head threads 29 in the hole intersection zone 120 (and thus also overall) while also avoiding, minimizing, or at least reducing contact between abrupt and/or sharp edges of the plate threads 9 and screw head threads 29.

In embodiments where the combi-hole 90 has a linear elongated transition zone 130, the corner radius R9-2 of the second corner 28b of the base trigon VA locking hole 6' can be in a range from about 0.10 mm to about 2.5 mm and more particularly in a range from about 0.15 mm to about 0.90 mm, and more particularly in a range from about 0.175 mm to about 0.825 mm. Moreover, the distance R1-2 between the central axis 22 and the corner axis 37 of the second corner 28b can be in a range from about 0.40 mm to about 6.00 mm, and more particularly in a range from about 0.75 mm to about 4.50 mm, and more particularly in a range from about 1.50 mm to about 3.75 mm. Additionally, the column length LC-2 of the second and third columns 26b,c can be in a range from about 0.20 mm to about 6.00 mm, and more particularly in a range from about 0.40 mm to about 3.40 mm, and more particularly in a range from about 0.50 mm to about 2.85 mm. It should be appreciated that dimensions R8, LA1, R9, R1, and LC can be within the respective ranges described above.

According to a first non-limiting example of the present embodiment, the radius R8 of the reference circle 43 can be about 2.050 mm, the first axial separation distance LA1 can be from about 4.0 mm to about 4.8 mm, the corner radii R9 of the first and third corners 28a, 28c can be about 1.95 mm, the corner radius R9-2 of the second corner 28b (i.e., the "second corner radius") can be about 1.10 mm, the distance R1 between the central axis 22 and the corner axis 37 of the first and third corners 28a, 28c can be about 0.142 mm, the distance R1-2 between the central axis 22 and the corner axis 37 of the second corner 28b can be about 1.824 mm, the base column 26a can have a column length LC from about 0.2 mm to about 0.35 mm, and particularly about 0.274 mm, and the second and third columns 26b, 26c can each have a column length LC-2 of about 1.763 mm.

According to a second non-limiting example of the present embodiment, dimensions R8, R9, LA1, LC, and R1 can be substantially the same as in the first example, while the second and third columns 26b, 26c can each have a column length LC-2 of about 2.802 mm, the second corner radius R9-2 can be about 0.200 mm, and distance R1-2 can be about 2.918 mm.

In some embodiments, such as those where the trigon VA locking hole 6 defines an equilateral reference triangle RT and the thread transition zone 130 employs linearly elongated second and third columns 26b, 26c, the second corner radius R9-2 can be in a range from about 0 mm (i.e., the first surfaces 42 of the second and third columns 26b, 26c can intersect substantially at a single point) to substantially equivalent to corner radius R9. Additionally or alternatively, a ratio between the column length LC of the base column 26a to the column lengths LC-2 of the second and third columns can be in a range of about 1:1.0 to about 1:100.0, and more particularly in a range of about 1:2.0 to about 1:15, and more particularly in a range of about 1:5 to about 1:8, and more particularly about 1:6.43, by way of non-limiting examples. In further embodiments employing linear elongated transition zones 130, a ratio of corner radius R9-2 to radius R8 can be in a range of about 0.0:1 to about 0.904:1, and more particularly in a range of about 0.400:1 to about 0.600:1, and more particularly about 0.54:1; a ratio of column length LC-2 to radius R8 can be in a range of about 0.0:1 to about 2.0:1, and more particularly in a range of about 0.75:1 to about 0.95:1, and more particularly about 0.86:1; and a ratio of axial separation distance LA1 to radius R8 can be in a range of about 0.1:1 to about 4.0:1, and more particularly in a range of about 1.0:1 to about 3.5:1, and more particularly about 2.34:1. It should be appreciated that in other embodiments the reference triangle RT need not be equilateral and need not be isosceles. For example, the columns 26a-c can be oriented such that the vertex angles AV1, AV2, AV3 of the references triangle RT are each different from one another. Moreover, in some embodiments, the columns 26a-c can each have difference column lengths.

Figure 13F:
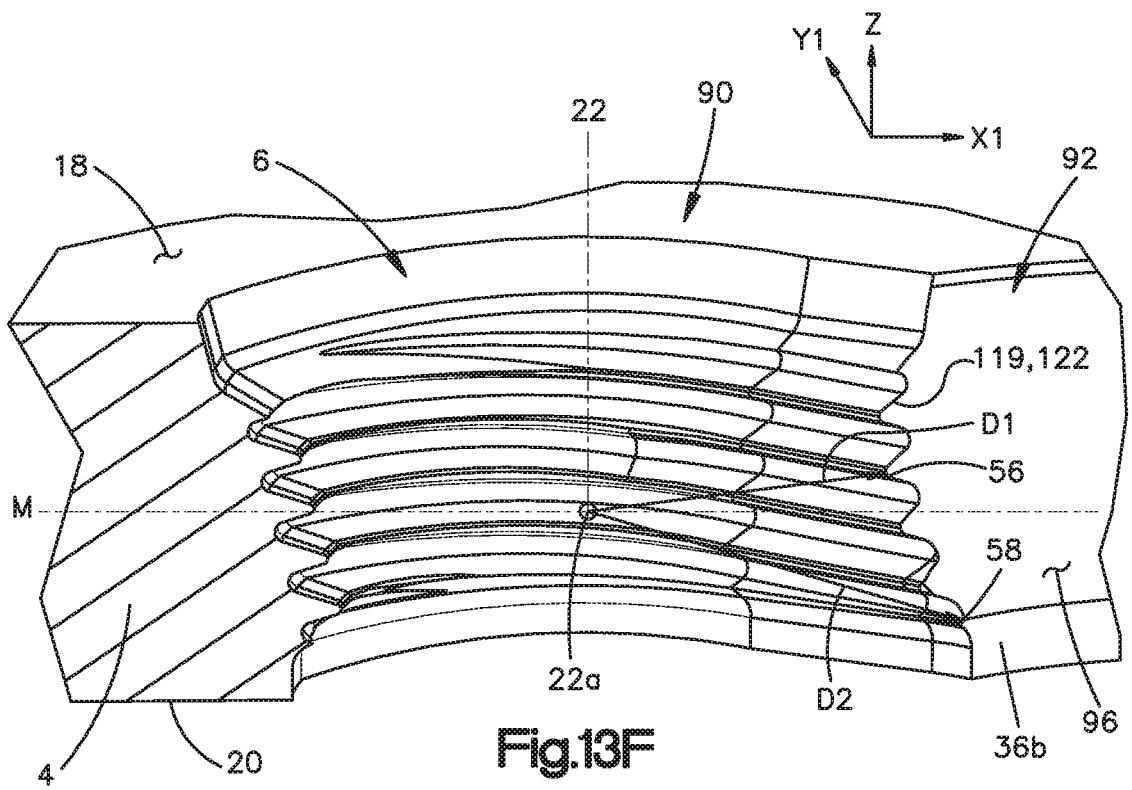
FIG. 13F is an enlarged sectional perspective view of the trigon locking hole taken along section line 13C-13C illustrated in FIG. 13A.

Referring now to FIG. 13F, the thread transition zone 130 beneficially increases the straight line distances between the axial midpoint 22a of the central axis 22 and the intersection boundary 119. For example, in the present embodiment, the minimum straight line distance D1 can be measured to a crest 56 that is not truncated by a relief surface 126. Moreover, the maximum straight line distance D2 can be measured to a location at which a root 58 of the plate threads 9 intersects a boundary between the compression surface 96 and the undercut surface 36b of the compression hole 92. Thus, the thread transition zone 130 effectively increases these minimum and maximum straight line distances D1, D2 while also decreasing the gap distance G relative to the embodiments above, thereby provided increased threaded engagement between the plate threads 9 and the screw head threads 29 at angulation of the screw head 27 toward the compression hole 92 and into intersection zone 120, as described below. The minimum straight line distances D1 can be in a range of about 0.5 mm to about 7.0 mm, and more particularly in a range from about 1.0 mm to about 4.5 mm, and more particularly about 2.0 mm to about 3.0 mm. The maximum straight line distances D2 can be in a range of about 0.5 mm to about 7.0 mm, and more particularly in a range from about 1.5 mm to about 5.0 mm, and more particularly about 2.5 mm to about 3.5 mm. A ratio of the minimum straight line distance D1 to radius R8 can be in a range of about 0.05:1 to about 3.0:1. A ratio of the maximum straight line distance D2 to radius R8 can be in a range of about 0.05:1 to about 3.0:1. The minimum gap distance G can be in a range of about 0.0 mm to about 7.0 mm, and more particularly in a range from about 0.80 mm to about 3.60 mm, and more particularly in a range from about 0.12 mm to about 2.40 mm. Although FIG. 13F depicts the intersection boundary 119 on only one lateral side of the combi-hole, it should be appreciated that the minimum and maximum straight line distances D1, D2 can be substantially similar at the intersection boundary 119 on the other lateral side of combi-hole 90.

Figure 13G:
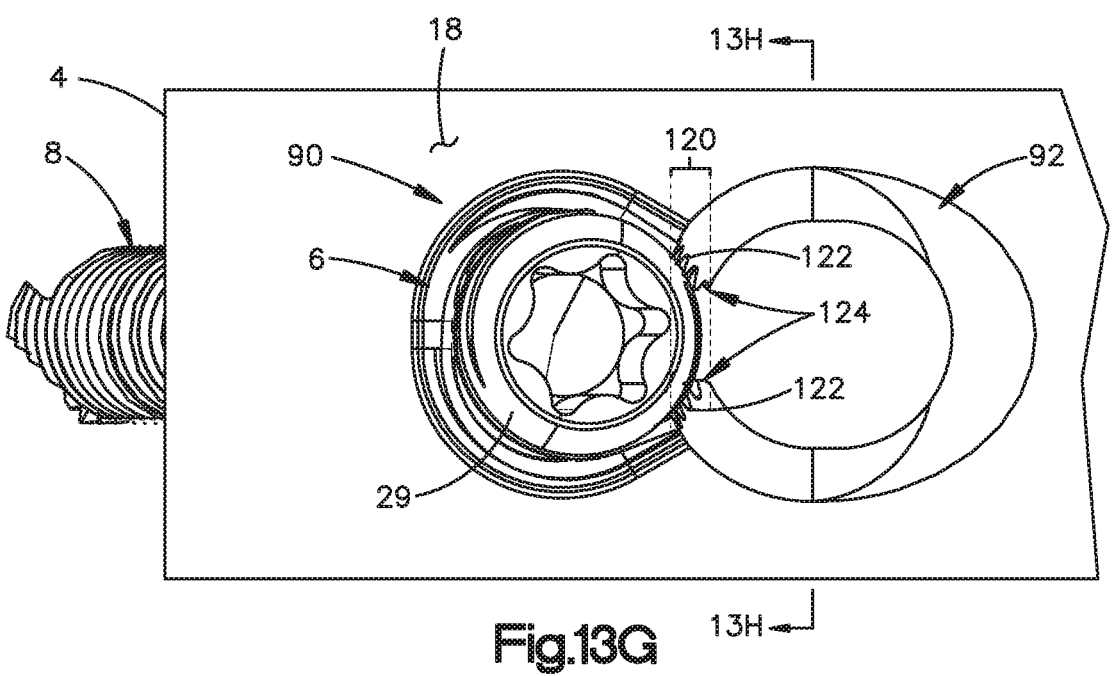
FIG. 13G is a top plan view of a bone fixation system that includes a bone screw fully seated in the trigon locking hole of the combination hole illustrated in FIG. 13A, in which the bone screw is angulated into a hole intersection zone between the trigon locking hole and the compression hole.
Figure 13H:
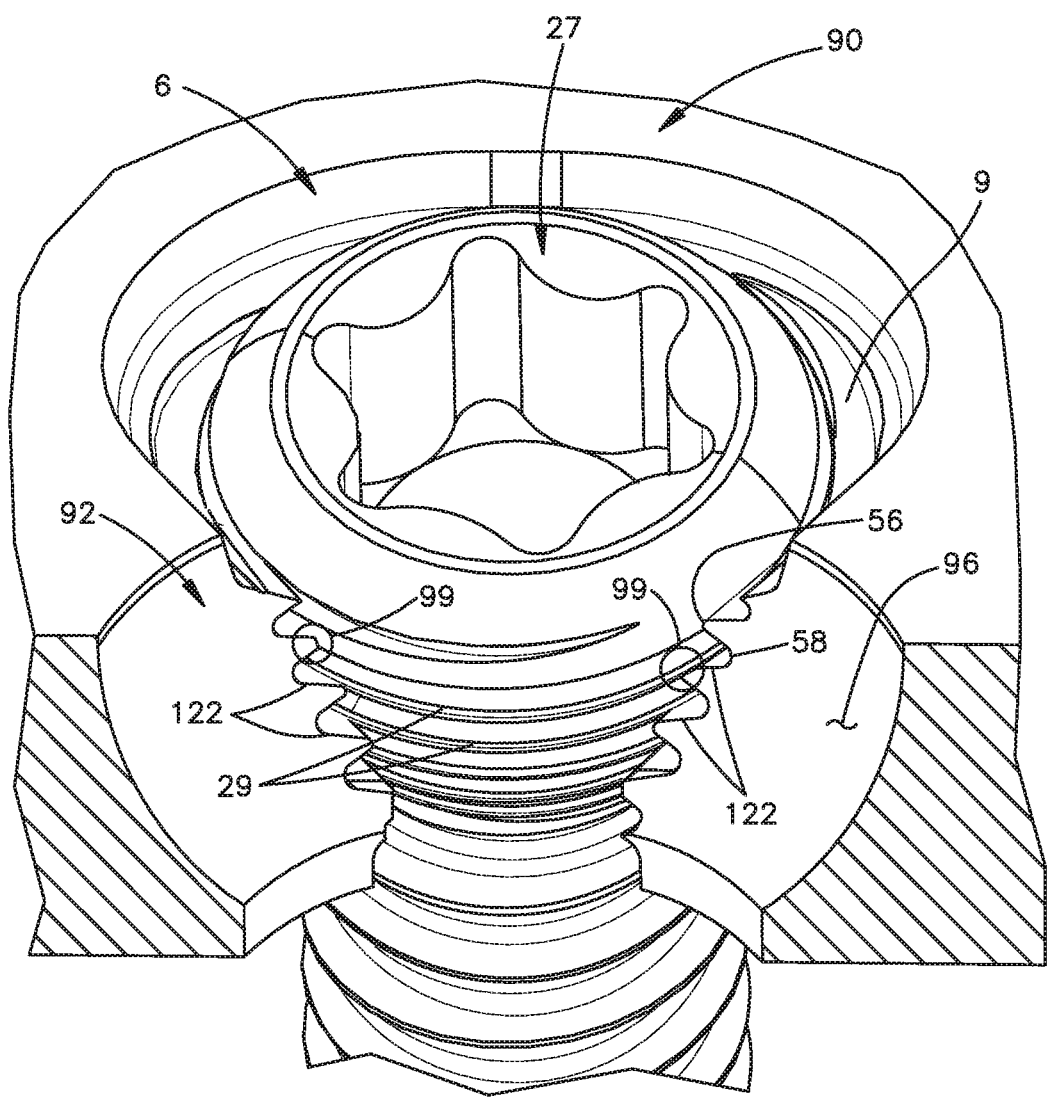
FIG. 13H is a sectional perspective view of the combination hole taken along section line 13H-13H illustrated in FIG. 13G, showing engagement between threads of a head of the angulated bone screw and threads of the trigon locking hole within the thread transition zone.

Referring now to FIGS. 13G and 13H, angulation of the screw head 27 into the hole intersection zone 120 is shown, particularly at an angulation A1 of about 15 degrees as indicated in FIG. 13C. As shown in FIG. 13H, even at such high angulation A1, contact between the screw head 27 (including the threads 29 thereof) and the interface edges 122 of the plate threads 9 can be significantly reduced, such as to a few interference regions 99. Similarly as described above, the thread proportions of the plate threads 9 and screw head threads 29 can be configured to cause the plate threads 9 and/or the screw head threads 29 to deform favorably at such interference regions 99. It should be appreciated that in further embodiments, the transition zone 130 can be configured so that contact between the screw head 27 and the interface edges 122 can be entirely avoided, even at high angulations.

Referring now to FIGS. 14A through 14E, in further embodiments, the locking surface 24a can define a thread transition zone 130 in which transition portions 132 of the locking surface 24a extend arcuately and convexly from the second and third columns 26b, 26c to the intersection boundary 119. In particular, as shown in FIG. 14A, the second and third columns 26b, 26c can be linear and can be shortened such that the column axes 46b thereof are located at the respective side 44, 45 thereof nearest the intersection boundary 119.

The second and third columns 26b, 26c can define linear column lengths LC-2 that are one-half the column length LC of the base column 26a. Additionally, the transition portions 132 can extend along respective transition lengths LT, which in the present embodiment are arc lengths RC-3 (see FIG. 14B), that are longer than the column lengths LC-2 of the second and third columns 26b, 26c. However, in other embodiments, such as shown in FIGS. 15A and 15B, the column lengths LC-2 of the second and third columns 26b, 26c can be greater than the column length LC of the base column 26a, and the arc lengths RC-3 of the transition portions 132 (FIG. 15B) can be shorter than the column lengths LC-2 of the second and third columns 26b, 26c. As above, the plate threads 9 on either side of the intersection axis 97 can define a transition length LT measured from the respective column axis 46b of the second and third columns 26b, 26c to the intersection boundary 119.

As best shown in FIGS. 14B and 15B, which depicts the base versions 6' of the trigon VA locking holes 6 shown in FIGS. 14A and 15A, the transition portions 132 define a radius of curvature R11 (also referred to herein individually as "transition radius" R11 and collectively as "transition radii" R11), which can be constant along the second portions 26-2. As in the embodiment described above, distance R1-2 can be greater than distance R1. The second corner 28b can extend tangentially from the transition portion 132 adjacent the second column 26b to the transition portion 132 adjacent the third column 26c. The second corner 28b can define a corner radius R9-2 smaller than corner radii R9 of the first and third corners 28a, 28c. Additionally, as above, the helix angle of the plate threads 9 is reduced in the thread transition zone 130 to maintain a constant thread pitch P1 both outside and inside the thread transition zone 130.

It should be appreciated that, in embodiments where the combi-hole 90 has an arcuate, convex transition zone 130, the transition radii R11 can range from substantially infinite (i.e., nearly linear) to substantially 0.0 mm (i.e., a short round-off adjacent the second and third columns 26b, 26c). More particularly, the transition radii R11 can be in a range about 0.10 mm to about 20.0 mm, and more particularly in a range from about 0.50 mm to about 6.00 mm, and more particularly in a range of about 1.75 mm to about 4.25 mm. It should be appreciated that dimensions R8, LA1, R9, R1, R1-2, LC, and LC-2 can be within the respective ranges described above.

According to a first non-limiting example of the embodiments shown in FIGS. 14A through 15B, the radius R8 of the reference circle can be about 2.050 mm, the first axial separation distance LA1 can be from about 4.0 mm to about 4.8 mm, the corner radii R9 of the first and third corners 28a, 28c can be about 1.95 mm, distance R1 can be about 0.142 mm, distance R1-2 can be about 2.800 mm, the base column 26a can have a column length LC from about 0.20 mm to about 0.35 mm, and more particularly about 0.274 mm, the second and third columns 26b, 26c can each have a column length LC-2 of about 0.550 mm, and the transition portions 132 can have a radius R11 of about 4.943 mm.

According to a second non-limiting example of the embodiments shown in FIGS. 14A through 15B, dimensions R8, R9, LA1, LC, and R1 can be substantially the same as in the immediately preceding example, while the second and third columns 26b, 26c can each have a column length LC-2 of about 1.410 mm, the radius R11 of the transition portions 132 can be about 2.741 mm, and distance R1-2 can be about 3.534 mm.

As described above, the transition radii R11 can range from substantially infinite (i.e., nearly linear) to substantially 0.0 mm (i.e., a short round-off adjacent the column 26b, 26c). Thus, it should be appreciated that a ratio of radius R8 to the transition radii R11 can be in a range of about 0.0:1 to about 1:0.0. More particularly, the ratio of R8 to R11 can be in a range of about 1:1.0 to about 1:3.5, and more particularly in a range from about 1:2.1 to about 1:2.7. Additionally or alternatively, a ratio between the column length LC of the base column 26a to the column lengths LC-2 of the second and third columns can be in a range of about 1:0.1 to about 1:100, and more particularly in a range of about 1:1.0 to about 1:20.0, and more particularly in a range of about 1:2 to about 1:15, and more particularly in a range of about 1:5 to about 1:8, by way of non-limiting examples. In further embodiments employing arcuate and convex transition portions 132, a ratio of axial separation distance LA1 to radius R8 can be in a range of about 0.1:1 to about 4.0:1, and more particularly in a range from about 0.125:1 to about 3.750:1, and more particularly in a range of about 0.155:1 to about 3.414:1. Moreover, a ratio of column length LC-2 to radius R8 can be in a range of about 0.1:1 to about 2.0:1, and more particularly in a range from about 0.125:1 to about 1.750:1, and more particularly in a range of about 0.134:1 to about 1.536:1.

It should be appreciated that the combi-hole 90 can employ a trigon VA locking hole 6 in which the transition zone 130 also transitions axially with respect the central hole axis 22 between the upper and lower surfaces 18, 20 of the plate 4, such that the hole 6 has multiple transition zone 130 profiles along the central hole axis 22. For example, the locking surface 24a can optionally include at least a first axial portion adjacent the upper plate surface 18 and defining a first transition zone 130 profile, such as any of those shown in FIGS. 13A through 15B, and at least a second axial portion extending axially between the first axial portion and the lower plate surface 20 and defining a second transition zone 130 profile that is different than the first horizontal hole profile.

Additional details of the combi-hole, as well as operation of a compression screw in the combination hole portion thereof, can be as more fully described in the '761 and '047 References.

Figure 18:
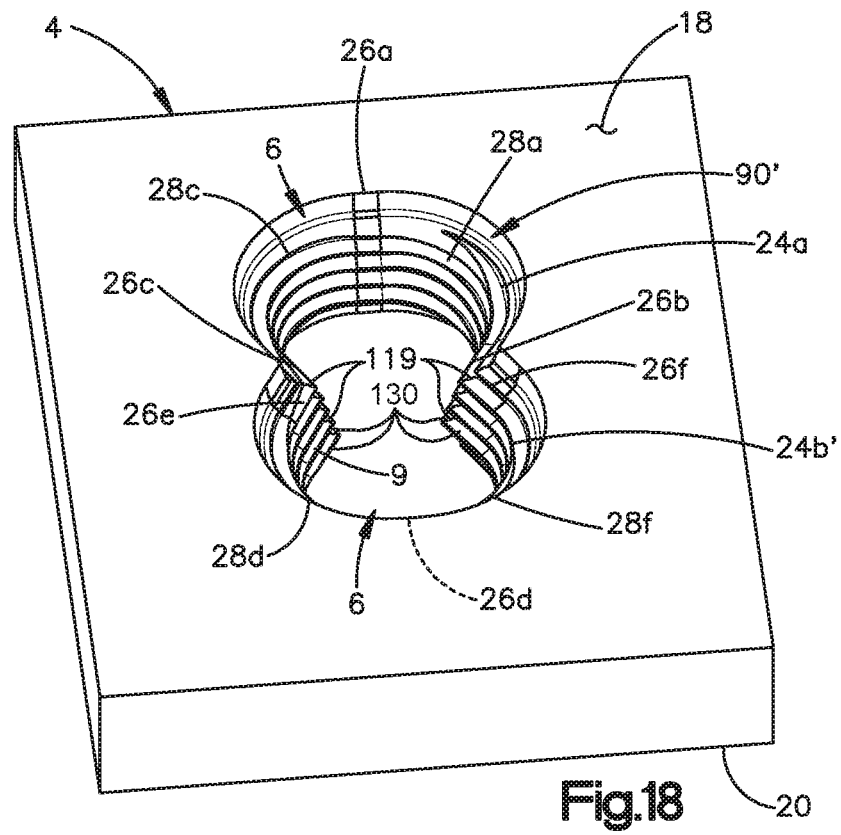
FIG. 18 is a perspective view of a bone plate having a combination hole that includes a trigon locking hole intersected by another trigon locking hole, in which both trigon locking holes are shaped similarly to the trigon locking hole illustrated in FIG. 13A, according to another embodiment of the present disclosure.
Figure 19:
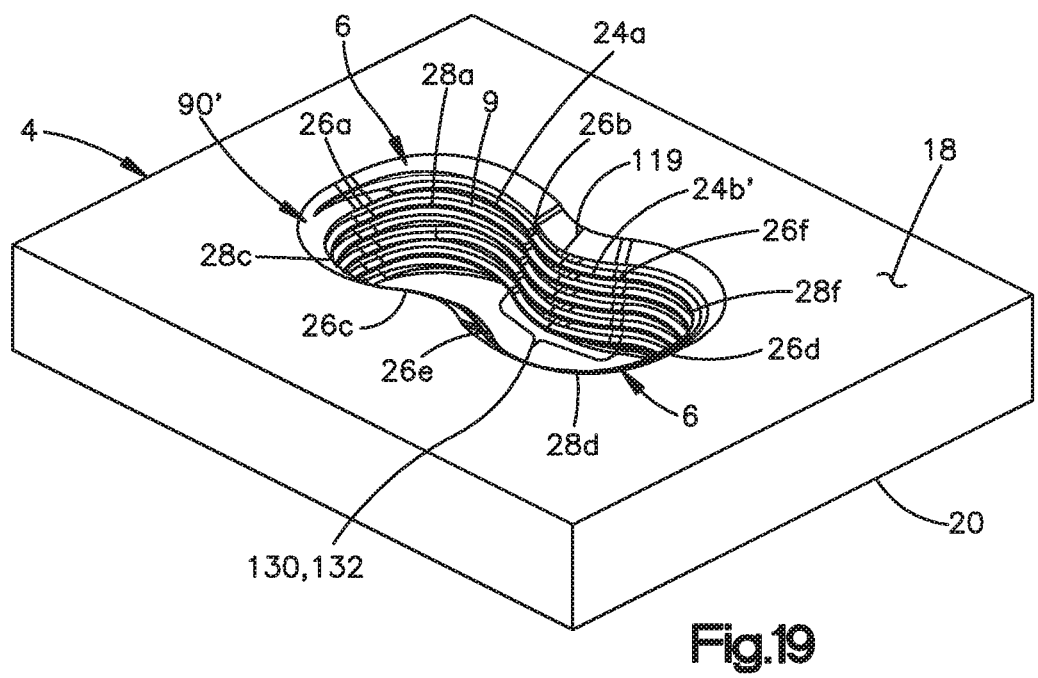
FIG. 19 is a perspective view of a bone plate having a combination hole that includes a trigon locking hole intersected by another trigon locking hole, in which both trigon locking holes are shaped similarly to the trigon locking hole illustrated in FIG. 14A, according to another embodiment of the present disclosure.
Figure 20:
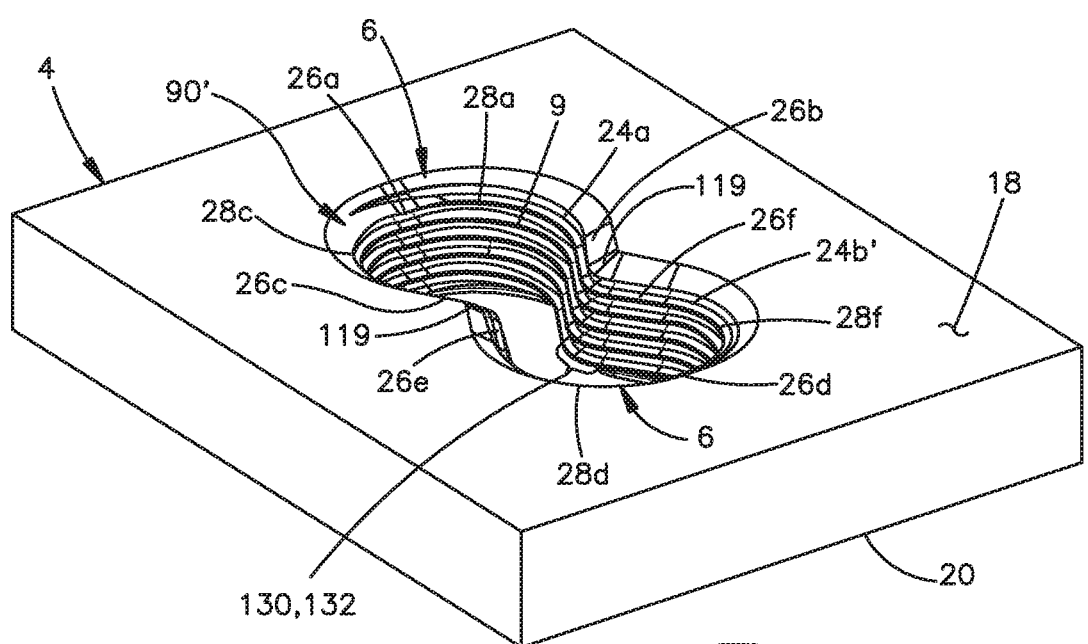
FIG. 20 is a perspective view of a bone plate having a combination hole that includes a trigon locking hole intersected by another trigon locking hole, in which both trigon locking holes are shaped similarly to the trigon locking hole illustrated in FIG. 15A, according to another embodiment of the present disclosure.
Figure 21A:
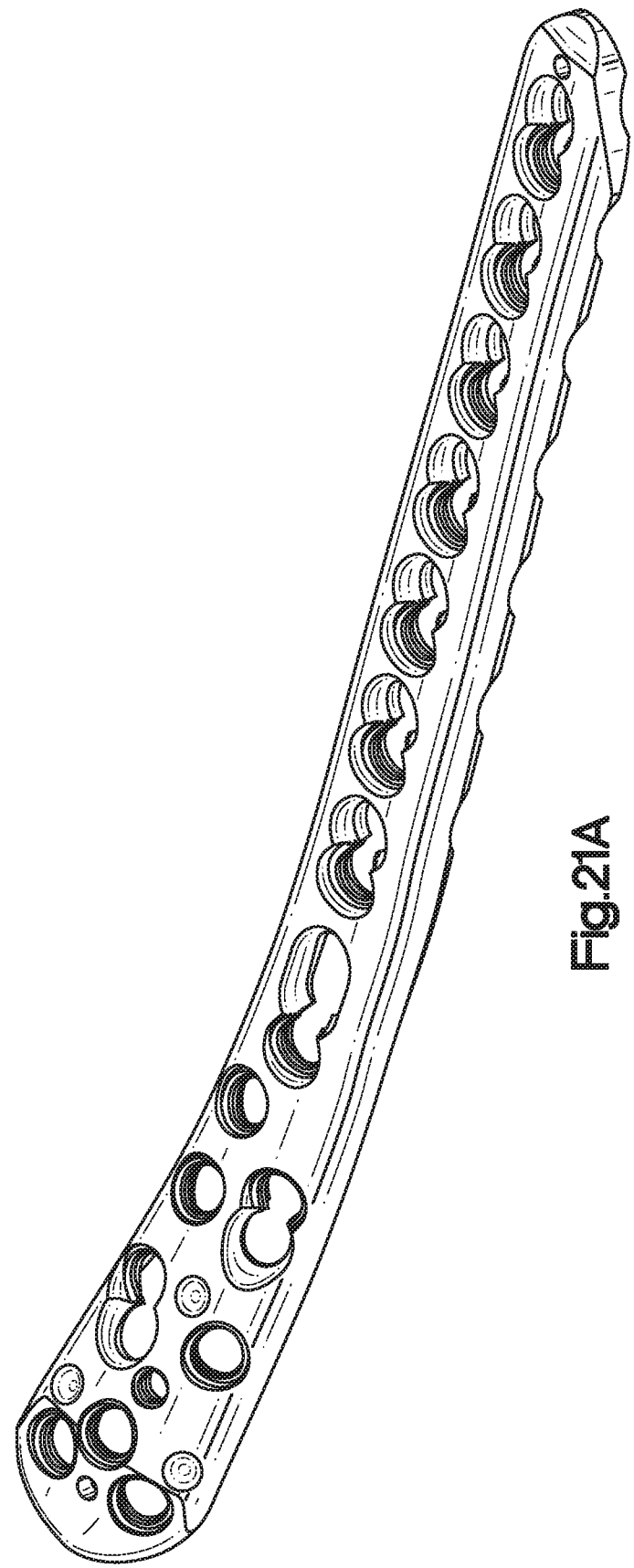
FIGS. 21A through 21G show respective views of a first additional bone plate, according to another embodiment of the present disclosure, the bone plate having various combination holes that include a trigon locking hole intersected by a compression hole, these views being a perspective view (FIG. 21A), top view (FIG. 21B), right side view (FIG. 21C), bottom view (FIG. 21D), left side view (FIG. 21E), front view (FIG. 21F), and rear view (FIG. 21G) of the bone plate.
Figure 21B:
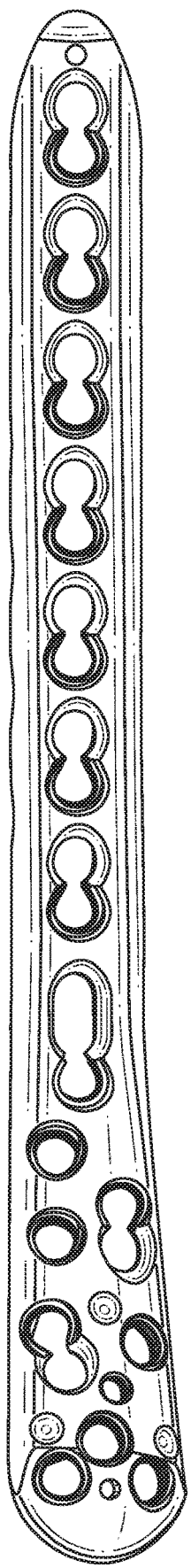
Figure 21C:
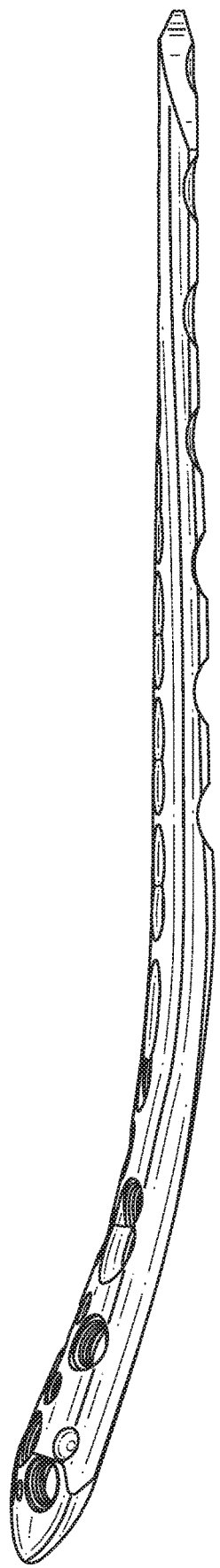
Figure 21D:
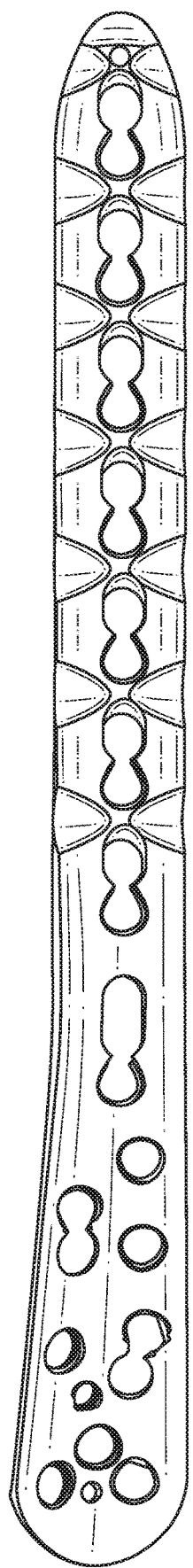
Figure 21E:
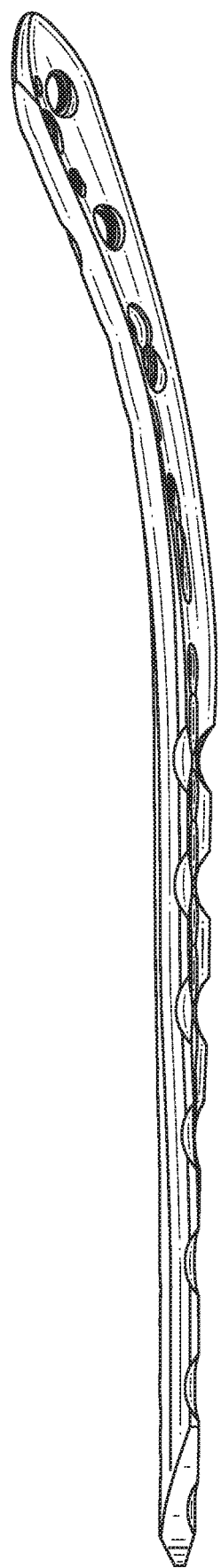
Figure 21F:
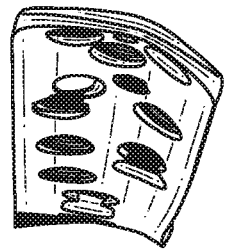
Figure 21G:
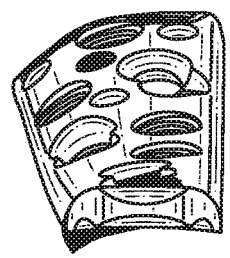
Figure 22A:
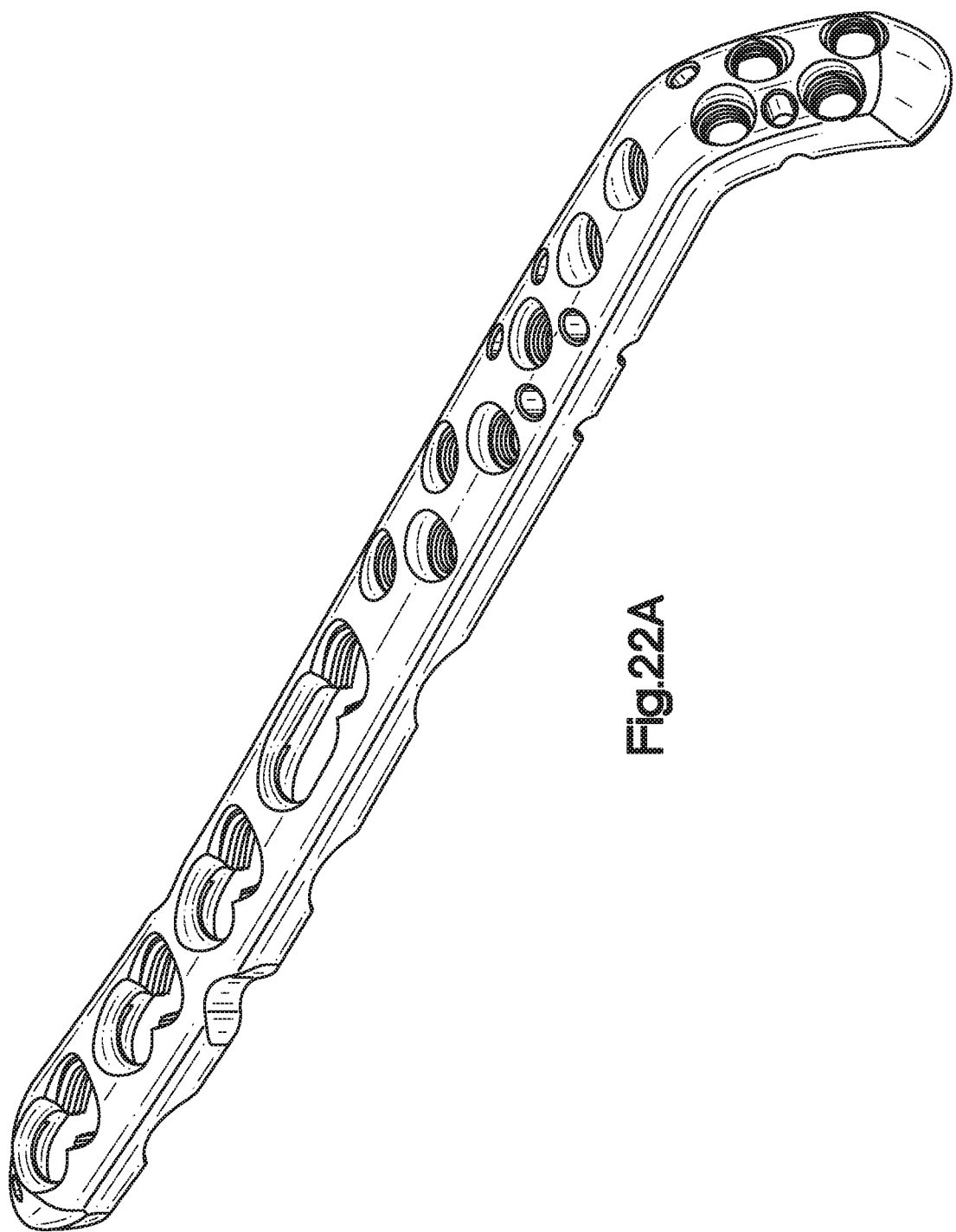
FIGS. 22A through 22G show respective views of a second additional bone plate, according to another embodiment of the present disclosure, the bone plate having various combination holes that include a trigon locking hole intersected by a compression hole, these views being a perspective view (FIG. 22A), top view (FIG. 22B), right side view (FIG. 22C), bottom view (FIG. 22D), left side view (FIG. 22E), front view (FIG. 22F), and rear view (FIG. 22G) of the bone plate.
Figure 22B:
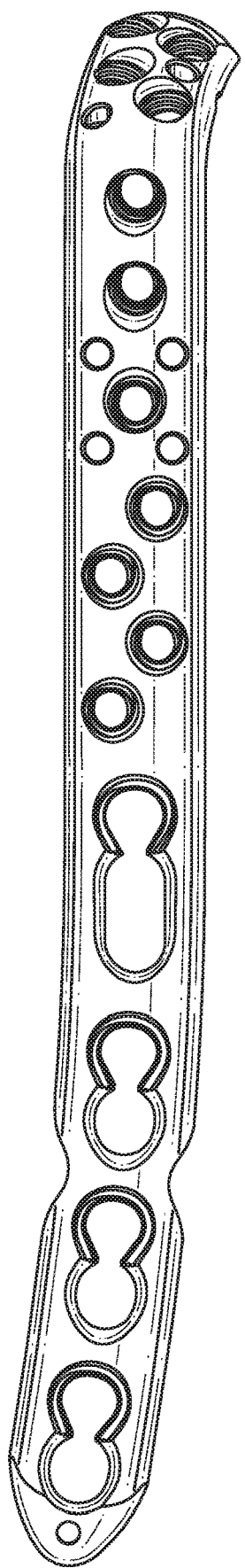
Figure 22C:
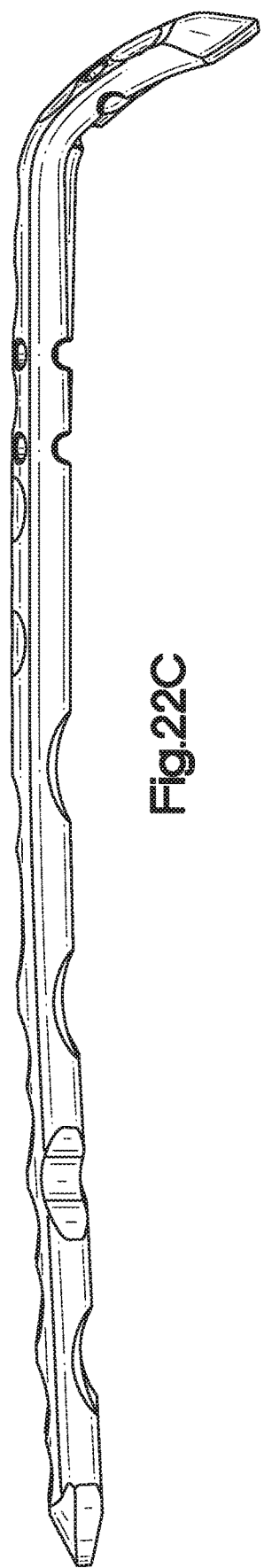
Figure 22D:
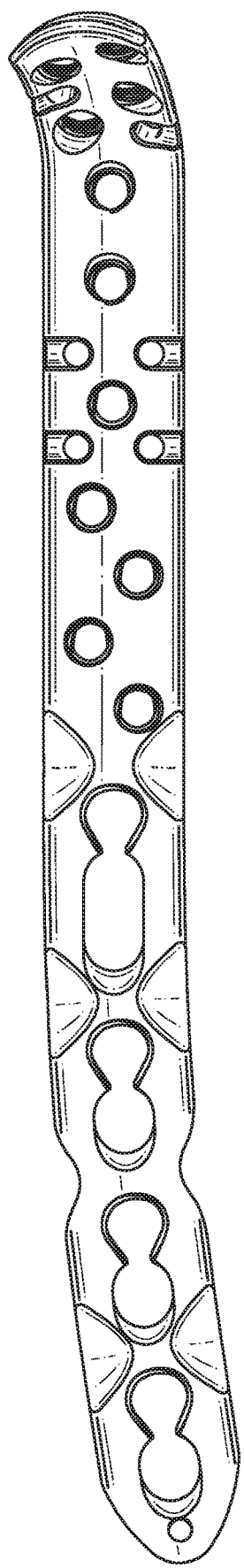
Figure 22E:
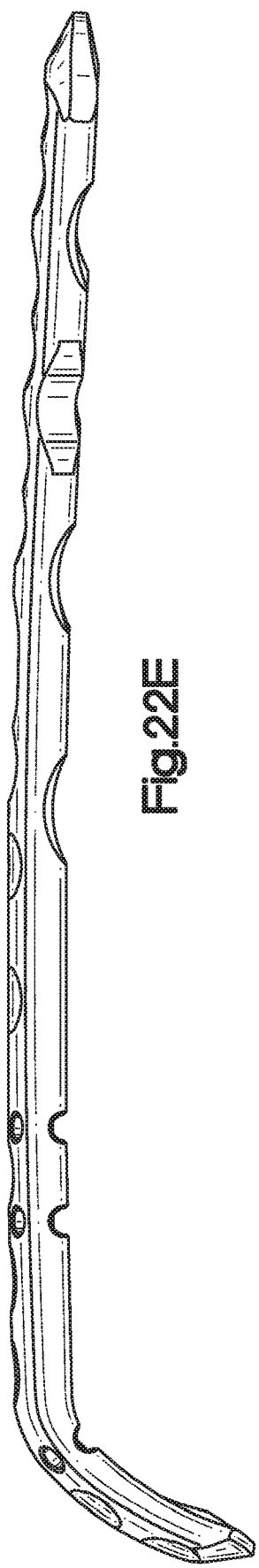
Figure 22F:
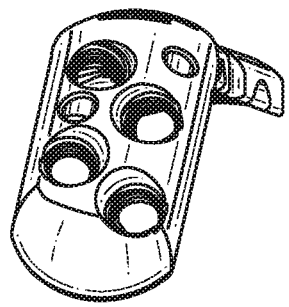
Figure 22G:
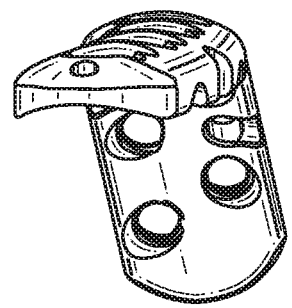
Figure 23A:
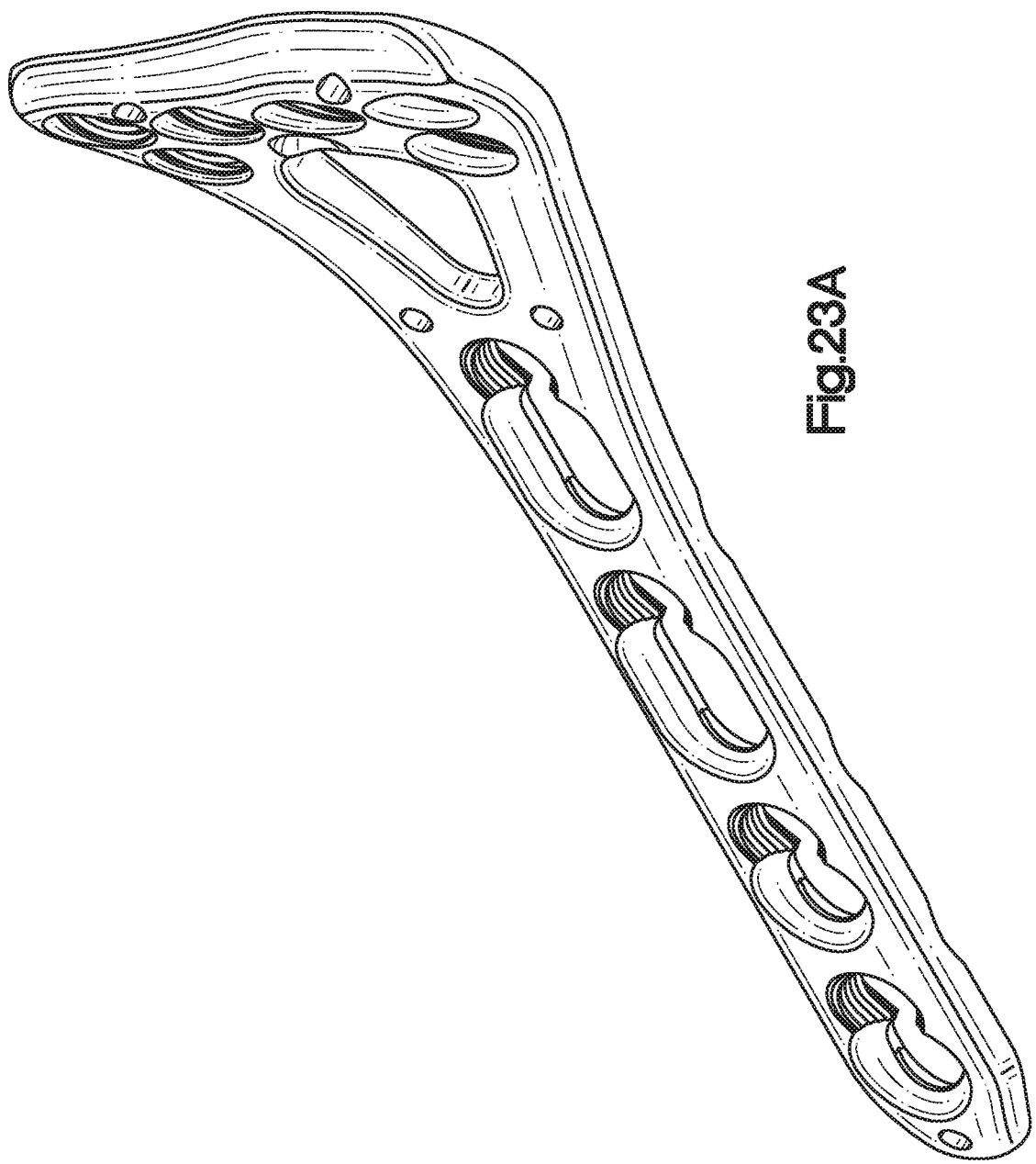
Figure 23B:
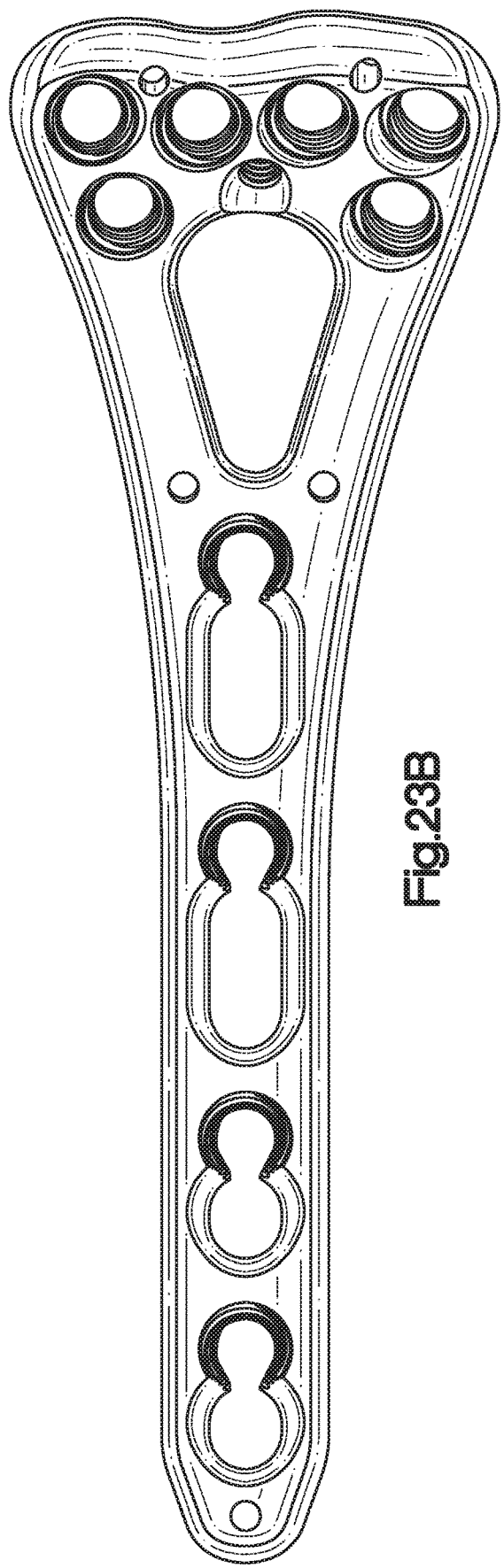
Figure 23C:
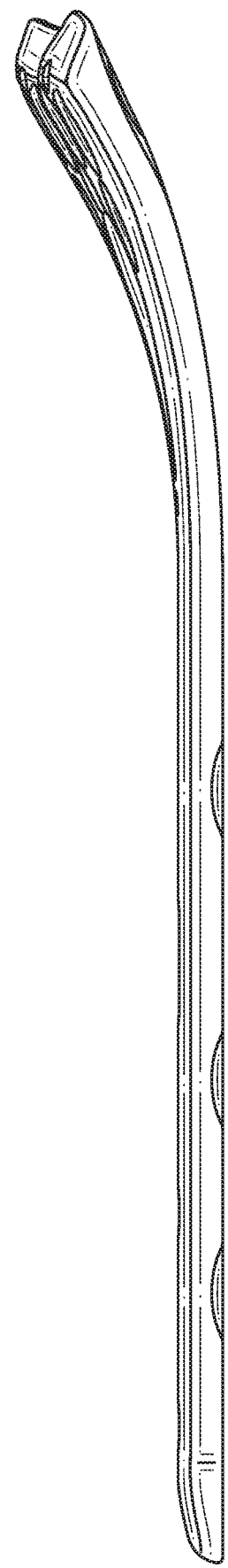
Figure 23F:
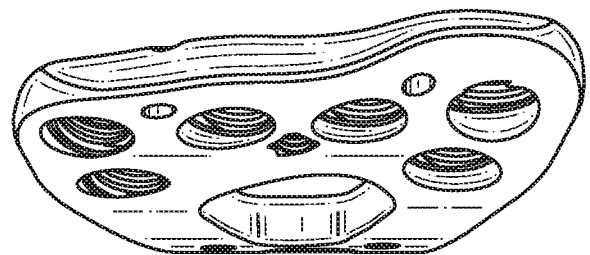
Figure 23G:
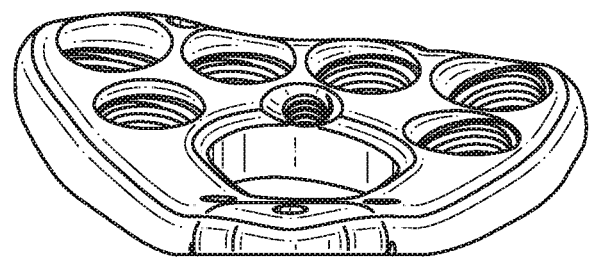
Figure 24B:
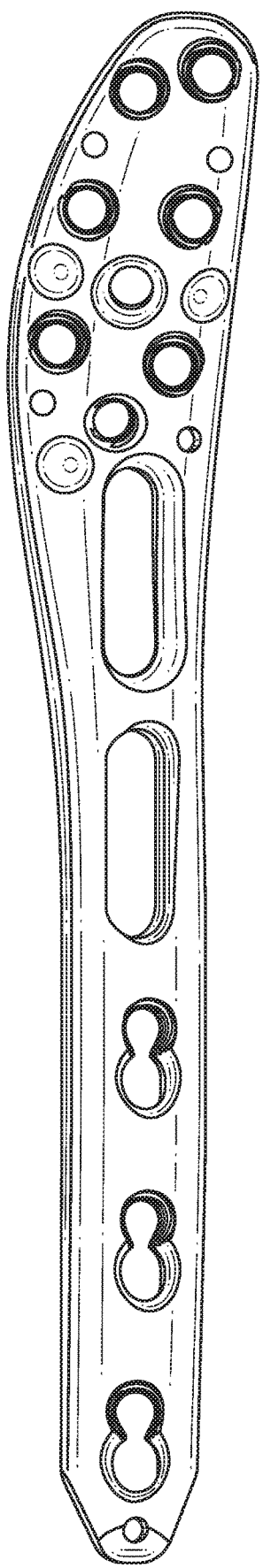
Figure 24C:
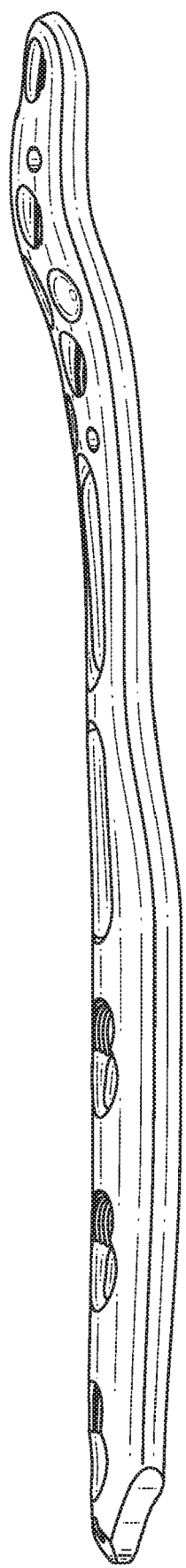
Figure 24D:
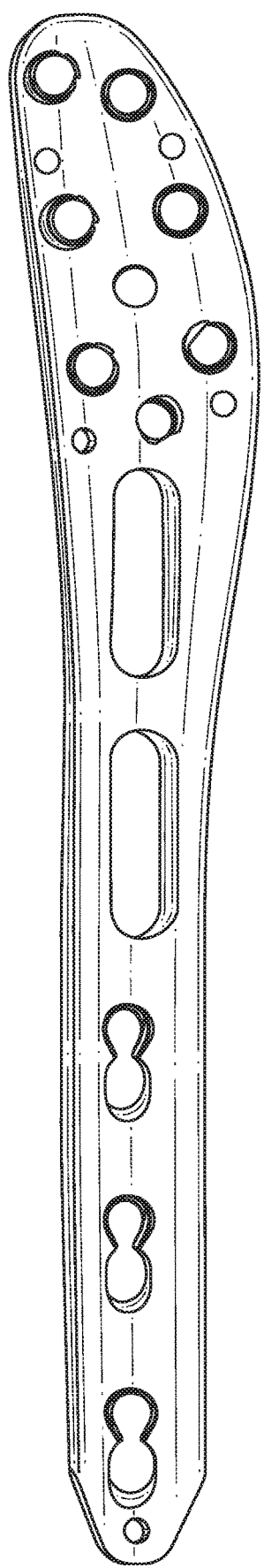
Figure 24E:
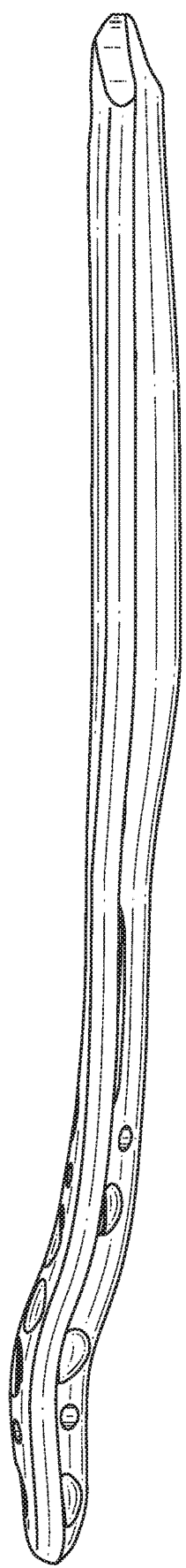
Figure 24F:
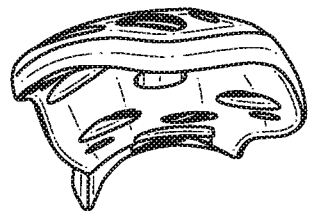
Figure 24G:
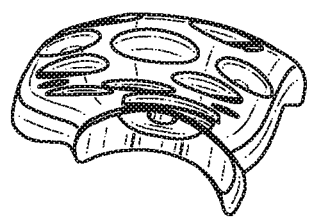
Figure 25A:
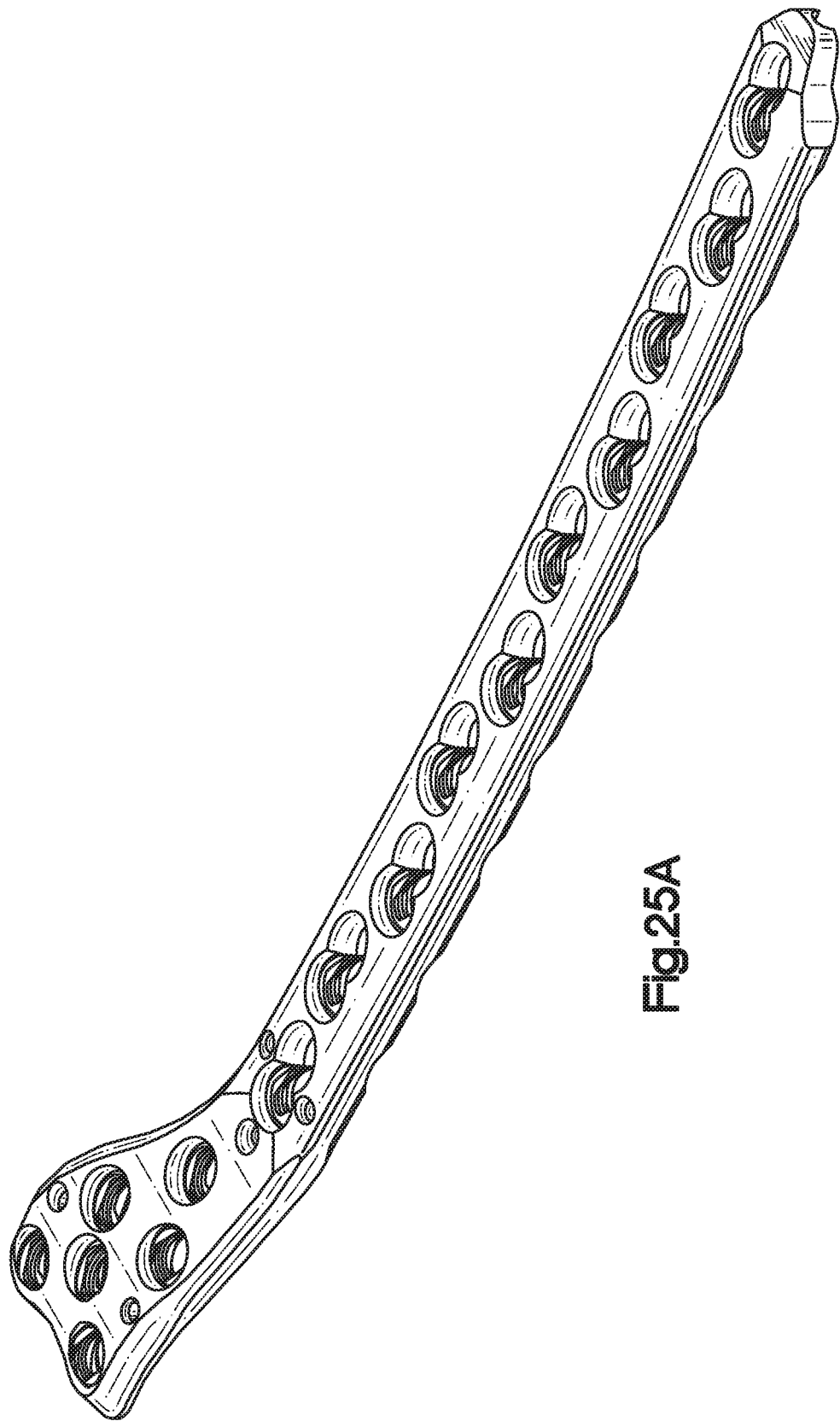
FIGS. 25A through 25G show respective views of a fifth additional bone plate, according to another embodiment of the present disclosure, the bone plate having various combination holes that include a trigon locking hole intersected by a compression hole, these views being a perspective view (FIG. 25A), top view (FIG. 25B), right side view (FIG. 25C), bottom view (FIG. 25D), left side view (FIG. 25E), front view (FIG. 25F), and rear view (FIG. 25G) of the bone plate.
Figure 25B:
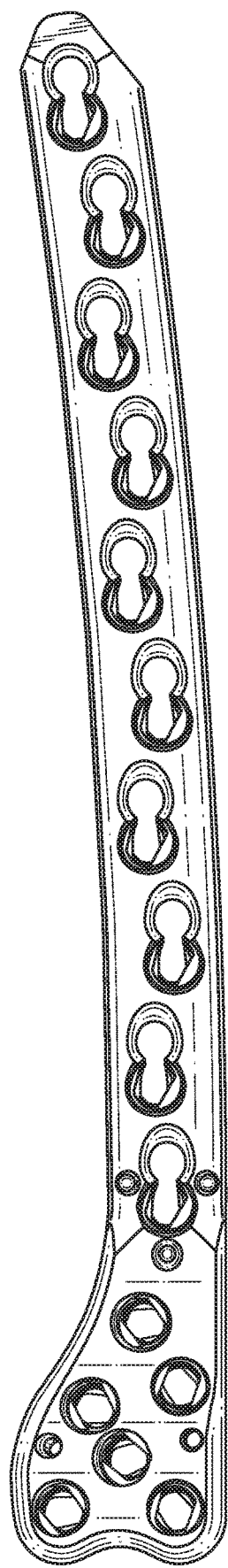
Figure 25C:
Figure 25D:
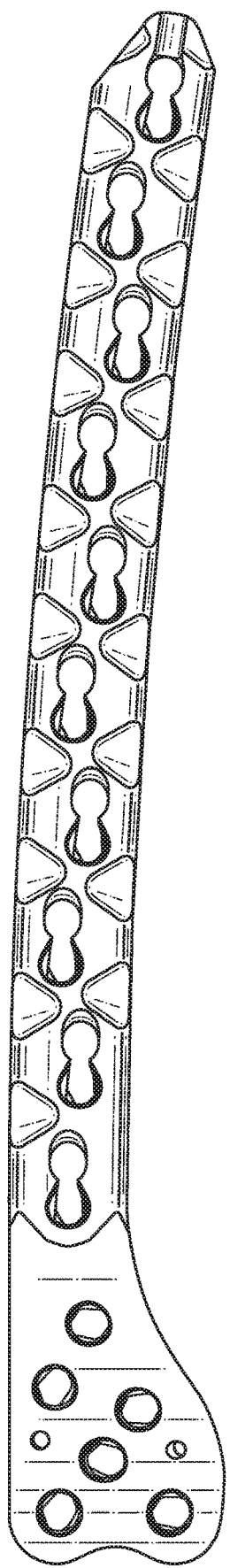
Figure 25E:
Figure 25F:
Figure 25G:
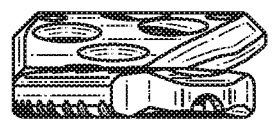
Figure 26A:
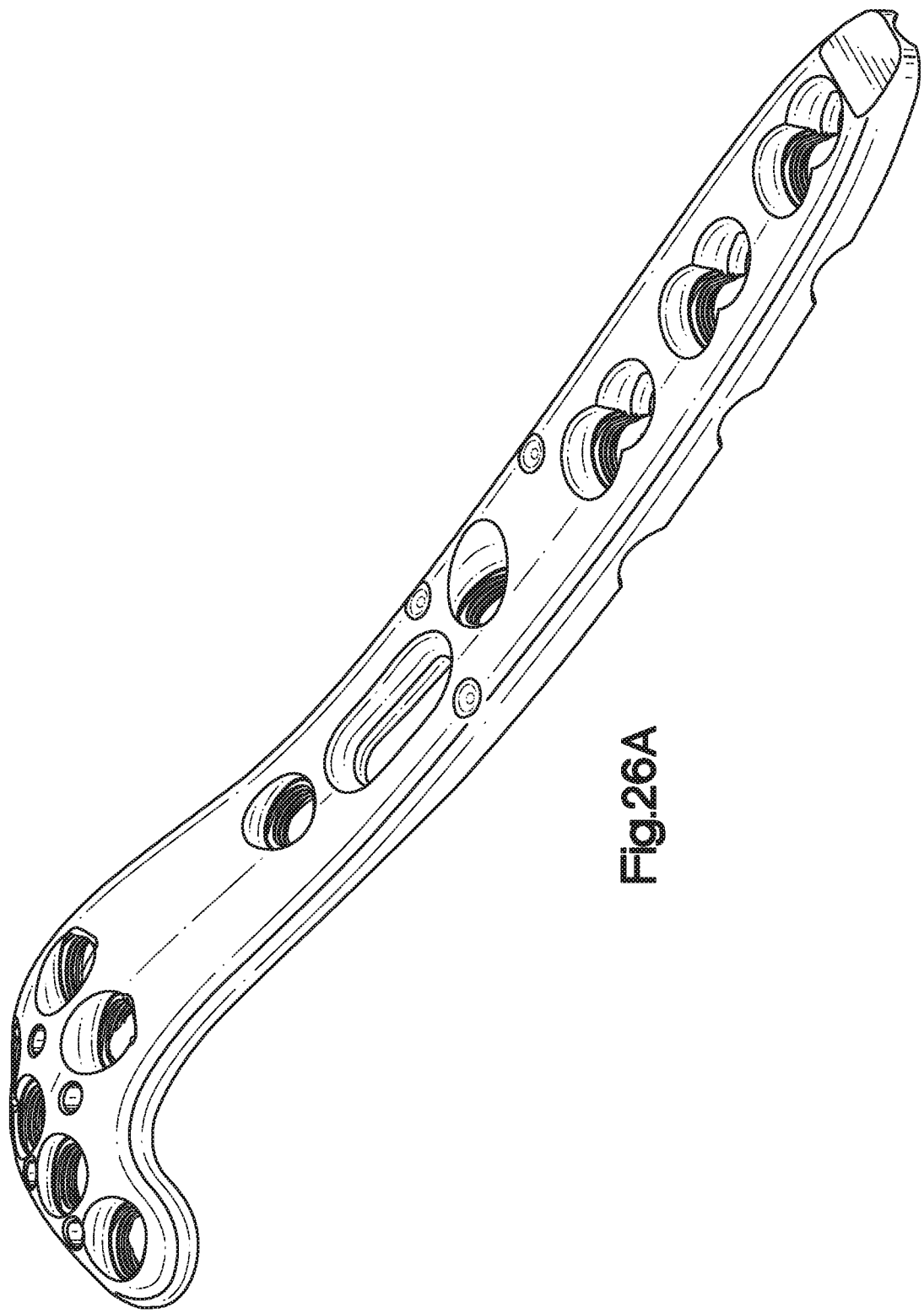
FIGS. 26A through 26G show respective views of a sixth additional bone plate, according to another embodiment of the present disclosure, the bone plate having various combination holes that include a trigon locking hole intersected by a compression hole, these views being a perspective view (FIG. 26A), top view (FIG. 26B), right side view (FIG. 26C), bottom view (FIG. 26D), left side view (FIG. 26E), front view (FIG. 26F), and rear view (FIG. 26G) of the bone plate.
Figure 26B:
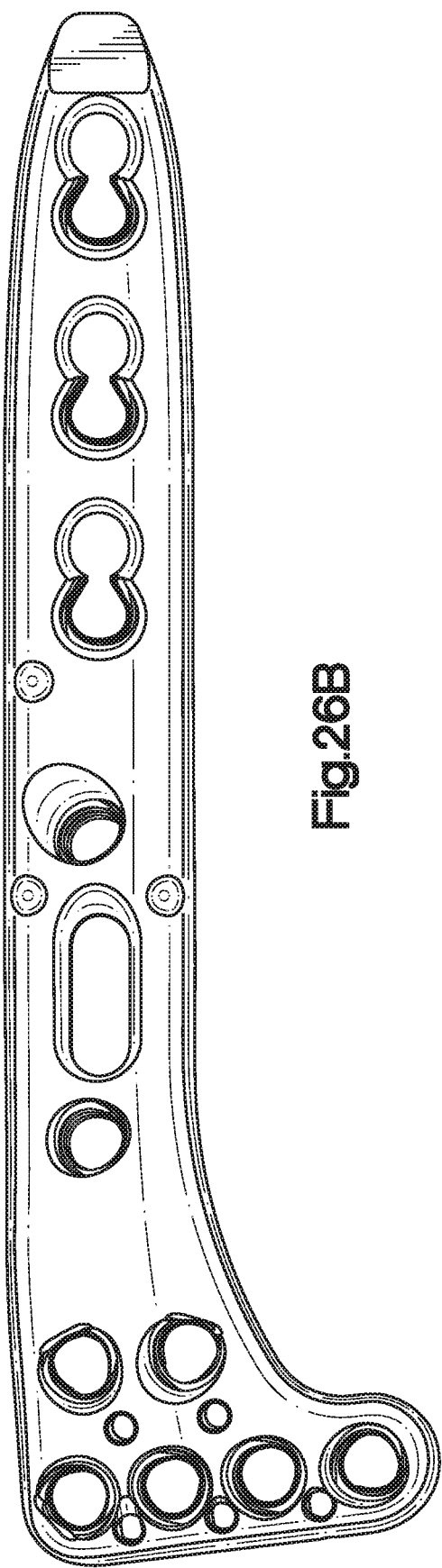
Figure 26C:
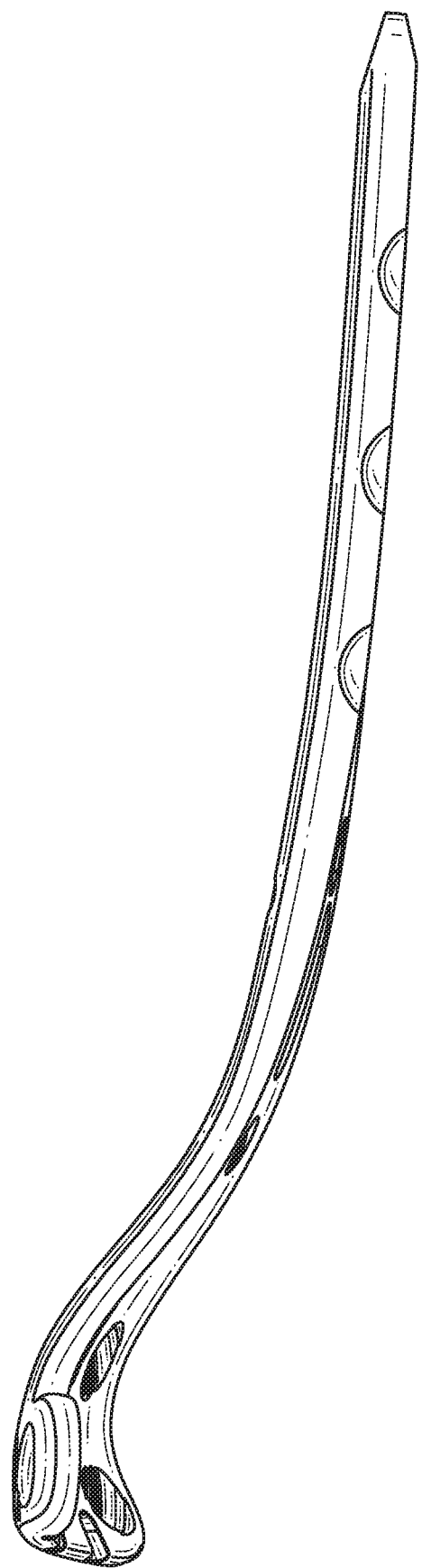
Figure 26D:
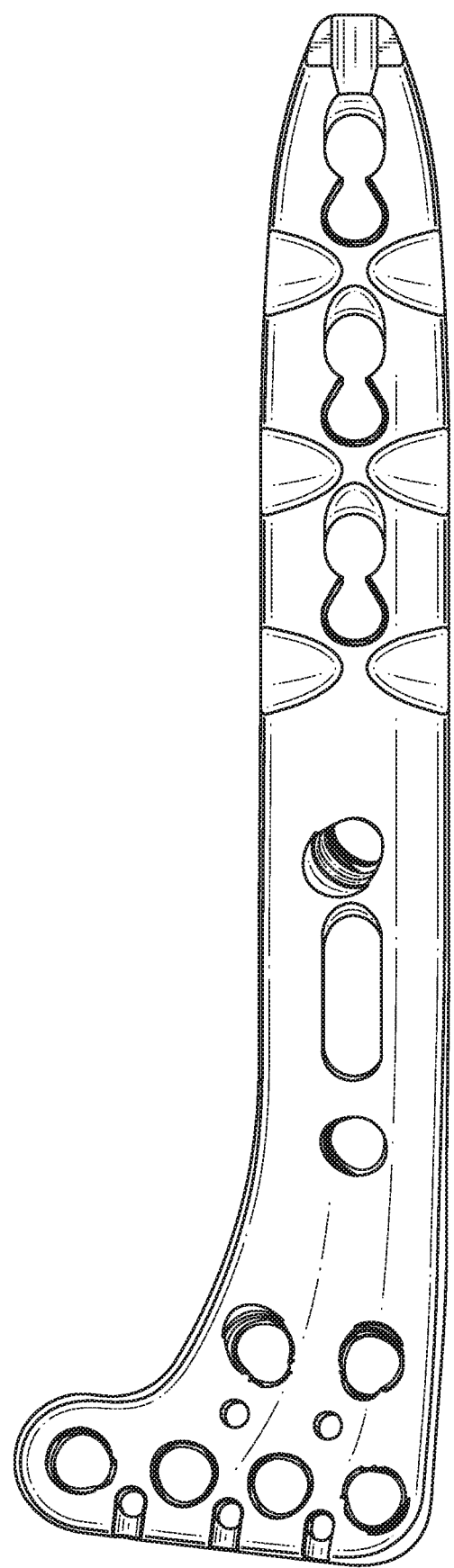
Figure 26E:
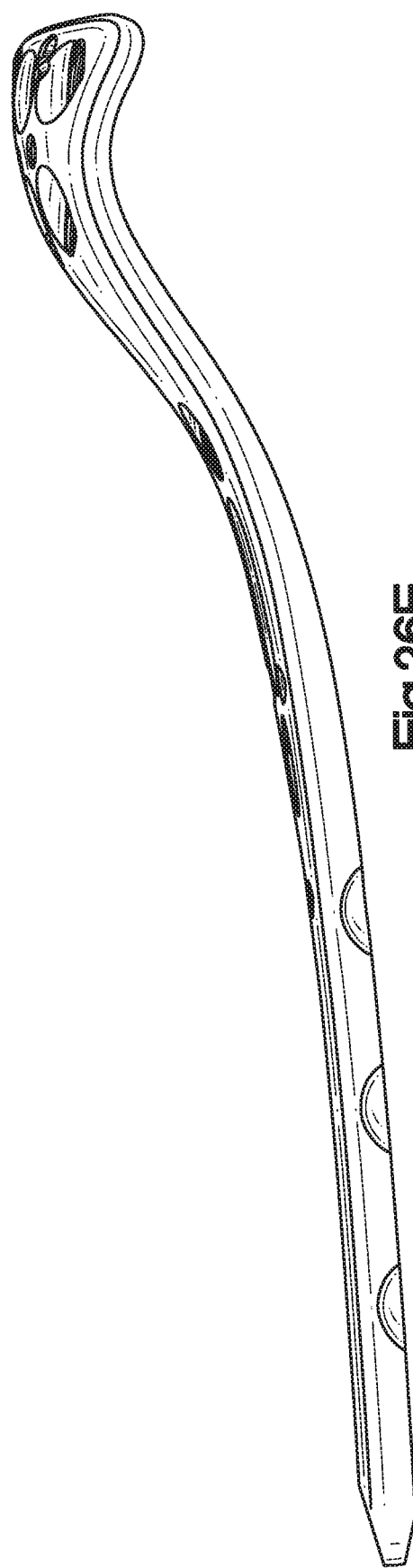
Figure 26F:
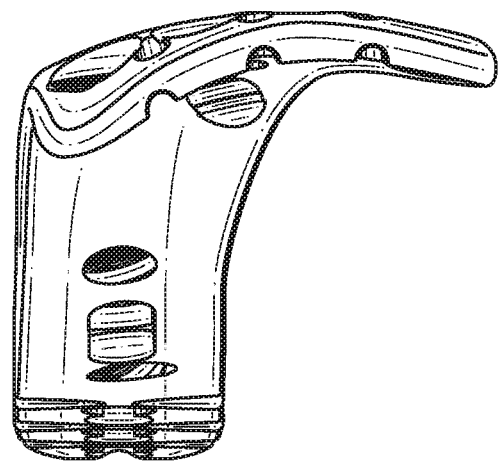
Figure 26G:
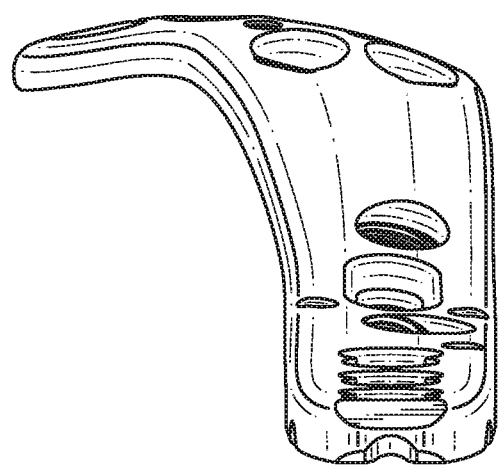
Figure 27A:
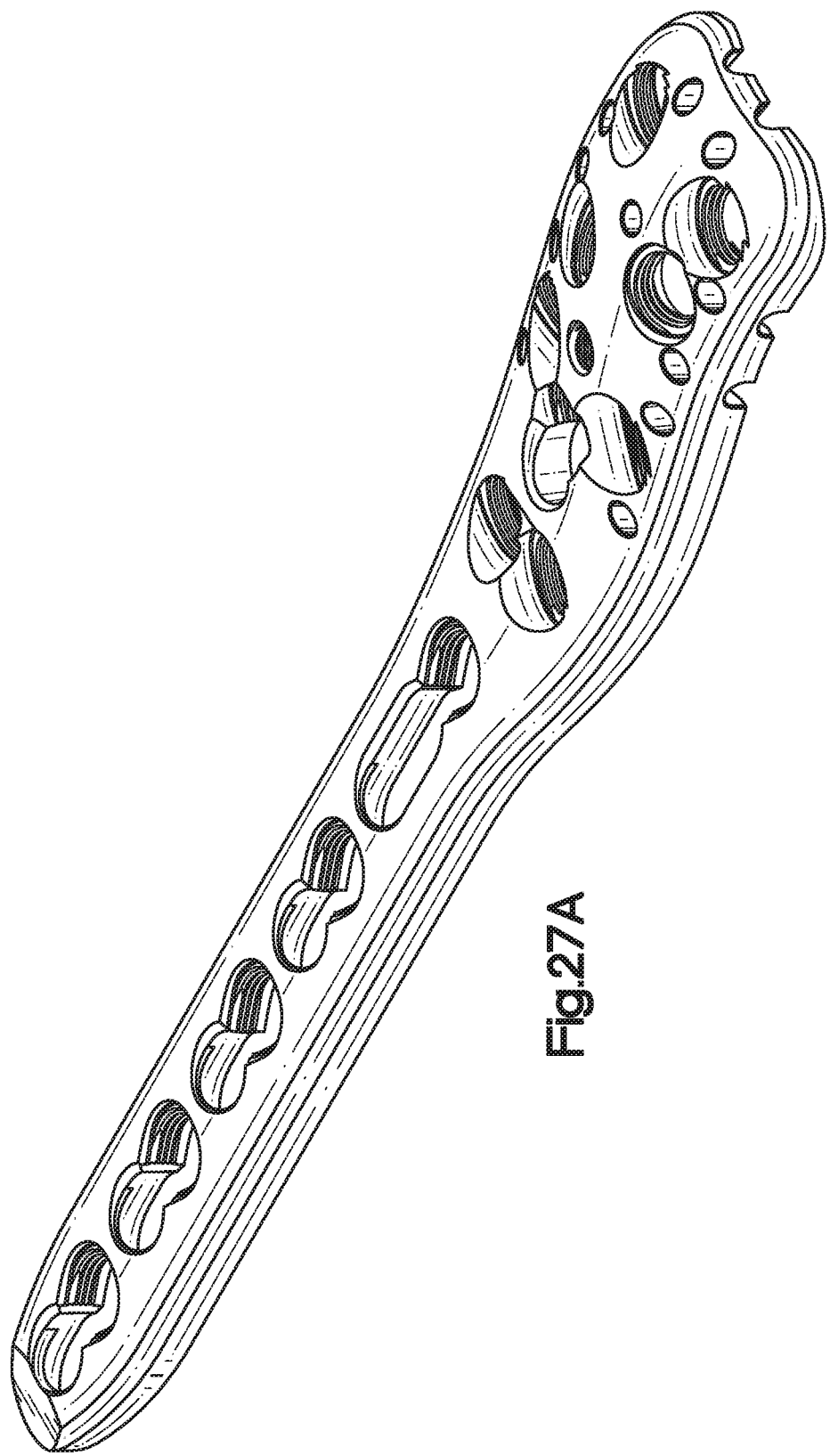
FIGS. 27A through 27G show respective views of a seventh additional bone plate, according to another embodiment of the present disclosure, the bone plate having various combination holes that include a trigon locking hole intersected by a compression hole, these views being a perspective view (FIG. 27A), top view (FIG. 27B), right side view (FIG. 27C), bottom view (FIG. 27D), left side view (FIG. 27E), front view (FIG. 27F), and rear view (FIG. 27G) of the bone plate.
Figure 27B:
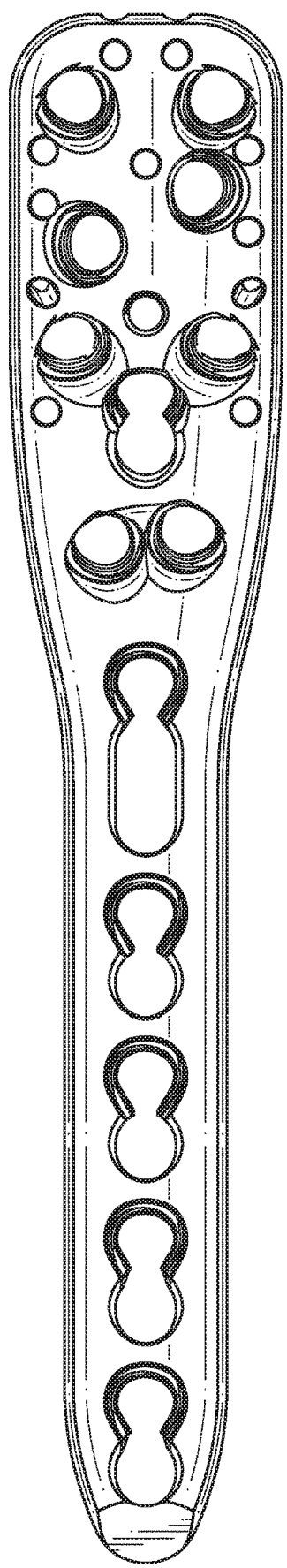
Figure 27C:
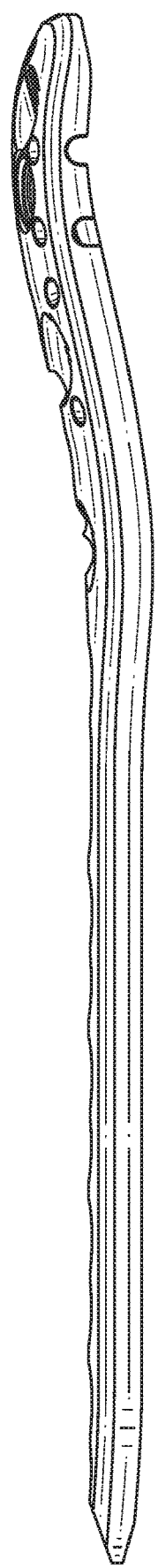
Figure 27D:
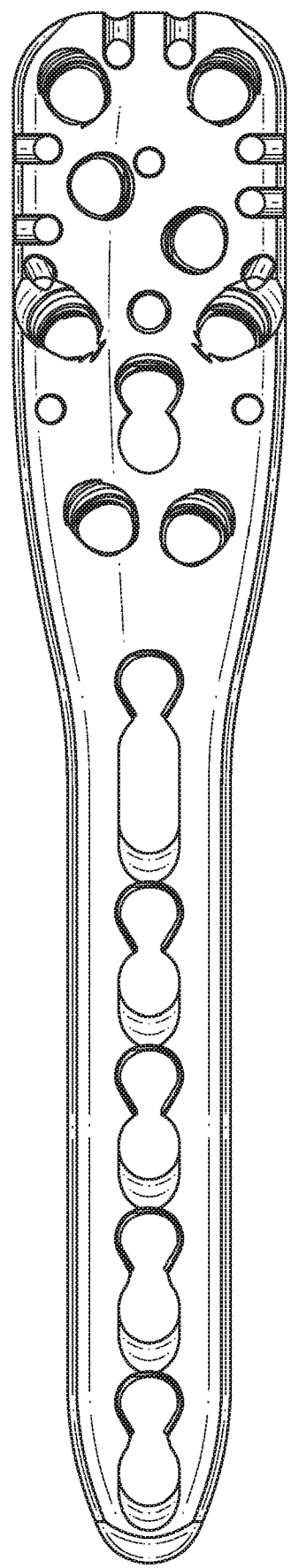
Figure 27E:
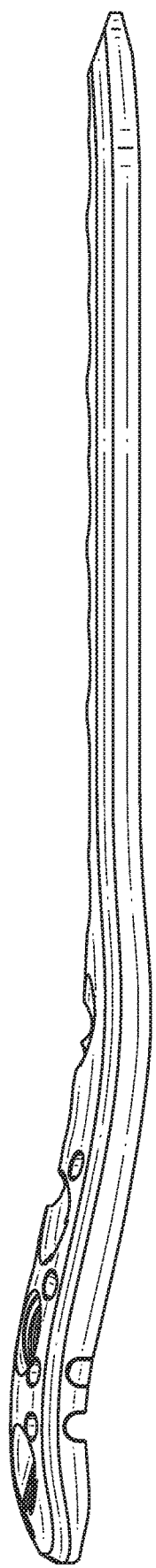
Figure 27F:
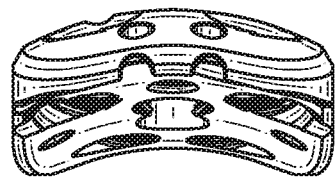
Figure 27G:
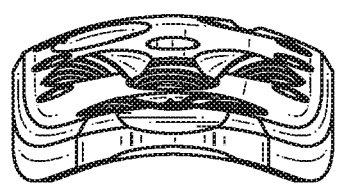
Figure 28A:
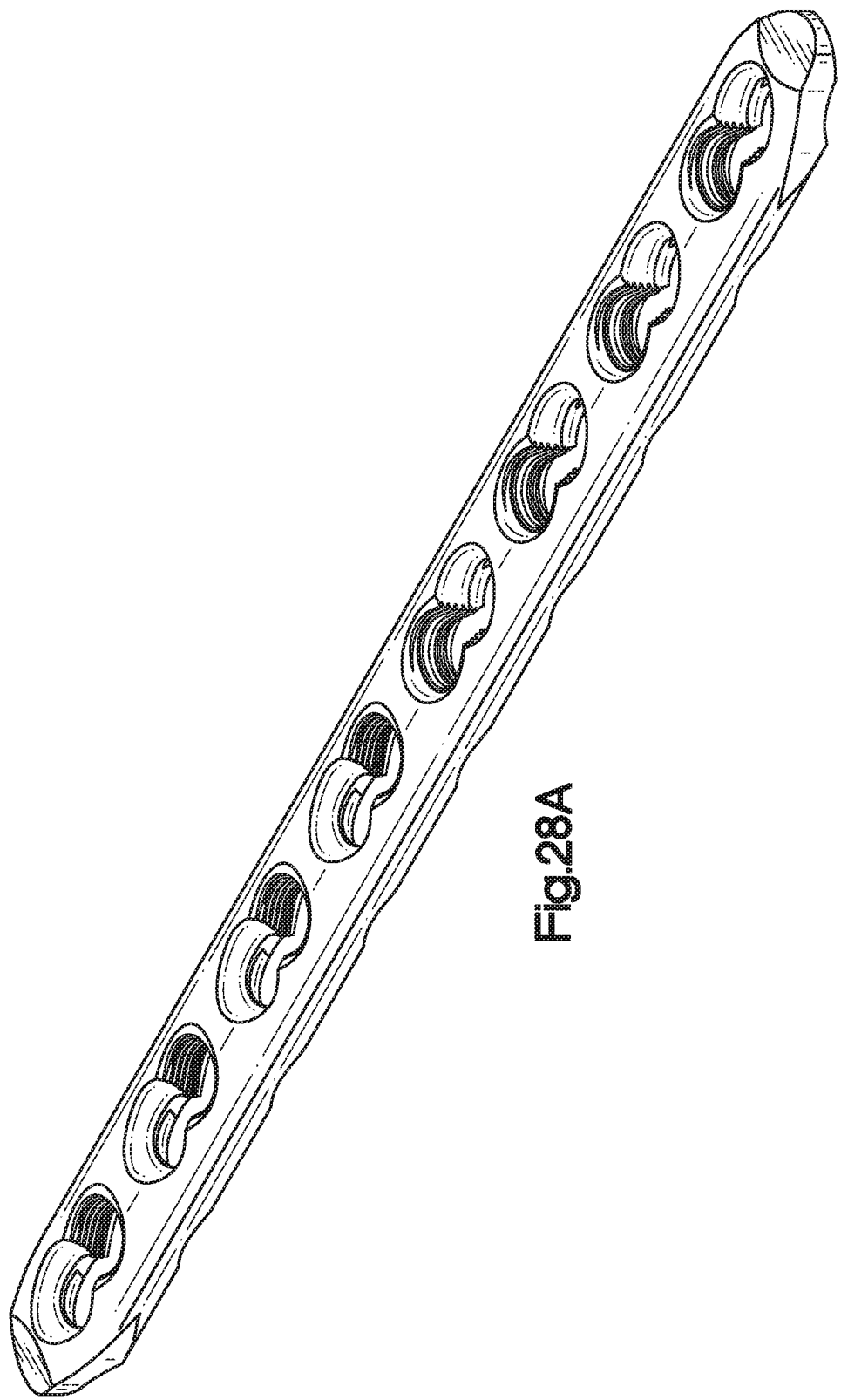
FIGS. 28A through 28G show respective views of an eighth additional bone plate, according to another embodiment of the present disclosure, the bone plate having various combination holes that include a trigon locking hole intersected by a compression hole, these views being a perspective view (FIG. 28A), top view (FIG. 28B), right side view (FIG. 28C), bottom view (FIG. 28D), front view (FIG. 28E), left side view (FIG. 28F), and rear view (FIG. 28G) of the bone plate.
Figure 28B:
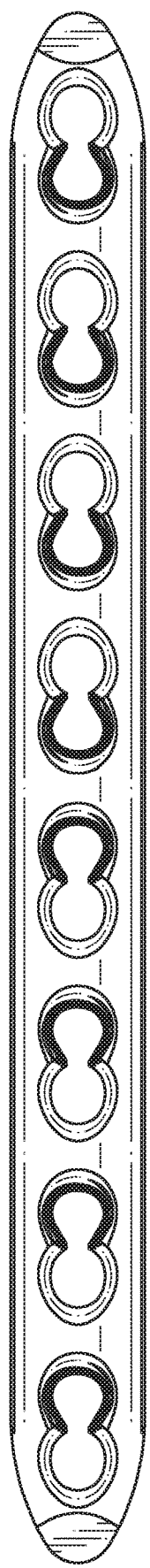
Figure 28C:
Figure 28D:
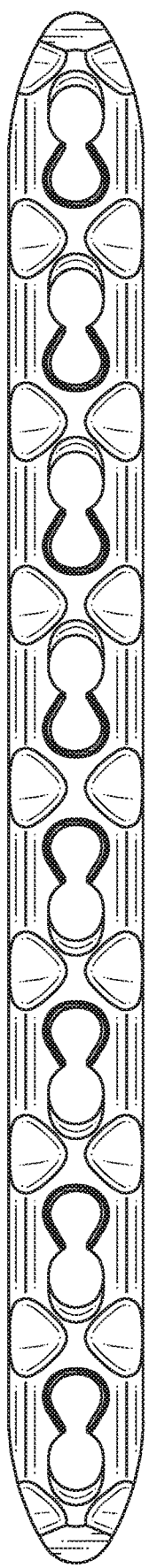
Figure 28E:
Figure 28F:
Figure 28G:
Figure 29A:
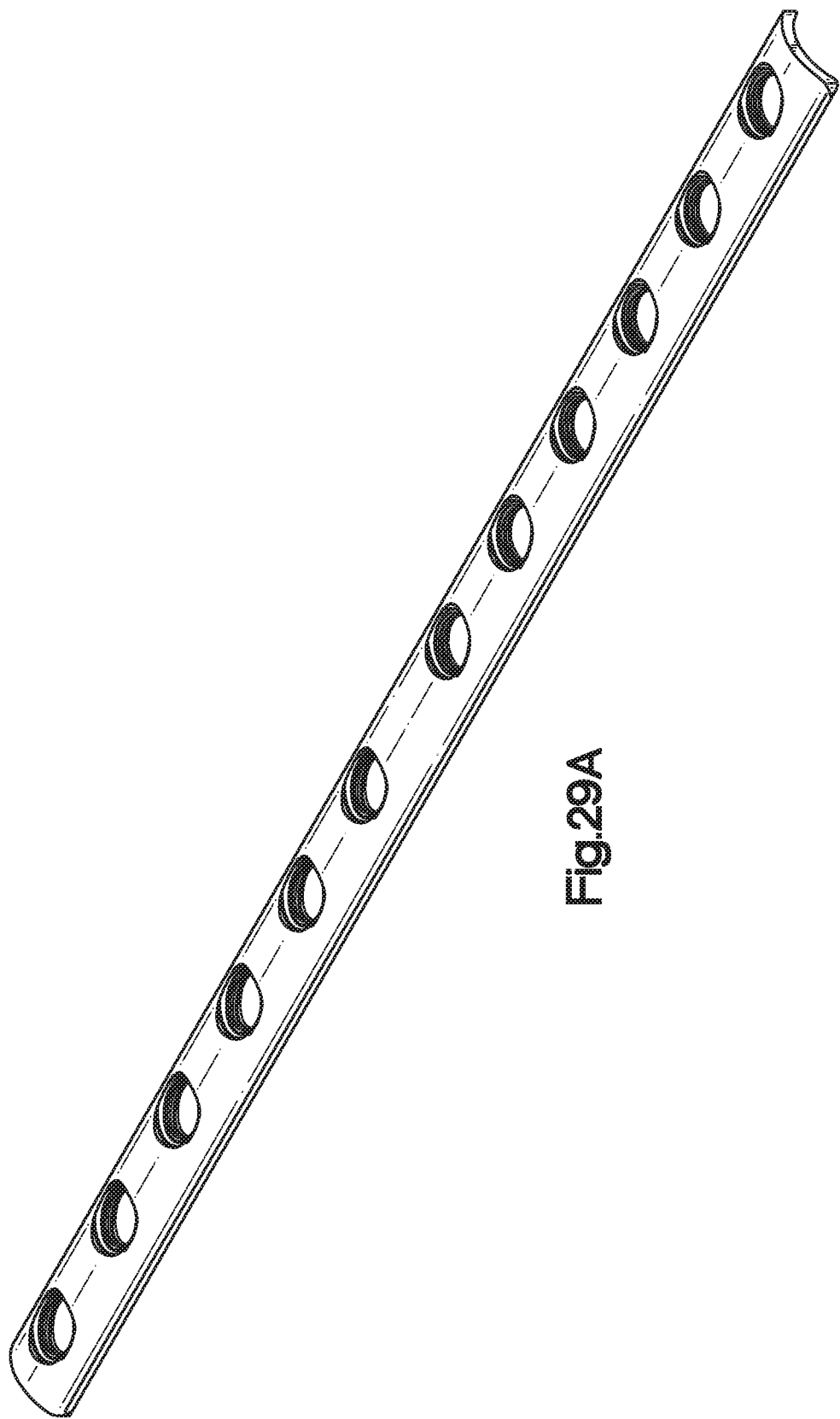
FIGS. 29A through 29G show respective views of a bone plate having trigon locking holes, these views being a perspective view (FIG. 29A), top view (FIG. 29B), right side view (FIG. 29C), bottom view (FIG. 29D), front view (FIG. 29E), left side view (FIG. 29F), and rear view (FIG. 29G) of the bone plate.
Figure 29B:
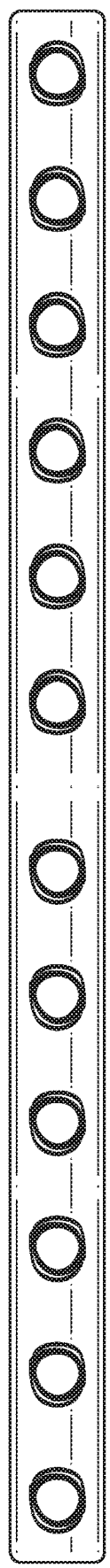
Figure 29C:
Figure 29D:
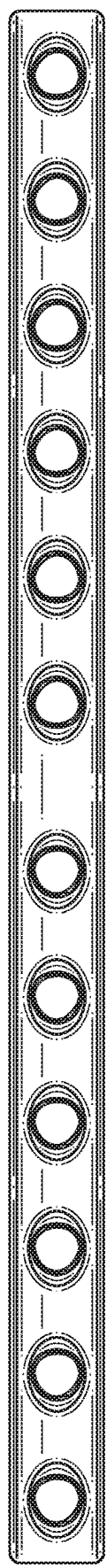
Figure 29E:
Figure 29F:
Figure 29G:

Referring now to FIGS. 18 through 20, in further embodiments, a combi-hole 90' can be effectively defined by first and second VA locking holes 6 that intersect one another. Such combi-holes 90' can be referred to herein as VA-VA combi-holes 90'. In such embodiments, the second surface 24b' is also a locking surface. Accordingly, locking surface 24a can be referred to as the first locking surface 24a, and the second surface 24b' can be referred to as the second locking surface 24b'. As above, the first locking surface 24a can define first, second, and third columns 26a, 26b, 26c separated from each other by a first corner 28a, a gap between the VA locking holes 6 (where a second corner would otherwise exist), and a third corner 28c, respectively. The second locking surface 24b' can define fourth, fifth, and sixth columns 26d, 26e, 26f separated from each other by a fourth corner 28d, the gap (where a fifth corner would otherwise exist), and a sixth corner 28f, respectively. The threads 9 of the combi-hole 90' extend along one or more thread paths (i.e., single-lead, double-lead, etc.) that preferably traverse the locking surfaces 24a, 24b' in uninterrupted fashion between the upper and lower surfaces 18, 20 of the bone plate 4. The VA-VA combi-holes 90' can be defined by polygonal-shaped VA locking holes 6, such as the trigon-shaped VA locking holes 6 depicted, although any of the polygonal-shaped VA locking holes 6 described above can be incorporated into a VA-VA combi-hole 90'.

The VA-VA combi-holes 90' of the present embodiments can employ thread transition zones 130 similar to those described above with reference to FIGS. 13A-15B. For example, as shown in FIG. 18, the VA-VA combi-hole 90' can define a linear elongated transition zone 130 on each longitudinal side of the intersection boundary 119. In such embodiments, the intersection boundary 119 can define an interface between the second and sixth columns 26b,f and another interface between the third and fifth columns 26c,e. In other embodiments, as shown in FIGS. 19 and 20, the combi-holes 90' can employ arcuate, convex thread transition zones 130 and transition portions 132, similar to those described above. For example, the VA-VA combi-hole 90' of FIG. 19 can employ a thread transition zone 130 in which the first and second locking surfaces 24a, 24b' define elongated arcuate, convex transition portions 132 on each longitudinal side of the intersection boundary 119, each similar to the transition portions 132 described above with reference to FIGS. 14A through 14E. Moreover, the VA-VA combi-hole 90' of FIG. 20 can employ a thread transition zone 130 in which the first and second locking surfaces 24a, 24b' define elongated columns 26b,c,e,f and arcuate, convex transition portions 132 on each longitudinal side of the intersection boundary 119, similar to the transition zone 130 described above with reference to FIGS. 15A and 15B. It should be appreciated that, in other embodiments, the VA-VA combi-hole 90' can be devoid of a thread transition region (such as the thread transition regions 130 described above with reference to FIGS. 13A-15B).

It should further be appreciated that any of the combi-holes described above can be modified such that the VA locking hole(s) 6 thereof employs a polygonal horizontal hole profile according to any of the polygonal hole shapes described herein.

With reference to FIGS. 21A through 29G, additional examples of bone plates will be described that include various trigon locking hole geometries, such as stand-alone locking holes and combi-holes having a locking hole intersected by a compression hole.

FIGS. 21A through 21G show an example bone plate, particularly a bone plate for treating a medial distal portion of a tibia, the bone plate having a "low bend" geometry and having locking holes, including stand-alone locking holes and combi-holes that employ trigon VA locking hole geometries, wherein at least some and up to all of the locking holes are configured for use with standard-type locking screws having shaft major diameters of about 3.5 mm. According to one naming convention, the bone plate of the present example can be categorized as follows: LCP Medial Distal Tibial Plate 3.5, Low Bend.

FIGS. 22A through 22G show an example bone plate, particularly a bone plate for treating an olecranon, the bone plate having locking holes, including stand-alone locking holes and combi-holes that employ trigon VA locking hole geometries, wherein at least some and up to all of the locking holes are configured for use with both standard-type locking screws and VA locking screws having shaft major diameters from about 2.7 mm to about 3.5 mm. According to one naming convention, the bone plate of the present example can be categorized as follows: VA-LCP Olecranon Plate 2.7/3.5.

FIGS. 23A through 23G show an example bone plate, particularly a bone plate for treating a distal radius, the bone plate having locking holes, including stand-alone locking holes and combi-holes that employ trigon VA locking hole geometries, wherein at least some and up to all of the locking holes are configured for use with both standard-type locking screws and VA locking screws having shaft major diameters of about 2.4 mm. According to one naming convention, the bone plate of the present example can be categorized as follows: VA-LCP Two-Column Distal Radius Plate 2.4.

FIGS. 24A through 24G show an example show an example bone plate, particularly a bone plate for treating a lateral distal fibula, the bone plate having locking holes, including stand-alone locking holes and combi-holes that employ trigon VA locking hole geometries, wherein at least some and up to all of the locking holes are configured for use with both standard-type locking screws and VA locking screws having shaft major diameters of about 2.7 mm. According to one naming convention, the bone plate of the present example can be categorized as follows: VA-LCP Lateral Distal Fibula Plate 2.7.

FIGS. 25A through 25G show an example show an example bone plate, particularly a bone plate for treating a condyle, the bone plate having locking holes, including combi-holes that employ trigon VA locking hole geometries and also stand-alone locking holes having different geometries, wherein at least some and up to all of the locking holes are configured for use with both standard-type locking screws and VA locking screws having shaft major diameters from about 4.5 mm to about 5.0 mm. According to one naming convention, the bone plate of the present example can be categorized as follows: VA-LCP Condylar Plate 4.5/5.0.

FIGS. 26A through 26G show an example show an example bone plate, particularly a bone plate for treating a proximal tibia, the bone plate having a "small bend" geometry having locking holes, including stand-alone locking holes and combi-holes that employ trigon VA locking hole geometries, wherein at least some and up to all of the locking holes are configured for use with both standard-type locking screws and VA locking screws having shaft major diameters of about 3.5 mm. According to one naming convention, the bone plate of the present example can be categorized as follows: VA-LCP Proximal Tibial Plate 3.5, Small Bend.

FIGS. 27A through 27G show an example show an example bone plate, particularly a bone plate for treating a proximal humerus, the bone plate having locking holes, including stand-alone locking holes and combi-holes that employ trigon locking hole geometries, wherein at least some and up to all of the locking holes are configured for use with standard-type locking screws. According to one naming convention, the bone plate of the present example can be categorized as follows: LCP Proximal Humerus Plate (Philos).

FIGS. 28A through 28G show an example show an example bone plate, particularly a straight bone plate having combi-holes that employ trigon locking hole geometries, wherein the locking holes are configured for use with standard-type locking screws having shaft major diameters of about 3.5 mm. According to one naming convention, the bone plate of the present example can be categorized as follows: LCP Plate 3.5, straight FIGS. 29A through 29G show an example show an example bone plate, particularly a straight bone plate having stand-alone locking holes that employ trigon locking hole geometries. According to one naming convention, the bone plate of the present example can be categorized as follows: ⅓ Tubular Locking.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A bone plate, comprising:
   a plate body that defines a combination hole comprising a locking hole and a compression hole that intersect one another and each extends from an outer surface of the plate body to a bone-facing surface of the plate body, wherein the locking hole and the compression hole extend away from each other along a longitudinal axis,
   the plate body further defining 1) a locking surface that defines the locking hole, 2) a second surface that defines the compression hole, and 3) interface edges along an intersection boundary between the locking surface and the second surface;
   wherein the locking surface further defines:
      first, second, and third columns sequentially located about a central axis of the locking hole, each column having a first side and a second side;
      a first recess extending from the second side of the first column to the first side of the second column;
      an additional recess extending from the second side of the third column to the first side of the first column;

a transition zone between the first side of the second column and the second side of the third column, wherein the locking surface in the transition zone is elongated and extends to the intersection boundary; and plate threads that traverse each of the columns and at least portions of the first recess, the additional recess, and the transition zone, wherein crests of the plate threads extend linearly from the first side to the second side of each column.

2. The bone plate of claim 1, wherein the longitudinal axis intersects the first column, and the second and third columns are substantially equidistantly spaced from the longitudinal axis with respect to a lateral direction perpendicular to the longitudinal axis.

3. The bone plate of claim 2, wherein:
each column defines a crest trajectory axis that intersects the crest of each fully formed plate thread in the column, such that the crest trajectory axes of the first, second, and third columns are 1) substantially equidistantly spaced from the central axis, and 2) located at substantially equivalent intervals about the central axis; and in a reference plane orthogonal to the central axis, the crest trajectory axes of the first, second, and third columns are spaced from the central axis at a substantially equivalent radial distance measured along a radial direction perpendicular to the central axis.

4. The bone plate of claim 3, wherein the crest trajectory axes are linear and are each oriented at an angle in a range of about 5 degrees to about 30 degrees relative to the central axis.

5. The bone plate of claim 3, wherein each column defines a column length measured from the first side to the second side along a respective direction perpendicular to the radial direction in the reference plane, the column lengths of the second and third columns are equivalent, and the column length of the first column is different than the column lengths of the second and third columns.

6. The bone plate of claim 5, wherein a ratio of the column length of the first column to the column lengths of the second and third columns is in a range of about 1:2 to about 1:15.

7. The bone plate of claim 6, wherein the ratio of the column length of the first column to the column lengths of the second and third columns is in a range of about 1:5 to about 1:8.

8. The bone plate of claim 6, wherein the second and third columns extend to the intersection boundary.

9. The bone plate of claim 3, wherein the locking surface further defines transition portions extending respectively from the second and third columns to the intersection boundary, and the transition portions are located opposite each other along the lateral direction and are arcuately convex and define transition radii, such that a ratio of the radial distance to the transition radii is in a range of about 1:2.1 to about 1:2.7 in the reference plane.

10. The bone plate of claim 3, wherein the radial distance is less than a minimum distance measured from the central axis to the intersection boundary with respect to a longitudinal direction oriented along the longitudinal axis.

11. The bone plate of claim 10, wherein:
the plate threads define fully formed thread profiles that include the crests and further include roots and flanks that extend from the roots to the crests;
at least some of the plate threads extend to the intersection boundary such that the interface edges on both sides of the longitudinal axis with respect to the lateral direction include edges of the fully formed thread profiles.

12. The bone plate of claim 11, wherein the plate threads traverse the locking surface such that a thread height measured from the crest to the root is substantially constant along at least one partial revolution about the central axis from the intersection boundary on one side of the longitudinal axis to the intersection boundary on the opposite side of the longitudinal axis.

13. A bone plate, comprising:
a plate body that defines an outer surface, a bone-facing surface opposite the outer surface, and a combination hole comprising a locking hole and a compression hole that intersect one another and each extending from the outer surface to the bone-facing surface, wherein the locking hole and the compression hole extend away from each other along a longitudinal axis,
the plate body further defining 1) a locking surface that defines the locking hole, and 2) a second surface that defines the compression hole;
wherein the locking surface further defines:
a plurality of columns sequentially located about a central axis of the locking hole in a polygonal pattern;
a plurality of recesses located, respectively, between at least some of the columns; and
plate threads that traverse each of the columns, wherein crests of the plate threads extend linearly from a first side of each column to a second side of each column; and
wherein:
the plate body defines an intersection boundary between the locking surface and the second surface, and a first portion of the intersection boundary on a first side of the longitudinal axis is separated from a second portion of the intersection boundary on a second side of the longitudinal axis by a gap that is open to the locking hole and the compression hole;
the longitudinal axis intersects a first column of the plurality of columns and extends centrally through the gap; and
the plurality of columns further comprises second and third columns, wherein the second and third columns are substantially equidistantly spaced from the longitudinal axis with respect to a lateral direction perpendicular to the longitudinal axis.

14. The bone plate of claim 13, wherein:
the plate threads define fully formed thread profiles that include the crests and further include roots and flanks that extend from the roots to the crests;
at least some of the plate threads extend to the intersection boundary such that interface edges between the locking surface and the second surface along the first and second portions of the intersection boundary include edges of the fully formed thread profiles.

15. The bone plate of claim 14, wherein the plate threads traverse the locking surface such that a thread height measured from the crest to the root is substantially constant along at least one partial revolution about the central axis from the second portion of the intersection boundary to the first portion of the intersection boundary.

16. The bone plate of claim 13, wherein the bone plate is formed of a material selected from the group comprising stainless steel, titanium, a titanium-aluminum-niobium (TAN) alloy, a titanium-aluminum-vanadium (TAV) alloy, a titanium-molybdenum alloy, a cobalt-chrome alloy, and nitinol.

17. The bone plate of claim 14, wherein the flanks of the plate threads define a plate thread angle in a range of about 20 degrees to about 60 degrees.

18. The bone plate of claim 17, wherein the flanks of the plate threads have a first portion that defines the thread angle and a second portion that defines a second thread angle, wherein the second portions of the flanks are located between the first portions and the crests of the plate threads, respectively, the thread angle is in a range of about 25 degrees to about 40 degrees, and the second thread angle is in a range of about 40 degrees to about 75 degrees.

19. The bone plate of claim 17, wherein:
- the plate threads define fully formed thread profiles comprising, the crests, the roots, and the flanks;
- the roots, crests, and flanks collectively deviate from a reference thread profile that is V-shaped and defines crest reference points at apices at a first side thereof and root reference points at apices at a second side thereof opposite the first side; and
- a thread height measured from the crests to the roots is less than a reference height measured from the crest reference points to the root reference points, such that a ratio of the thread height to the reference height is in a range of 0.50:1 to 1.00:1.

20. The bone plate of claim 13, wherein the polygonal pattern is a trigon pattern.

* * * * *